(12) United States Patent
Rahimi

(10) Patent No.: US 11,406,709 B2
(45) Date of Patent: Aug. 9, 2022

(54) THERAPEUTIC AND RESEARCH APPLICATION OF PDCL3

(71) Applicant: TRUSTEES OF BOSTON UNIVERSITY, Boston, MA (US)

(72) Inventor: Nader Rahimi, Westwood, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 556 days.

(21) Appl. No.: 15/510,965

(22) PCT Filed: Sep. 15, 2015

(86) PCT No.: PCT/US2015/050108
§ 371 (c)(1),
(2) Date: Mar. 13, 2017

(87) PCT Pub. No.: WO2016/044219
PCT Pub. Date: Mar. 24, 2016

(65) Prior Publication Data
US 2017/0274075 A1 Sep. 28, 2017

Related U.S. Application Data

(60) Provisional application No. 62/050,375, filed on Sep. 15, 2014.

(51) Int. Cl.
| | |
|---|---|
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |
| *C07K 14/00* | (2006.01) |
| *A61K 38/16* | (2006.01) |
| *A61K 39/395* | (2006.01) |
| *C07K 14/47* | (2006.01) |
| *A61K 38/17* | (2006.01) |
| *A61K 31/513* | (2006.01) |
| *A61K 31/4748* | (2006.01) |
| *A61K 45/06* | (2006.01) |
| *A61K 31/475* | (2006.01) |
| *A61K 31/122* | (2006.01) |
| *A61K 31/404* | (2006.01) |
| *A61K 31/12* | (2006.01) |
| *A61K 31/13* | (2006.01) |
| *A61K 31/4035* | (2006.01) |
| *A61K 31/428* | (2006.01) |
| *A61K 31/4709* | (2006.01) |
| *A61K 31/519* | (2006.01) |

(Continued)

(52) U.S. Cl.
CPC ........ *A61K 39/39558* (2013.01); *A61K 31/12* (2013.01); *A61K 31/122* (2013.01); *A61K 31/13* (2013.01); *A61K 31/277* (2013.01); *A61K 31/404* (2013.01); *A61K 31/4035* (2013.01); *A61K 31/428* (2013.01); *A61K 31/475* (2013.01); *A61K 31/4709* (2013.01); *A61K 31/4748* (2013.01); *A61K 31/513* (2013.01); *A61K 31/519* (2013.01); *A61K 31/7115* (2013.01); *A61K 38/02* (2013.01); *A61K 38/1709* (2013.01); *A61K 45/06* (2013.01); *C07K 14/00* (2013.01); *C07K 14/47* (2013.01); *C07K 16/28* (2013.01); *C07K 17/00* (2013.01); *C07K 2319/00* (2013.01); *C07K 2319/30* (2013.01); *C07K 2319/31* (2013.01); *C07K 2319/35* (2013.01); *C07K 2319/40* (2013.01); *C07K 2319/705* (2013.01); *C07K 2319/90* (2013.01)

(58) Field of Classification Search
None
See application file for complete search history.

(56) References Cited

U.S. PATENT DOCUMENTS

| | | |
|---|---|---|
| 8,076,139 B1 | 12/2011 | Hamm et al. |
| 8,440,685 B1 | 5/2013 | Delack |

(Continued)

FOREIGN PATENT DOCUMENTS

WO 2006031922 A2 3/2006

OTHER PUBLICATIONS

GenBank Database, Accession No. BC001021, 2 pages (2006) (Year: 2006).*

(Continued)

*Primary Examiner* — Thea D' Ambrosio
(74) *Attorney, Agent, or Firm* — Nixon Peabody LLP; Ronald I. Eisenstein; Jeanne Jodoin

(57) ABSTRACT

Described herein are novel compositions comprising, for example, PDCL3 polypeptides having VEGFR-2 inhibitory activity, inhibitory PDCL3 antibodies and PDCL3-binding fragments thereof, or PDCL3 inhibitory nucleic acid molecules, and methods of their use in anti-angiogenesis and anti-tumor proliferation and invasiveness therapies, such as the treatment of cancer, as well as the treatment of those vascular diseases where pathological angiogenesis plays a role, such as in carotid artery disease, macular degeneration, and plaque neovascularization. Also described herein are novel compositions comprising engineered PDCL3 polypeptides having enhanced chaperone activity, recombinant cells comprising such engineered PDCL3 polypeptides having enhanced chaperone activity, and methods thereof for therapeutic protein production and in vitro protein synthesis.

11 Claims, 28 Drawing Sheets
Specification includes a Sequence Listing.

(51) Int. Cl.
*A61K 31/277* (2006.01)
*A61K 31/7115* (2006.01)
*A61K 38/02* (2006.01)
*C07K 16/28* (2006.01)

(56) References Cited

U.S. PATENT DOCUMENTS

2003/0232782 A1 12/2003 Escalante-Semerena et al.
2010/0160228 A1 6/2010 Ivaska et al.
2012/0302737 A1 11/2012 Christensen et al.

OTHER PUBLICATIONS

Terpe, K., Appl. Microbiol. Biotechnol. 60:523-533 (2003) (Year: 2003).*
Blaauw et al., EMBO J. 22:5047-5057 (2003) (Year: 2003).*
UniProt Database, Accession No. Q9H2J4, 10 pages (2001) (Year: 2001).*
Srinivasan et al., "Hypoxia-induced expression of phosducin-like 3 regulates expression of VEGFR-2 and promotes angiogenesis", Angiogenesis, 18(4):449-62 (2015).
Srinivasan et al., "Identification of PDCL3 as a novel chaperone protein involved in the generation of functional VEGF receptor 2", J Biol Chem, 288(32):23171-81 (2013).
Wyatt et al., "Hypochlorite-induced structural modifications enhance the chaperone activity of human α2-macroglobulin", Proc Natl Acad Sci U S A, 111(20):E2081-90 (2014).

* cited by examiner

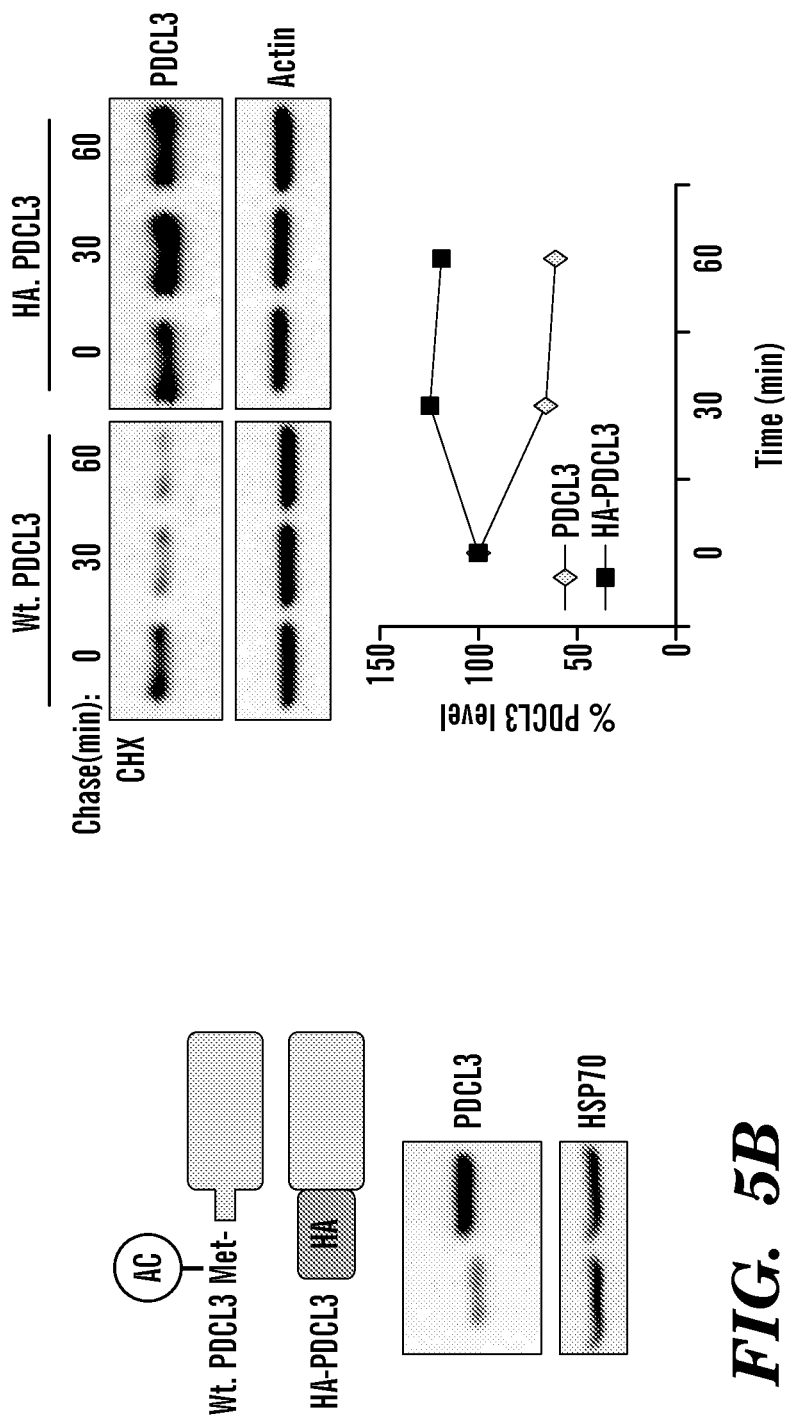

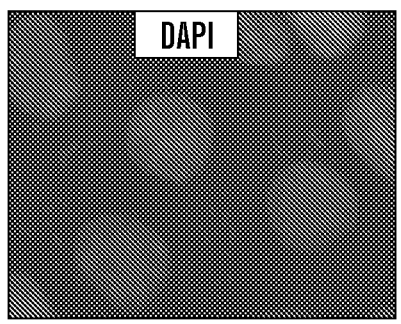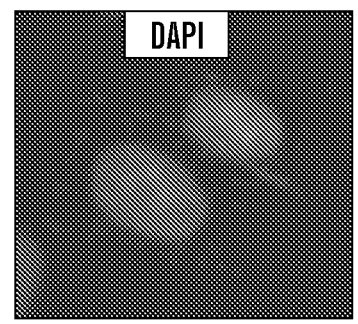
FIG. 7C  FIG. 7D
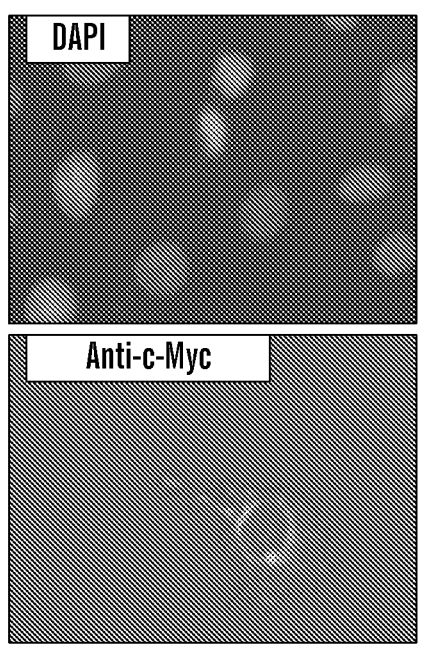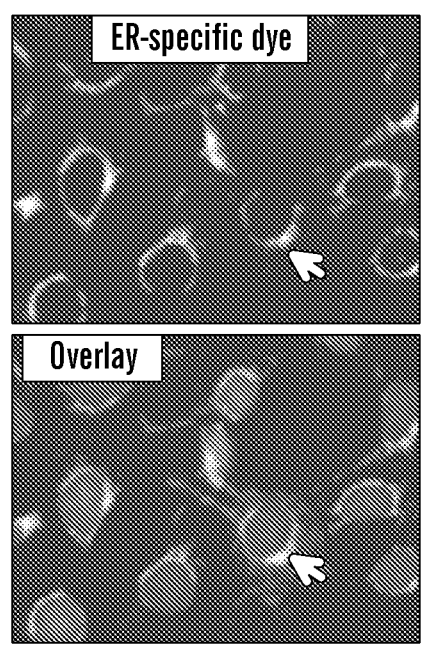
FIG. 7E

Blot: Anti-VEGFR-2    Anti-VEGFR-1    CSF-1R

Blot: Anti-Myc

Blot: Anti-PLCγ1

| HIT Compounds Name | Known function |
|---|---|
| Reserpine | Inhibits vesicular catecholine and serotonin uptake |
| DAPH | Protein tyrosine kinase inhibitor, specific for EGFR. |
| AC-93253 iodide | Potent, cell permeable, subtype selective retinoic acid receptor. |
| Emodin | p56lck Tyrosine kinase inhibitor |
| Sunitinib malate | receptor tyrosine kinase inhibitor |
| GW2974 | Dual EGFR and ErbB-2 receptor tyrosine kinase inhibitor |
| Urapidil Hydrochloride | Soluble guanylyl cyclase activator and aldose reductase inhibitor |
| Mecamylamine hydrochloride | Nicotinic acetylcholine receptor antagonist |
| (-)_MK-801 hydrogen maleate | Less active enantiomer of (+)-MK-801 hydrogen maleate; anticonvulsan. |
| AGK2 | SIRT2 inhibitor. AGK2 rescues dopamine neurons from a-synuclein tox. |
| Tyrphostin AG 112 | Protein tyrosine kinase inhibitor. |
| Tyrphostin 23 | Protein tryrosine kinase EGFR inhibitor. |
| Tyrphostin 51 | EGFR tyrosine kinase inhibitor |
| I-Ome-Tyrophostin AG 538 | Insulin growth factor 1 (IGF-1) receptor protein tyrosine kinase inhibitor. |
| Isoliquiritgenin | alpha1 Adrenoceptor antagonist it also sirtuin-activating . |

*FIG. 14A*

Structure of HIT compounds

Mecamylamine hydrochloride (-)-MK-801 hydrogen maleate

AC-93253 iodide

GW2974

Tyrphostin AG 112

Tyrphostin 23

Structure of HIT compounds

DAPH

Emodin

Sunitinib malate
Reserpine

Tyrphostin 51

I-OMe-Tyrphostin AG 538

Structure of HIT compounds

AGK2

URAPIDIL HYDROCHLORIDE

Isoliquiritigenin

SEQUENCE LISTING

```
<160> NUMBER OF SEQ ID NOS: 15

<210> SEQ ID NO 1
<211> LENGTH: 239
<212> TYPE: PRT
<213> ORGANISM: Homo sapiens

<400> SEQUENCE: 1

Met Gln Asp Pro Asn Ala Asp Thr Glu Trp Asn Asp Ile Leu Arg Lys
1               5                   10                  15

Lys Gly Ile Leu Pro Pro Lys Glu Ser Leu Lys Glu Leu Glu Glu Glu
            20                  25                  30

Ala Glu Glu Glu Gln Arg Ile Leu Gln Gln Ser Val Val Lys Thr Tyr
        35                  40                  45

Glu Asp Met Thr Leu Glu Glu Leu Glu Asp His Glu Asp Glu Phe Asn
    50                  55                  60

Glu Glu Asp Glu Arg Ala Ile Glu Met Tyr Arg Arg Arg Leu Ala
65                  70                  75                  80

Glu Trp Lys Ala Thr Lys Leu Lys Asn Lys Phe Gly Glu Val Leu Glu
                85                  90                  95

Ile Ser Gly Lys Asp Tyr Val Gln Glu Val Thr Lys Ala Gly Glu Gly
            100                 105                 110

Leu Trp Val Ile Leu His Leu Tyr Lys Gln Gly Ile Pro Leu Cys Ala
        115                 120                 125

Leu Ile Asn Gln His Leu Ser Gly Leu Ala Arg Lys Phe Pro Asp Val
    130                 135                 140

Lys Phe Ile Lys Ala Ile Ser Thr Thr Cys Ile Pro Asn Tyr Pro Asp
145                 150                 155                 160

Arg Asn Leu Pro Thr Ile Phe Val Tyr Leu Glu Gly Asp Ile Lys Ala
                165                 170                 175

Gln Phe Ile Gly Pro Leu Val Phe Gly Gly Met Asn Leu Thr Arg Asp
            180                 185                 190

Glu Leu Glu Trp Lys Leu Ser Glu Ser Gly Ala Ile Met Thr Asp Leu
        195                 200                 205

Glu Glu Asn Pro Lys Lys Pro Ile Glu Asp Val Leu Leu Ser Ser Val
    210                 215                 220

Arg Arg Ser Val Leu Met Lys Arg Asp Ser Asp Ser Glu Gly Asp
225                 230                 235

<210> SEQ ID NO 2
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaaggctggg ctgggggaag aggcgtggcg gcgctgtgcg cgtgcacaaa agagagctga      60
ggggcggggg cgctgcggca cagctggttt gagcaactga actggaaaca agatgcagga     120
```

| | | | | | |
|---|---|---|---|---|---|
| ccccaacgca | gacactgaat | ggaatgacat | cttacgcaaa | aagggtatct | taccccccaa | 180
| ggaaagtctg | aaagaattgg | aagaggaggc | agaagaggag | cagcgcatcc | tccagcagtc | 240
| agtggtgaaa | acatatgaag | atatgacttt | ggaagagctg | gaggatcatg | aagacgagtt | 300
| taatgaggag | gatgaacgtg | ctattgaaat | gtacagacgg | cggagactgg | ctgagtggaa | 360
| agcaactaaa | ctgaagaata | aattcggaga | agttttggag | atctcaggga | aggattatgt | 420
| tcaagaagtt | accaaagctg | gcgagggctt | gtgggtcatc | ttgcacccttt | acaaacaagg | 480
| aattcccctc | tgtgccctga | taaatcagca | cctcagtgga | cttgccagga | agtttcctga | 540
| tgtcaaattt | atcaaagcca | tttcaacaac | ctgcataccc | aattatcctg | ataggaatct | 600
| gcccacgata | tttgtttacc | tggaaggaga | tatcaaggct | cagtttattg | gtcctctggt | 660
| gtttggcggc | atgaacctga | caagagatga | gttggaatgg | aaactgtctg | aatctggagc | 720
| aattatgaca | gacctggagg | aaaaccctaa | gaagccgatt | gaagacgtgt | tgctgtcctc | 780
| agtgcggcgc | tctgtcctca | tgaagaggga | cagcgattcc | gagggtgact | gaggctacag | 840
| cttctatcac | atgccgaact | tcttgtgac | aaattgtctg | gatttttaa | aaaaggaaaa | 900
| agcaagaatg | aatccttgtg | gttttagtt | ttgtataaat | tatgtttcaa | atctttacat | 960
| tttggaaata | atcattgctg | gagattctgt | taaatatttt | ggaactcttt | tttttttaa | 1020
| attatagtat | ttcctctaaa | aaaattaaa | accagccatt | tgtatggcaa | atgtcaaaaa | 1080
| aaaaaa | | | | | | 1086

```
<210> SEQ ID NO 3
<211> LENGTH: 240
<212> TYPE: PRT
<213> ORGANISM: Mus musculus

<400> SEQUENCE: 3
```

Met Gln Asp Pro Asn Ala Asp Thr Glu Trp Asn Asp Ile Leu Arg Lys
1               5                   10                  15

Lys Gly Ile Leu Pro Pro Lys Glu Ser Leu Lys Glu Leu Glu Glu Glu
                20                  25                  30

Glu Ala Glu Lys Glu Glu Gln Leu Leu Gln Gln Ser Val Val Lys Thr
            35                  40                  45

Tyr Glu Asp Met Thr Leu Glu Glu Leu Glu Glu Asn Glu Asp Glu Phe
        50                  55                  60

Ser Glu Glu Asp Glu Arg Ala Ile Glu Met Tyr Arg Gln Gln Arg Leu
65                  70                  75                  80

Ala Glu Trp Lys Ala Thr Gln Leu Lys Asn Lys Phe Gly Glu Val Leu
                85                  90                  95

Glu Ile Ser Gly Lys Asp Tyr Val Gln Glu Val Thr Lys Ala Gly Glu
                100                 105                 110

Gly Leu Trp Val Ile Leu His Leu Tyr Lys Gln Gly Ile Pro Leu Cys
            115                 120                 125

Ser Leu Ile Asn His His Leu Ser Gly Leu Ala Arg Lys Phe Pro Asp
        130                 135                 140

Val Lys Phe Ile Lys Ala Ile Ser Thr Thr Cys Ile Pro Asn Tyr Pro
145                 150                 155                 160

Asp Arg Asn Leu Pro Thr Val Phe Val Tyr Arg Glu Gly Asp Ile Lys
                165                 170                 175

Ala Gln Phe Ile Gly Pro Leu Val Phe Gly Gly Met Asn Leu Thr Ile
                180                 185                 190

-continued

Asp Glu Leu Glu Trp Lys Leu Ser Glu Ser Gly Ala Ile Lys Thr Ala
        195                 200                 205

Leu Glu Glu Asn Pro Lys Lys Pro Ile Gln Asp Leu Leu Leu Ser Ser
    210                 215                 220

Val Arg Gly Pro Val Pro Met Arg Arg Asp Ser Asp Ser Glu Asp Asp
225                 230                 235                 240

<210> SEQ ID NO 4
<211> LENGTH: 1706
<212> TYPE: DNA
<213> ORGANISM: Mus musculus

<400> SEQUENCE: 4

```
agagggctgg tttgagtgac tgaaggcaag atgcaggacc ccaatgcaga caccgagtgg      60
aatgacatcc tacgtaaaaa gggcatcctt cccccgaagg agagcctgaa ggagctggag     120
gaggaggagg cggagaagga ggagcagctc ctccagcagt cagtggtgaa aacatacgag     180
gacatgactc tggaagagct ggaggagaac gaggatgagt tcagtgagga ggatgaacga     240
gctatcgaga tgtaccggca acagaggttg gctgagtgga agcaactca gctgaagaac      300
aaatttggag aagttttaga gatctcagga aaggactatg ttcaagaagt tacgaaagcc     360
ggcgagggcc tgtgggtgat cttacacctg tacaaacaag ggattcccct ctgttccttg     420
ataaaccatc acttgagtgg actcgccagg aagtttcccg atgtgaaatt tatcaaagcc     480
atttcaacga cctgcatacc caactacccc gacaggaatc tccccacggt gttcgtctac     540
cgggaagggg atatcaaggc acagttcatt ggtcctctgg tgttcggtgg catgaacctg     600
accatagacg agttggagtg gaaactgtct gagtcaggag cgatcaagac agccctggag     660
gagaaccca agaagcccat ccaggacctg ctgctgtcct cagtccgggg ccctgtcccc      720
atgaggaggg acagtgattc tgaggacgac taagatggca gtgatggaac cttttgaacct     780
tcttgatatg acgcattgtc tgggtttttt ataaggaggg aaaagcaaaa tgtatcattt     840
tggttttaa ccttttttata attatttaaa ttttatacat ttcggatata atcattgctg      900
aactttttta agaaatttgt tggaactctt taattaatca tgtttcttta agagaaattt      960
aagcaagctt gttatgtcac atatctatgt tttcctatgt gtatttcagg aaaccatgaa    1020
actgttcagt attttttgac atgtaactct atagaaagga atgtggactt aaaaaatata    1080
atgcgaataa atttaagtta aaatctctat aaaaaataac agtgcaaaaa atgagaactc    1140
agctttctag ttagatcgtt cgttttcctt ttgtaaagct agcaaaagga gtatcagcta    1200
aaagaaatgg ctgataaattt tgagacagat actgatttat caaattagct gacagatttc    1260
agctcactgc catgtctgtt tgctttcagc ccagtcttcc aggtaaacta atgttctcta    1320
tggctgttaa gacaccagct attctttgta gtggcacatg cctttaatct cagcactggg    1380
agacaggggc aggcaggtca tgtgagatca aggccagtct ggtttgcata gttaccagct    1440
agccagggct gcgttaccaa gaccctgtct ccaaaccaag cagctcttct tggctgtaag    1500
gtcctgttag agttggtttg ggggaataag gtttaagcag atacatatat aagctctatc    1560
ccagtcgatt tgtaaaaata tttcaggata tcctgtaaag tgacaatgaa agccgaaaaa    1620
tatctataat attttttgttg aatgctatac cctgtatagc tgattggaat cttagagata    1680
agagtctaag aatacagggt ttactc                                          1706
```

<210> SEQ ID NO 5
<211> LENGTH: 240
<212> TYPE: PRT

<213> ORGANISM: Rattus norvegicus

<400> SEQUENCE: 5

| | | | | | | | | | | | | | | |
|---|---|---|---|---|---|---|---|---|---|---|---|---|---|---|
| Met | Gln | Asp | Pro | Asn | Ala | Asp | Thr | Glu | Trp | Asn | Asp | Ile | Leu | Arg | Lys |
| 1 | | | | 5 | | | | | 10 | | | | | 15 | |

Lys Gly Ile Leu Pro Pro Lys Glu Ser Leu Lys Glu Leu Glu Glu Glu
            20                    25                    30

Glu Glu Gly Lys Glu Glu Gln Arg Leu Gln Gln Ser Val Val Lys Thr
            35                    40                    45

Tyr Glu Asp Met Thr Leu Glu Glu Leu Gln Glu Asn Glu Asp Glu Phe
  50                    55                    60

Ser Glu Glu Asp Glu Arg Ala Ile Glu Met Tyr Arg Gln Gln Arg Leu
65                  70                    75                  80

Ala Glu Trp Lys Ala Thr Gln Leu Arg Asn Lys Phe Gly Glu Val Leu
            85                    90                    95

Glu Ile Ser Gly Lys Asp Tyr Val Gln Glu Val Thr Lys Ala Gly Glu
              100                  105                110

Gly Leu Trp Val Val Leu His Leu Tyr Lys Gln Gly Ile Pro Leu Cys
            115                  120                125

Ser Leu Ile Asn His His Leu Ser Gly Leu Ala Arg Lys Phe Pro Asp
  130                   135                  140

Val Lys Phe Ile Lys Ala Ile Ser Thr Thr Cys Ile Pro Asn Tyr Pro
145                  150                    155                  160

Asp Arg Asn Leu Pro Thr Val Phe Val Tyr Arg Glu Gly Asp Ile Lys
              165                  170                175

Ala Gln Phe Ile Gly Pro Leu Val Phe Gly Gly Met Asn Leu Thr Ile
            180                  185                190

Asp Glu Leu Glu Trp Lys Leu Ser Glu Ser Gly Ala Ile Lys Thr Glu
            195                  200                205

Leu Glu Glu Asn Pro Lys Lys Ala Ile Lys Asp Val Leu Leu Ser Ser
  210                   215                  220

Val Arg Asp Pro Val Pro Met Arg Arg Asp Ser Asp Ser Glu Asp Asp
225                  230                    235                  240

<210> SEQ ID NO 6
<211> LENGTH: 1784
<212> TYPE: DNA
<213> ORGANISM: Rattus norvegicus

<400> SEQUENCE: 6

| | | |
|---|---|---|
| ccgaagggc ggtgctacaa ggcgccagag gagcggaggc tggggcctag gggctggtcg | 60 |
| gaacttctgg aagcaagatg caggaccca acgcagacac cgagtggaat gacatccttc | 120 |
| gtaaaaaggg catccttccc cctaaggaga gcctgaagga gctggaggag gaggaggagg | 180 |
| aaaggagga gcagcgtctc cagcagtcag tggtgaagac atatgaagac atgaccctgg | 240 |
| aggagctgca ggagaacgaa gacgagttca gtgaggagga cgagcgagcc atcgagatgt | 300 |
| accggcagca aaggctggcc gagtggaagg cgactcagct gaggaacaag tttggagaag | 360 |
| ttttagagat ctcggggaag gattacgttc aagaagtcac caaggctggc gagggcttgt | 420 |
| gggtggtctt acacctgtac aaacaaggga ttcccctctg ttccttgata aaccatcact | 480 |
| tgagtgggct cgccaggaag tttcccgatg tgaaatttat caaagccatt tcaacgacct | 540 |
| gcatacccaa ttaccctgac aggaacctcc ccacagtgtt cgtctaccgg gagggggata | 600 |
| tcaaggcaca gttcatcggt cccctggtgt tcggtggcat gaacctgacc atagatgagt | 660 |

```
tggagtggaa actatctgag tcaggagcaa tcaagacaga gctggaggag aaccccaaga    720
aagccatcaa agacgtgctg ctgtcctcag tgcgggaccc tgtccccatg aggagggaca    780
gtgattccga ggacgactaa gatagcagtg atgcagcctt cgaactctc ttgataagac     840 gcattgtctg gagtttcaat aaggagggaa aagcaataat ttatccttt gggttttaac     900 cttttttataa ttatttaaat tttatacatt tcagatataa tcattgctga aattttttaa   960
gaaatttgtt ggaactcttt ataatgtttc tttaagaatt taagctctta tgtcacatat   1020
ccatgttttc ctacatgtgt ttcagcaaac cctgtgactg tttagtatct tttgacatgc   1080
aactatagag aaaggaatgt ggagtttaaa aacacaatgc aaataaatta agttaaaaac   1140
taaaacataa cagtgcagaa acaagaact cggctttata gttaagtcag actgtccatt    1200
ttcattttat aaagctagca aaagaaatat cagctgatag aaatggctga taattttgag   1260
acaaatactg tcttatcaaa ctagctgaca gatttcagct tacaccatgt ttgtattcag   1320
gtcagtcttc cagttaactc acgtgtgtct ctggctgtta agacaccagc tgttctttgt   1380
ggtggcacat gcttttaatc ccagcactgg gacacaggg ggcaggtcat gtgagttcaa    1440
ggctggtctg gcttgcaggg ccagggccac ctcaccaaga ccctgtcttg aagccaaaaa   1500
cagagctgtt cttggctcta aggtcctgtt aggttcggct tggggggactg aggtttaagc   1560 acacacacat gtaagctgtg tcccagctga tttataaaaa tgtttcggga tactctttga   1620
gtcagaatcc tataaattga tgatgaaagc tgaaaagtat caataatatt tttgttgaat   1680
gtggtaacat gtatagctga ttggaacctt agagataaga gtctaagaat acaggatttg   1740
ttcagaaaaa aaaaaaaaaa aaaaaaaaaa aaaaaaaaaa aaaa                   1784
```

<210> SEQ ID NO 7
<211> LENGTH: 1356
<212> TYPE: PRT
<213> ORGANISM: Homo sapiens

<400> SEQUENCE: 7

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175
```

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
            210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
            290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
            325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
            355                 360                 365

Ile Pro Leu Glu Ser Asn His Thr Ile Lys Ala Gly His Val Leu Thr
            370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
            405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
            565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr

-continued

```
            595                 600                 605
Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
                675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
                755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
                820                 825                 830

Arg Leu Lys Leu Gly Lys Pro Leu Gly Arg Gly Ala Phe Gly Gln Val
                835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
                915                 920                 925

Arg Ser Lys Arg Asn Glu Phe Val Pro Tyr Lys Thr Lys Gly Ala Arg
                930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
                980                 985                 990

Glu Asp Leu Tyr Lys Asp Phe Leu Thr Leu Glu His Leu Ile Cys Tyr
                995                 1000                1005

Ser Phe Gln Val Ala Lys Gly Met Glu Phe Leu Ala Ser Arg Lys
        1010                1015                1020
```

```
Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 8
<211> LENGTH: 6055
<212> TYPE: DNA
<213> ORGANISM: Homo sapiens

<400> SEQUENCE: 8
actgagtccc gggaccccgg gagagcggtc aatgtgtggt cgctgcgttt cctctgcctg      60
```

```
cgccgggcat cacttgcgcg ccgcagaaag tccgtctggc agcctggata tcctctccta      120
ccggcacccg cagacgcccc tgcagccgcg gtcggcgccc gggctcccta gccctgtgcg      180
ctcaactgtc ctgcgctgcg gggtgccgcg agttccacct ccgcgcctcc ttctctagac      240
aggcgctggg agaaagaacc ggctcccgag ttctgggcat ttcgcccggc tcgaggtgca      300
ggatgcagag caaggtgctg ctggccgtcg ccctgtggct ctgcgtggag acccgggccg      360
cctctgtggg tttgcctagt gtttctcttg atctgcccag gctcagcata caaaaagaca      420
tacttacaat taaggctaat acaactcttc aaattacttg caggggacag agggacttgg      480
actggctttg gcccaataat cagagtggca gtgagcaaag ggtggaggtg actgagtgca      540
gcgatggcct cttctgtaag acactcacaa ttccaaaagt gatcggaaat gacactggag      600
cctacaagtg cttctaccgg gaaactgact tggcctcggt catttatgtc tatgttcaag      660
attacagatc tccatttatt gcttctgtta gtgaccaaca tggagtcgtg tacattactg      720
agaacaaaaa caaactgtg gtgattccat gtctcgggtc catttcaaat ctcaacgtgt      780
cactttgtgc aagataccca gaaaagagat tgttcctga tggtaacaga atttcctggg      840
acagcaagaa gggctttact attcccagct acatgatcag ctatgctggc atggtcttct      900
gtgaagcaaa aattaatgat gaaagttacc agtctattat gtacatagtt gtcgttgtag      960
ggtataggat ttatgatgtg ttctgagtc cgtctcatgg aattgaacta tctgttggag     1020
aaaagcttgt cttaaattgt acagcaagaa ctgaactaaa tgtggggatt gacttcaact     1080
gggaataccc ttcttcgaag catcagcata agaaacttgt aaaccgagac ctaaaaaccc     1140
agtctgggag tgagatgaag aaatttttga gcaccttaac tatagatggt gtaacccgga     1200
gtgaccaagg attgtacacc tgtgcagcat ccagtgggct gatgaccaag aagaacagca     1260
catttgtcag ggtccatgaa aaacctttg ttgcttttgg aagtggcatg gaatctctgg     1320
tggaagccac ggtgggggag cgtgtcagaa tccctgcgaa gtaccttggt tacccacccc     1380
cagaaataaa atggtataaa aatggaatac cccttgagtc caatcacaca attaaagcgg     1440
ggcatgtact gacgattatg gaagtgagtg aaagagacac aggaaattac actgtcatcc     1500
ttaccaatcc catttcaaag gagaagcaga gccatgtggt ctctctggtt gtgtatgtcc     1560
caccccagat tggtgagaaa tctctaatct ctcctgtgga ttcctaccag tacggcacca     1620
ctcaaacgct gacatgtacg gtctatgcca ttcctccccc gcatcacatc cactggtatt     1680
ggcagttgga ggaagagtgc gccaacgagc ccagccaagc tgtctcagtg acaaacccat     1740
acccttgtga agaatggaga agtgtggagg acttccaggg aggaaataaa attgaagtta     1800
ataaaaatca atttgctcta attgaaggaa aaaacaaaac tgtaagtacc cttgttatcc     1860
aagcggcaaa tgtgtcagct ttgtacaaat gtgaagcggt caacaaagtc gggagaggag     1920
agagggtgat ctccttccac gtgaccaggg gtcctgaaat tactttgcaa cctgacatgc     1980
agcccactga gcaggagagc gtgtctttgt ggtgcactgc agacagatct acgtttgaga     2040
acctcacatg gtacaagctt ggcccacagc ctctgccaat ccatgtggga gagttgccca     2100
cacctgtttg caagaacttg gatactcttt ggaaattgaa tgccaccatg ttctctaata     2160
gcacaaatga cattttgatc atggagctta agaatgcatc cttgcaggac caaggagact     2220
atgtctgcct tgctcaagac aggaagacca agaaaagaca ttgcgtggtc aggcagctca     2280
cagtcctaga gcgtgtggca cccacgatca caggaaacct ggagaatcag acgacaagta     2340
ttggggaaag catcgaagtc tcatgcacgg catctgggaa tccccctcca cagatcatgt     2400
```

```
ggtttaaaga taatgagacc cttgtagaag actcaggcat tgtattgaag gatgggaacc    2460
ggaacctcac tatccgcaga gtgaggaagg aggacgaagg cctctacacc tgccaggcat    2520
gcagtgttct tggctgtgca aaagtggagg cattttttcat aatagaaggt gcccaggaaa   2580
agacgaactt ggaaatcatt attctagtag gcacggcggt gattgccatg ttcttctggc   2640
tacttcttgt catcatccta cggaccgtta agcgggccaa tggagggaa ctgaagacag     2700 gctacttgtc catcgtcatg gatccagatg aactcccatt ggatgaacat tgtgaacgac    2760
tgccttatga tgccagcaaa tgggaattcc ccagagaccg gctgaagcta ggtaagcctc    2820
ttggccgtgg tgcctttggc caagtgattg aagcagatgc ctttggaatt gacaagacag    2880
caacttgcag gacagtagca gtcaaaatgt tgaaagaagg agcaacacac agtgagcatc    2940
gagctctcat gtctgaactc aagatcctca ttcatattgg tcaccatctc aatgtggtca    3000
accttctagg tgcctgtacc aagccaggag ggccactcat ggtgattgtg gaattctgca    3060
aatttggaaa cctgtccact tacctgagga gcaagagaaa tgaatttgtc ccctacaaga    3120
ccaaaggggc acgattccgt caaggaaaag actacgttgg agcaatccct gtggatctga    3180
aacggcgctt ggacagcatc accagtagcc agagctcagc cagctctgga tttgtggagg    3240
agaagtccct cagtgatgta gaagaagagg aagctcctga agatctgtat aaggacttcc    3300
tgaccttgga gcatctcatc tgttacagct ccaagtggc taagggcatg gagttcttgg     3360
catcgcgaaa gtgtatccac agggacctgg cggcacgaaa tatcctctta cggagaaga    3420 acgtggttaa aatctgtgac tttggcttgg cccgggatat ttataaagat ccagattatg    3480
tcagaaaagg agatgctcgc ctcccttga aatggatggc cccagaaaca atttttgaca     3540
gagtgtacac aatccagagt gacgtctggt cttttggtgt tttgctgtgg gaaatatttt    3600
ccttaggtgc ttctccatat cctggggtaa agattgatga agaattttgt aggcgattga    3660
aagaaggaac tagaatgagg gcccctgatt atactacacc agaaatgtac cagaccatgc    3720
tggactgctg gcacggggag cccagtcaga gacccacgtt ttcagagttg gtggaacatt    3780
tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
tcagtcagta tctgcagaac agtaagcgaa agagccggcc tgtgagtgta aaaacatttg    4020
aagatatccc gttagaagaa ccagaagtaa aagtaatccc agatgacaac cagacggaca    4080
gtggtatggt tcttgcctca gaagagctga aaactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
ccagtgagga agcagaactt ttaaagctga tagagattgg agtgcaaacc ggtagcacag    4320
cccagattct ccagcctgac tcggggacca cactgagctc tcctcctgtt taaaaggaag    4380
catccacacc cccaactcct ggacatcaca tgagaggtgc tgctcagatt ttcaagtgtt    4440
gttctttcca ccagcaggaa gtagccgcat ttgatttcca tttcgacaac agaaaaagga    4500
cctcggactg cagggagcca gtcttctagg catatcctgg aagaggcttg tgacccaaga    4560
atgtgtctgt gtcttctccc agtgttgacc tgatcctctt tttcattcat ttaaaaagca    4620
tttatcatgc cccctgctgc gggtctcacc atgggtttag aacaaagacg ttcaagaaat    4680
ggccccatcc tcaaagaagt agcagtacct ggggagctga cacttctgta aaactagaag    4740
ataaaccagg caatgtaagt gttcgaggtg ttgaagatgg gaaggatttg cagggctgag    4800
```

```
tctatccaag aggctttgtt taggacgtgg gtcccaagcc aagccttaag tgtggaattc    4860
ggattgatag aaaggaagac taacgttacc ttgctttgga gagtactgga gcctgcaaat    4920
gcattgtgtt tgctctggtg gaggtgggca tggggtctgt tctgaaatgt aaagggttca    4980
gacgggtttt ctggttttag aaggttgcgt gttcttcgag ttgggctaaa gtagagttcg    5040
ttgtgctgtt tctgactcct aatgagagtt ccttccagac cgttacgtgt ctcctggcca    5100
agccccagga aggaaatgat gcagctctgg ctccttgtct cccaggctga tcctttattc    5160
agaataccac aaagaaagga cattcagctc aaggctccct gccgtgttga agagttctga    5220
ctgcacaaac cagcttctgg tttcttctgg aatgaatacc ctcatatctg tcctgatgtg    5280
atatgtctga gactgaatgc gggaggttca atgtgaagct gtgtgtggtg tcaaagtttc    5340
aggaaggatt ttacccttttt gttcttcccc ctgtccccaa cccactctca ccccgcaacc    5400
catcagtatt ttagttattt ggcctctact ccagtaaacc tgattgggtt tgttcactct    5460
ctgaatgatt attagccaga cttcaaaatt attttatagc ccaaattata acatctattg    5520
tattatttag acttttaaca tatagagcta tttctactga ttttttgccct tgttctgtcc    5580 tttttttcaa aaaagaaaat gtgttttttg tttggtacca tagtgtgaaa tgctgggaac    5640
aatgactata agacatgcta tggcacatat atttatagtc tgtttatgta gaaacaaatg    5700
taatatatta aagccttata tataatgaac tttgtactat tcacattttg tatcagtatt    5760
atgtagcata acaaaggtca taatgctttc agcaattgat gtcattttat taaagaacat    5820
tgaaaaactt gaaggaatcc ctttgcaagg ttgcattact gtaccatca tttctaaaat    5880 ggaagagggg gtggctgggc acagtggccg acacctaaaa acccagcact ttggggggcc    5940
aaggtgggag gatcgcttga gcccaggagt tcaagaccag tctggccaac atggtcagat    6000
tccatctcaa agaaaaaagg taaaaataaa ataaaatgga gaagaaggaa tcaga          6055

<210> SEQ ID NO 9
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gln Asp Pro Asn Ala Asp Thr Glu Trp Asn Asp Ile Leu Arg Lys
1               5                   10                  15

Lys Gly Ile Leu Pro Pro Lys Glu Ser Leu Lys Glu Leu Glu Glu Glu
            20                  25                  30

Ala Glu Glu Gln Arg Ile Leu Gln Gln Ser Val Val Lys Thr Tyr
        35                  40                  45

Glu Asp
    50

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cggtgtctgc gtttgggtcc tgcat                                            25
```

```
<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 11
aannnnnnnn nnnnnnnnnn ntt                                            23

<210> SEQ ID NO 12
<211> LENGTH: 4
<212> TYPE: PRT
<213> ORGANISM: Unknown
<220> FEATURE:
<223> OTHER INFORMATION: Description of Unknown:
      'KDEL' family peptide motif sequence

<400> SEQUENCE: 12

Lys Asp Glu Leu
1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Gln Asp Pro Asn Ala Asp Thr Glu Trp Asn Asp Ile Leu Arg
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-amino acid

<400> SEQUENCE: 15

Arg Arg Lys Arg Arg Arg
1               5
```

THERAPEUTIC AND RESEARCH APPLICATION OF PDCL3

CROSS-REFERENCE TO RELATED APPLICATIONS

This application is a National Phase Entry Application under 35 U.S.C. § 371 of International Application No. PCT/US2015/050108 filed Sep. 15, 2015, which claims benefit under 35 U.S.C. § 119(e) of U.S. Provisional No. 62/050,375, filed Sep. 15, 2014, the contents of each of which are herein incorporated by reference in their entireties.

GOVERNMENT SUPPORT

This invention was made with Government Support under Contract No. EY017955 awarded by the National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Oct. 4, 2018, is named 701586-082552-US_SL.txt and is 34,772 bytes in size.

FIELD OF THE INVENTION

This invention relates to PDCL3 and compositions and methods for inhibition of pathological angiogenesis, increasing angiogenesis, and promoting protein production.

BACKGROUND

Angiogenesis, the formation of new blood vessels, plays a central role in embryonic development, wound healing, tumor growth, and neovascular ocular diseases. Proteins that promote angiogenesis play central roles in the onset and progression of tumor progression and ocular neovascularization and retinopathies. The expression of unique blends of proteins in endothelial cells with pro- and anti-angiogenesis functions regulates angiogenesis and disruption in the activity or expression of these proteins so called "angiogenic switch" is responsible for pathological angiogenesis[1-3]. To maintain normal angiogenesis endothelial cells must possess mechanisms to control homeostasis or proteostasis of pro- and anti-angiogenesis proteins.

The research directed toward understanding the molecular mechanisms of angiogenesis and systematically characterizing vascular endothelial growth factor (VEGF) and signaling of its key receptor tyrosine kinase, VEGFR-2, also called kinase insert domain receptor (KDR) or fetal liver kinase 1 (FLK-1), in pre-clinical and clinical settings has provided substantial mechanistic insight into pathological angiogenesis[4,5]. In general, the balance between endogenous pro-angiogenic and anti-angiogenic factors controls angiogenesis, such that endothelial cell growth is normally restrained. However, in pathologic angiogenesis, a shift occurs in the balance of regulators where expression and or activation of pro-angiogenic factors such as VEGF and its canonical receptors are significantly upregulated, which subsequently results in exorbitant angiogenesis[9-11].

VEGFR-2 is an essential mediator of VEGF-initiated angiogenesis and plays a pivotal role in regulating multiple signaling pathways in endothelial cells that modulates the core angiogenic responses such as proliferation, migration and capillary tube formation[6,12]. VEGF-induced posttranslational modifications (PTMs) on VEGFR-2 such as tyrosine and serine/threonine phosphorylation, ubiquitination, and methylation confer VEGFR-2 as a multi-potent regulator of angiogenesis. These PTMs subsequently arbitrate the outcome of angiogenic signaling and homoeostasis of mature VEGFR-2 protein in endothelial cells[1,13]. The abundance of mature cell surface VEGFR-2 protein is primarily regulated by mechanism that involves both increase in stabilization and destabilization of VEGFR-2. For example, VEGF-induced association of VEGFR-2 with protein βTrcp ubiquitin E3 ligase destabilizes VEGFR-2[14] whereas its association with Ephrin-B2 and vascular endothelial cadherin inhibits its internalization[15,16] In some circumstances its interaction with cerebral cavernous malformation 3 (CCM3) and Hsp90 stabilizes the membrane bound cell surface VEGFR-2[17,18].

SUMMARY OF THE INVENTION

Provided herein are novel compositions comprising, for example, PDCL3 polypeptides having VEGFR-2 inhibitory activity, inhibitory PDCL3 antibodies and PDCL3-binding fragments thereof, or PDCL3 inhibitory nucleic acid molecules, and methods of their use in anti-angiogenesis and anti-tumor proliferation and invasiveness therapies, such as the treatment of cancer, as well as the treatment of those vascular diseases where pathological angiogenesis plays a role, such as in carotid artery disease, macular degeneration, and plaque neovascularization.

Also provided herein are novel compositions comprising engineered PDCL3 polypeptides having enhanced chaperone activity, recombinant cells comprising such engineered PDCL3 polypeptides having enhanced chaperone activity, and methods thereof for therapeutic protein production and in vitro protein synthesis.

As described herein, the inventors have identified a novel function for PDCL3 (phosducin-like 3) in the stabilization of VEGFR-2, and discovered that PDCL3 acts as a VEGFR-2 chaperone protein, thereby stabilizing VEGFR-2. PDCL3 co-localizes with VEGFR-2 in cells and recognizes the juxtamembrane domain of VEGFR-2. Over-expression of PDCL3 increases the abundance of VEGFR-2 protein, whereas silencing of PDCL3 expression by siRNA in endothelial cells significantly reduces VEGFR-2 protein, as demonstrated herein. Moreover, as demonstrated herein, PDCL3 activity is required for endothelial cell proliferation and capillary tube formation of primary endothelial cells and angiogenesis in developing zebrafish embryos. PDCL3 exhibits its activity on endothelial cell proliferation and angiogenesis, in part, by rendering VEGFR-2 a more stable protein and preventing its ubiquitylation and proteolytic degradation. Taken together, the data provided herein demonstrate that PDCL3 associates with VEGFR-2 and control its function, and with it angiogenesis and angiogenesis-mediated disorders.

Accordingly, provided herein are PDCL3 antagonist agents, such as a PDCL3 antagonist polypeptide, PDCL3-specific inhibitory nucleic acid, PDCL3 antagonist antibody or antigen-binding fragment thereof, or PDCL3 specific small molecule that inhibits or causes or facilitates a qualitative or quantitative inhibition, decrease, or reduction in one or more processes, mechanisms, effects, responses, functions, activities or pathways mediated by PDCL3, and methods comprising such PDCL3 antagonist agents.

In some aspects, provided herein are isolated PDCL3 antagonist polypeptides. These PDCL3 antagonist polypeptide bind VEGFR-2 intracellularly in a manner that inhibits binding of VEGFR-2 to endogenous PDCL3, thereby preventing PDCL3 acting as a chaperone and stabilizing VEGFR-2. In some embodiments of these aspects and all such aspects described herein, the PDCL3 antagonist polypeptide comprises a domain that specifically binds to VEGFR-2 and prevents binding of VEGFR-2 to endogenous PDCL3. In some embodiments of these aspects and all such aspects described herein, the PDCL3 antagonist polypeptide comprises a PDCL3 coil-coil domain. In some embodiments of these aspects and all such aspects described herein, the PDCL3 antagonist polypeptide further comprises a PDCL3 thioredoxin domain. In some embodiments of these aspects and all such aspects described herein, the PDCL3 antagonist polypeptide further comprises a PDCL3 C-terminal domain.

In some embodiments of these aspects and all such aspects described herein, the PDCL3 antagonist polypeptide comprises a coiled-coiled domain having the amino acid sequence of SEQ ID NO: 9 or a portion, fragment, or derivative thereof of SEQ ID NO: 9, that inhibits or reduces VEGFR-2 mediated activity.

In some aspects, provided herein are pharmaceutical compositions comprising isolated PDCL3 antagonist polypeptides that bind VEGFR-2 intracellularly in a manner that inhibits binding of VEGFR-2 to endogenous PDCL3, thereby preventing PDCL3 acting as a chaperone and stabilizing VEGFR-2, and a pharmaceutically acceptable carrier.

In some embodiments of these aspects and all such aspects described herein, the PDCL3 antagonist polypeptide comprises a domain that specifically binds to VEGFR-2 and prevents binding of VEGFR-2 to endogenous PDCL3. In some embodiments of these aspects and all such aspects described herein, the PDCL3 antagonist polypeptide comprises a PDCL3 coil-coil domain. In some embodiments of these aspects and all such aspects described herein, the PDCL3 antagonist polypeptide further comprises a PDCL3 thioredoxin domain. In some embodiments of these aspects and all such aspects described herein, the PDCL3 antagonist polypeptide further comprises a PDCL3 C-terminal domain.

In some embodiments of these aspects and all such aspects described herein, the PDCL3 antagonist polypeptide comprises a coiled-coiled domain having the amino acid sequence of SEQ ID NO: 9 or a portion, fragment, or derivative thereof of SEQ ID NO: 9, that inhibits or reduces VEGFR-2 mediated activity.

In other aspects, provided herein are PDCL3-specific RNA interference agents that specifically target PDCL3 and can be used for the inhibition of expression of PDCL3. In some embodiments of the aspects and all such aspects described herein, the RNA interference agent or siRNA is a PDCL3-specific double stranded RNA (dsRNA). In some embodiments of the aspects and all such aspects described herein, the RNA interference agent or siRNA is a PDCL3-specific small hairpin RNA (shRNA).

Also provided herein, in some aspects, are PDCL3 antagonist antibodies or antibody fragments thereof that are specific for PDCL3, where the PDCL3 antagonist antibodies or antibody fragments thereof specifically bind to PDCL3 and reduce or inhibit PDCL3 biological activity, such as the VEGFR-2 stabilizing activity of PDCL3. In some embodiments of these aspects and all such aspects described herein, PDCL3 is human PDCL3. In some embodiments of these aspects and all such aspects described herein, the PDCL3 antagonist antibody binds PDCL3 and inhibits the ability of PDCL3 to bind or associate with VEGFR-2. In some such embodiments, the VEGFR-2 has a sequence comprising the sequence of SEQ ID NO: 7. In some embodiments of these aspects and all such aspects described herein, the PDCL3 antagonist antibodies completely inhibit the biological activity of PDCL3. In some embodiments of these aspects and all such aspects described herein, the PDCL3 antagonist antibody or antibody fragment thereof is specific for an epitope of PDCL3 comprising a coil-coil domain portion of PDCL3, such as, for example, SEQ ID NO: 9.

In other aspects, provided herein, are small molecule antagonists of PDCL3 or agents that specifically target PDCL3 and can be used for the inhibition of expression or activity of PDCL3 in vivo for inhibiting VEGFR-2 activity and/or pathological angiogenesis. In some embodiments of these aspects and all such aspects described herein, a small molecule antagonist of PDCL3 selectively binds to PDCL3. In some embodiments of the aspects described herein, the small molecule antagonist or agent that specifically targets or inhibits PDCL3 is selected from the group consisting of Reserpine, DAPH, AC-93253 iodide, Emodin, Sunitinib malate, GW2974, Urapidil Hydrochloride, Mecamylamine hydrochloride, (−)-MK-801 hydrogen maleate, AGK2, Tyrphostin AG 112, Tyrphostin 23, Tyrphostin 51, I-Ome-Tyrophostin AG 538, and Isoliquiritgenin.

Also provided herein, in some aspects, are methods of inhibiting VEGFR-2 activity in a subject having a disease or disorder dependent on VEGFR-2 activity. Such methods of inhibiting VEGFR-2 activity comprise administering to a subject having a disease or disorder dependent on VEGFR-2 activity a therapeutically effective amount of a pharmaceutical composition comprising a PDCL3 antagonist agent, as described herein.

In some aspects, provided herein are methods of inhibiting angiogenesis in a subject having a disease or disorder dependent or modulated by angiogenesis. Such methods of inhibiting angiogenesis comprising administering to a subject having a disease or disorder dependent or modulated by angiogenesis a therapeutically effective amount of a pharmaceutical composition comprising a PDCL3 antagonist agent, as described herein.

In some embodiments of these methods and all such methods described herein, the PDCL3 antagonist agent being administered is a PDCL3 antagonist polypeptide. In some such embodiments, the PDCL3 antagonist polypeptide binds VEGFR-2 intracellularly in a manner that inhibits binding of VEGFR-2 to endogenous PDCL3, thereby preventing PDCL3 acting as a chaperone and stabilizing VEGFR-2. In some such embodiments, the PDCL3 antagonist polypeptide comprises a domain that specifically binds to VEGFR-2 and prevents binding of VEGFR-2 to endogenous PDCL3. In some such embodiments, the PDCL3 antagonist polypeptide comprises a PDCL3 coil-coil domain. In some such embodiments, the PDCL3 antagonist polypeptide further comprises a PDCL3 thioredoxin domain. In some such embodiments, the PDCL3 antagonist polypeptide further comprises a PDCL3 C-terminal domain. In some such embodiments, the PDCL3 antagonist polypeptide comprises a coiled-coiled domain having the amino acid sequence of SEQ ID NO: 9 or a portion, fragment, or derivative thereof of SEQ ID NO: 9, that inhibits or reduces VEGFR-2 mediated activity.

In some embodiments of these methods and all such methods described herein, the PDCL3 antagonist agent being administered is a PDCL3-specific RNA interference agent. In some such embodiments, the PDCL3-specific RNA interference agent is an shRNA or dsRNA specific for PDCL3.

In some embodiments of these methods and all such methods described herein, the PDCL3 antagonist agent being administered is a PDCL3 antagonist antibody or antigen-binding fragment thereof. In some embodiments, the PDCL3 antagonist antibody or antigen-binding fragment thereof blocks interaction of PDCL3 with VEGFR-2. In some embodiments, the PDCL3 antagonist antibody or antibody fragment thereof is specific for an epitope of PDCL3 comprising a coil-coil domain portion of PDCL3. In some such embodiments, the epitope of PDCL3 comprising a coil-coil domain portion of PDCL3 comprises the sequence of SEQ ID NO: 9 that inhibits endogenous PDCL3 binding to VEGFR-2 and reduces or inhibits VEGFR-2 mediated activity. In some embodiments, the antibody fragment is a Fab fragment, a Fab' fragment, a Fd fragment, a Fd' fragment, a Fv fragment, a dAb fragment, a F(ab')$_2$ fragment, a single chain fragment, a diabody, or a linear antibody.

In some embodiments of these methods and all such methods described herein, the PDCL3 antagonist agent being administered is a small molecule PDCL3 antagonist agent. In some embodiments, the small molecule PDCL3 antagonist agent is selected from the group consisting of Reserpine, DAPH, AC-93253 iodide, Emodin, Sunitinib malate, GW2974, Urapidil Hydrochloride, Mecamylamine hydrochloride, (−)-MK-801 hydrogen maleate, AGK2, Tyrphostin AG 112, Tyrphostin 23, Tyrphostin 51, I-Ome-Tyrophostin AG 538, and Isoliquiritgenin.

In some embodiments of these methods and all such methods described herein, the disease or disorder dependent on VEGFR-2 activity, or dependent or modulated by angiogenesis, is a cancer or a tumor.

In some embodiments of these methods and all such methods described herein, the disease or disorder dependent on VEGFR-2 activity, or dependent or modulated by angiogenesis, is selected from the group consisting of age-related macular degeneration, carotid artery disease, diabetic retinopathy, rheumatoid arthritis, neurodegenerative disorder, Alzheimer's disease, obesity, endometriosis, psoriasis, artherosclerosis, ocular neovascularization, neovascular glaucoma, osteoporsosis, and restenosis.

In some embodiments of these methods and all such methods described herein, the method further comprises the administration of one or more chemotherapeutic agents, angiogenesis inhibitors, cytotoxic agents, and anti-proliferative agents.

In addition, as described herein, the inventors have discovered that preventing N-terminal acetylation of PDCL3 potently increases PDCL3 chaperone protein activity. Previously, PDCL3 was described as a cytoplasmic protein, and we demonstrate herein that PDCL3 is present at both the endoplasmic reticulum (ER) and cytoplasmic compartments. Consistent with the chaperone function of PDCL3, ER-localized PDCL3 associates with newly synthesized VEGFR-2 where it protects VEGFR-2 from degradation. Our data demonstrate that N-terminal methionine acetylation regulates stability of PDCL3. PDCL3 stability appears to play an important role in angiogenesis, as its expression was upregulated by hypoxia, a master regulator of angiogenesis. Furthermore, zebrafish experiments confirmed its biological importance to angiogenesis. Over-expression of an engineered PDCL3 unable to undergo N-terminal acetylation was significantly more potent than the wild type PDCL3 in its ability to stimulate angiogenesis in endothelial cells. Thus, engineered PDCL3 polypeptides are useful in compositions and methods for enhanced expression and production of recombinant proteins and in vitro protein synthesis.

Accordingly, provided herein, in some aspects, are novel compositions comprising engineered PDCL3 polypeptides having enhanced chaperone activity, recombinant cells comprising such engineered PDCL3 polypeptides having enhanced chaperone activity, and methods thereof for therapeutic protein production and in vitro protein synthesis.

In some aspects, provided herein are engineered PDCL3 polypeptides having enhanced chaperone activity, and nucleic acids encoding such engineered PDCL3 polypeptides. These engineered PDCL3 polypeptides are unable to undergo N-terminal acetylation thereby stabilizing PDCL3 and enhancing PDCL3 chaperone activity.

In some embodiments of these aspects and all such aspects described herein, the engineered PDCL3 is acetylation resistant. In some embodiments of these aspects and all such aspects described herein, the engineered PDCL3 comprises a modification at the N-terminal methionine. In some embodiments of these aspects and all such aspects described herein, the modification at the N-terminal methionine is an acetylation-resistant N-terminal methionine. In some embodiments of these aspects and all such aspects described herein, the modification at the N-terminal methionine is insertion of a tag prior to or at the N-terminal methionine.

Provided herein, in some aspects, are recombinant cells for enhancing expression of a recombinant protein product comprising a host cell comprising a nucleic acid sequence encoding an engineered PDCL3 polypeptide. In some embodiments of these aspects and all such aspects described herein, the host cell further comprises a nucleic acid sequence encoding a recombinant protein of interest.

In some aspects, provided herein are recombinant cells for enhancing expression of a recombinant protein product comprising a host cell comprising: a nucleic acid sequence encoding an engineered PDCL3 polypeptide and a nucleic acid sequence encoding a recombinant protein of interest.

In some embodiments of these aspects and all such aspects described herein, the engineered PDCL3 comprises a modification at the N-terminal methionine. In some embodiments of these aspects and all such aspects described herein, the modification at the N-terminal methionine is an acetylation-resistant N-terminal methionine. In some embodiments of these aspects and all such aspects described herein, the modification at the N-terminal methionine is insertion of a tag prior to or at the N-terminal methionine.

In some embodiments of these aspects and all such aspects described herein, the host cell is a mammalian host cell. In some embodiments of these aspects and all such aspects described herein, the mammalian host cell is a human cell. In some embodiments of these aspects and all such aspects described herein, the mammalian host cell is a CHO (Chinese Hamster Ovary) cell. In some embodiments of these aspects and all such aspects described herein, the host cell is stably transformed with the nucleic acid sequence encoding the engineered PDCL3 polypeptide. In some embodiments of these aspects and all such aspects described herein, the host cell is stably transformed with the nucleic acid sequence encoding the recombinant protein of interest.

In other aspects, provided herein are methods for increasing protein production or for in vitro protein production comprising introducing into a host cell a nucleic acid sequence encoding an engineered PDCL3 polypeptide and a nucleic acid sequence encoding a recombinant protein of interest, thereby generating a recombinant cell for increasing production of the recombinant protein of interest, wherein the recombinant cell has increased production of the recombinant protein of interest relative to a cell in which the nucleic acid sequence encoding the engineered PDCL3 polypeptide was not introduced.

In some aspects, provided herein are methods for producing a host cell for enhanced expression of a recombinant protein of interest comprising: providing a host cell having a nucleic acid sequence encoding for expression of a target recombinant protein; and transforming the mammalian cell with at least one expression vector comprising a nucleic acid sequence encoding an engineered PDCL3 polypeptide.

In some aspects, provided herein are methods for increasing production of a recombinant protein of interest comprising culturing a host cell, wherein the host cell comprises a nucleic acid sequence encoding a recombinant protein of interest and further introducing into said cell at least one nucleic acid sequence encoding an engineered PDCL3 polypeptide; and recovering the recombinant protein of interest produced by the cell.

In some embodiments of these methods and all such methods described herein, the engineered PDCL3 comprises a modification at the N-terminal methionine. In some embodiments of these methods and all such methods described herein, the modification at the N-terminal methionine is an acetylation-resistant N-terminal methionine. In some embodiments of these methods and all such methods described herein, the modification at the N-terminal methionine is insertion of a tag prior to or at the N-terminal methionine.

In some embodiments of these methods and all such methods described herein, the host cell is a mammalian host cell, such as a human cell or a CHO (Chinese Hamster Ovary) cell. In some embodiments of these methods and all such methods described herein, the host cell is stably transformed with the nucleic acid sequence encoding the engineered PDCL3 polypeptide. In some embodiments of these methods and all such methods described herein, the host cell is stably transformed with the nucleic acid sequence encoding the recombinant protein of interest.

In some embodiments of these methods and all such methods described herein, the nucleic acid sequence encoding the recombinant protein of interest and/or the nucleic acid sequence encoding the engineered PDCL3 polypeptide are introduced into the cell in one or more expression vectors.

In some embodiments of these methods and all such methods described herein, the nucleic acid sequence encoding the recombinant protein of interest and/or the nucleic acid sequence encoding the engineered PDCL3 polypeptide are introduced into the cell via transfection.

In some embodiments of these methods and all such methods described herein, the host cell is stably transformed with the nucleic acid sequence encoding the recombinant protein of interest.

In some embodiments of these methods and all such methods described herein, the host cell is stably transformed with the nucleic acid sequence encoding the engineered PDCL3 polypeptide.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "PDCL3" or "PhLP3" as used herein, refers to the 239-amino acid human phosducin-like protein 3 (PDCL3) having the amino acid sequence of SEQ ID NO: 1, as described by, e.g., NP_076970.1, and encoded by, e.g., the sequence of NM_024065.4 (SEQ ID NO: 2), together with naturally occurring allelic, splice variants, and processed forms thereof. Other forms of PDCL3 encompassed by the term "PDCL3," include, for example, mouse PDCL3, as described by, e.g., NP_081126.2 (SEQ ID NO: 3), and encoded by the sequence of NM_026850.4 (SEQ ID NO: 4); and rat PDCL3, as described by, e.g., NP_001020880.1 (SEQ ID NO: 5), and encoded by the sequence of NM_001025709.1 (SEQ ID NO: 6). Typically, PDCL3 refers to human PDCL3. The term "PDCL3" is also used to refer to truncated forms or fragments of the polypeptide comprising specific amino acids sequences of the 239-amino acid human PDCL3, such as those having VEGFR-2 inhibitory activity, as provided herein. Reference to any such forms of PDCL3 can be identified in the application, e.g., by "PDCL3 (1-50)." PDCL3 comprises an N-terminal helical or "coil-coil" domain, a central thioredoxin-like domain, and a charged carboxyl terminus (Blaauw et al., 2003).

The terms "VEGFR-2" or "KDR," as used herein, refers to the 1356 amino acid polypeptide having the amino acid sequence of: SEQ ID NO: 7, as described by, e.g., NP_002244.1, and encoded by, e.g., NM_002253.2 (SEQ ID NO: 8), together with any naturally occurring allelic, splice variants, and processed forms thereof. Typically, VEGFR-2 refers to human VEGFR-2. The terms "VEGFR-2" or "KDR" are also used to refer to truncated forms or fragments of the VEGFR-2 polypeptide. Reference to any such forms or fragments of VEGFR-2 can be identified in the application, e.g., by "VEGFR-2 (1-1204), or "VEGFR-2Δ152" Specific residues of VEGFR-2 can be referred to as, for example, "VEGFR-2 (62)."

A PDCL3 "VEGFR-2 binding site," as used herein, refers to a PDCL3 amino acid sequence to which VEGFR-2 binds or associates. VEGFR-2 associates with PDCL3 via its juxtamembrane domain. By preventing association of VEGFR-2 to PDCL3 using a PDCL3 antagonist agent, as described herein, VEGFR-2 is not stabilized and undergoes ubiquitin-mediated degradation, and therefore VEGFR-2 mediated signaling and angiogenesis is inhibited. Accordingly, in some embodiments, a PDCL3 antagonist agent prevents the association between the VEGFR-2 juxtamembrane domain and the PDCL3 VEGFR-2 binding site.

As used herein, a "PDCL3 antagonist agent" or "PDCL3 antagonist" refer to an agent, such as a small molecule, antagonist polypeptide, inhibitory nucleic acid, or PDCL3 antibody or antigen-binding fragment thereof, that inhibits or causes or facilitates a qualitative or quantitative inhibition, decrease, or reduction in one or more processes, mechanisms, effects, responses, functions, activities or pathways mediated by PDCL3. Thus, the term PDCL3 antagonist agent refers to an agent that inhibits expression of the PDCL3 polypeptide or polynucleotide encoding PDCL3, or one that binds to, partially or totally blocks stimulation, decreases, prevents, delays activation, inactivates, desensitizes, or down regulates the activity of the PDCL3 polypeptide or polynucleotide encoding PDCL3. Such PDCL3 antagonists can e.g., inhibit PDCL3 expression, e.g., PDCL3 translation, post-translational processing of PDCL3, stability, degradation, or nuclear or cytoplasmic localization of the PDCL3 polypeptide, or transcription, post transcriptional processing, stability or degradation of a polynucleotide encoding PDCL3, or, partially or totally block VEGFR-2 binding to PDCL3.

By "reduce" or "inhibit" is meant the ability to cause an overall decrease preferably of 10% or greater, 15% or greater 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 98% or greater, 99% or greater, or complete or 100% in a parameter, activity, or condition being measured. Reduce or inhibit can refer to, for example, inhibition of PDCL3 expression or activity, inhibition of VEGFR-2 activity or VEGFR-2 mediated angiogenesis, inhibition of angiogenesis, the symptoms of a disorder being treated, the presence or size of metastases or micrometastases, the size of the primary tumor, the presence or the size of the dormant tumor, or the size or number of the blood vessels in angiogenic disorders.

Accordingly, as used herein, "selectively binds" or "specifically binds" refers to the ability of a PDCL3 antagonist agents described herein to bind to a target, such as PDCL3, or a PDCL3 VEGR-2 binding site, or to VEGFR-2, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the agent and the concentration of the agent. The person of ordinary skill in the art can determine appropriate conditions under which the PDCL3 antagonist agents described herein selectively bind the targets using any suitable methods, such as titration of, for example, a PDCL3 antagonist polypeptide agent, in a suitable cell binding assay.

The term "PDCL3 antagonist polypeptide," as used herein, includes polypeptides comprising any naturally occurring polypeptide of a PDCL3 family member as well as any variants thereof (including mutants, fragments, fusions, and peptidomimetic forms) that retain a useful activity, such as inhibition of VEGFR-2 mediated signaling and/or angiogenesis. For example, PDCL3 antagonist polypeptides include polypeptides derived from the sequence of any known PDCL3 having a sequence at least about 70% identical to the sequence of a PDCL3 polypeptide, and preferably at least 75%, at least 80%, at least 85%, at least 90%, at least 95%, at least 97%, at least 98%, at least 99%, or more identity. For example, a PDCL3 antagonist polypeptide described herein can bind to and inhibit the function of an endogenous PDCL3 protein and/or inhibit the function of VEGFR-2. Preferably, a PDCL3 antagonist polypeptide that antagonizes VEGFR-2 signaling pathways inhibits angiogenesis.

As used herein, a "portion," "fragment," or a "derivative" of a PDCL3 antagonist polypeptide is a polypeptide in which one or more physical, chemical, or biological properties has been altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which can result in changes in primary, secondary or tertiary structure. However, as used herein, any such PDCL3 antagonist polypeptide derivative or fragment thereof exhibits at least one of the aforementioned VEGFR-2 antagonist or angiogenesis inhibiting activities. By "fragment" is also meant a portion of a PDCL3 antagonist polypeptide, that comprises, preferably, at least 10%, 20%, 30%, 40%, 50%, 60%, 70%, 80%, 90%, 95%, or more of the entire length of the reference polypeptide. A fragment can comprise 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more amino acids of the PDCL3 antagonist polypeptide known to have VEGFR-2 inhibitory activity, for example.

The terms "RNA interference agent" and "RNA interference" as they are used herein are intended to encompass those forms of gene silencing of PDCL3 mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). Accordingly, in some embodiments, a PDCL3 antagonist agent is a PDCL3 RNA interference agent.

As used herein, a "PDCL3 antibody" is an antibody that binds to PDCL3 with sufficient affinity and specificity. The antibody selected will normally have a binding affinity for PDCL3, for example, the antibody can bind human PDCL3 with a $K_D$ value between $10^{-5}$ M to $10^{-10}$ M. In certain aspects described herein, a PDCL3 antibody can be used as a therapeutic agent in targeting and interfering with diseases or conditions where PDCL3 activity or VEGFR-2 activity is involved. As used herein, a "blocking" antibody or an antibody "antagonist" is one which inhibits or reduces biological activity of the antigen it binds. For example, a PDCL3 antagonist antibody binds PDCL3 and inhibits the ability of PDCL3 to, for example, bind VEGFR-2 and induce angiogenesis, to induce vascular endothelial cell proliferation or to induce vascular permeability. In certain embodiments, blocking antibodies or antagonist antibodies completely inhibit the biological activity of PDCL3 and prevents VEGFR-2 binding to PDCL3.

The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$—$C_H1$-$V_H$—$C_H1$) which, together with complementary light chain polypeptides, form a pair of antigen binding regions (Zapata et al. Protein Eng. 8(10):1057-1062 (1995); and U.S. Pat. No. 5,641,870).

An "agent" can be any chemical, entity, or moiety, including, without limitation, synthetic and naturally-occurring proteinaceous and non-proteinaceous entities. In certain embodiments, agents are small molecules having a chemical moiety. For example, chemical moieties include unsubstituted or substituted alkyl, aromatic, or heterocyclyl moieties. Compounds can be known to have a desired activity and/or property, e.g., inhibit PDCL3 expression or activity or VEGFR-2 activity, or can be selected from a library of diverse compounds, using, for example, screening methods knowns to one of skill in the art.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "disorder" is any condition that would benefit from treatment with, for example, a PDCL3 antagonist agent described herein. An "angiogenesis-dependent disease or disorder," as used herein, refers to those diseases or disorders that are dependent on a rich blood supply and blood vessel proliferation for the diseases' pathological progression (e.g., metastatic tumors), or diseases or disorders that are the direct result of aberrant blood vessel proliferation (e.g., diabetic retinopathy and hemangiomas). Non-limiting examples include abnormal vascular proliferation, ascites formation, psoriasis, age-related macular degeneration, thyroid hyperplasia, preeclampsia, rheumatoid arthritis and osteoarthritis, carotid artery disease, vaso vasorum neovascularization, vulnerable plaque neovascularization, neurodegenerative disorders, Alzheimer's disease, obesity, pleural effusion, atherosclerosis, endometriosis, diabetic/other retinopathies, ocular neovascularizations such as neovascular glaucoma and corneal neovascularization, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma, cancers which require neovascularization to support tumor growth, etc.

The terms "cancer" and "cancerous" refer to or describe the physiological condition in mammals that is typically characterized by unregulated cell growth. Included in this definition are benign and malignant cancers, as well as dormant tumors or micrometastases. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

The terms "subject," "individual," and "patient" are used interchangeably herein, and refer to an animal, for example a human, recipient of the PDCL3-specific antagonist agents, such as a PDCL3 antagonist polypeptide or PDCL3 RNA interference agent described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish.

As used herein, the terms "administering," refers to the placement of a pharmaceutical composition comprising one or more PDCL3 antagonist agents into a subject by a method or route which results in at least partial localization of the agent at a desired site, e.g., tumor site. The agent can be administered by any appropriate route which results in an effective treatment in the subject.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "effective amount" as used herein refers to the amount of a PDCL3 antagonist agent, needed to alleviate at least one or more symptom of the disease or disorder, and relates to a sufficient amount of pharmacological composition to provide the desired effect, i.e., inhibit the formation of new blood vessels or VEFR-2 activity. The term "therapeutically effective amount" therefore refers to an amount of a PDCL3 antagonist agent, such as a PDCL3 antagonist polypeptide or PDCL3-specific RNA interference agent, using the methods as disclosed herein, that is sufficient to effect a particular effect when administered to a typical subject.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (TAR- CEVA®)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY 117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" or "anti-proliferative agent," as used herein, refers to a compound or composition which inhibits growth of a cell in vitro and/or in vivo. Thus, the growth inhibitory agent can be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs described herein include, but are not limited to, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The terms "cell lines," "host cells," and "host cells lines" refer to cells that can be genetically engineered to express a nucleic acid sequence encoding an engineered PDCL3 polypeptide and/or a nucleic acid sequence encoding a recombinant protein of interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express an engineered PDCL3 polypeptide, a desired recombinant polypeptide or protein of interest, or both.

The term "mammalian host cell" is used to refer to a mammalian cell which is capable of being transfected with a nucleic acid sequence and then of expressing a selected recombinant protein of interest. The term includes the progeny of the parent cell, whether or not the progeny is identical in morphology or in genetic make-up to the original parent, so long as the selected gene is present. Suitable mammalian cells for use in the present invention include, but are not limited to Chinese hamster ovary (CHO) cells, baby hamster kidney (BHK) cells, human HeLa cells, monkey COS-1 cell, human embryonic kidney 293 cells, mouse myeloma NSO and human HKB cells (U.S. Pat. No. 6,136,599). The other cell lines are readily available from the ATCC.

The term "recombinant" when used with reference to a cell indicates that the cell replicates a heterologous nucleic acid, or expresses a peptide or protein encoded by a heterologous nucleic aci, such as a nucleic acid sequence encoding an engineered PDCL3 polypeptide and/or a nucleic acid sequence encoding a recombinant protein of interest. Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell.

As used herein, the terms "recombinant cell," "recombinant cell line," or "modified cell line" refers to a cell line either transiently or stably transformed with one or more nucleic acid constructs, as described herein. Polynucleotides, genetic material, recombinant DNA molecules, expression vectors, and such, used in the compositions and methods described herein can be isolated using standard cloning methods such as those described by Sambrook et al. (Molecular Cloning: A Laboratory Manual, Second Edition, Cold Spring Harbor, N.Y., 1989; which is incorporated herein by reference). Alternatively, the polynucleotides coding for a recombinant protein product used in the compositions and methods described herein can be synthesized using standard techniques that are well known in the art, such as by synthesis on an automated DNA synthesizer.

Peptides, polypeptides and proteins that are produced by recombinant animal cell lines using the cell culture compositions and methods described herein can be referred to as "recombinant protein of interest," "recombinant peptide," "recombinant polypeptide," and "recombinant protein." The expressed protein(s) can be produced intracellularly or secreted into the culture medium from which it can be recovered and/or collected. Accordingly, the term "recombinant protein of interest" refers to a protein or fragment thereof expressed from an exogenous nucleic acid sequence introduced into a host cell.

As used herein, the term "transfection" is used to refer to the uptake of an exogenous nucleic acid by a cell, and a cell has been "transfected" when the exogenous nucleic acid has been introduced inside the cell membrane. A number of transfection techniques are well known in the art and are disclosed herein.

The term "transformation" as used herein refers to a change in a cell's genetic characteristics, and a cell has been transformed when it has been modified to contain a new DNA. For example, a cell is transformed where it is genetically modified from its native state. Following transfection, the transforming nucleic acid can recombine with that of the cell by physically integrating into a chromosome of the cell, can be maintained transiently as an episomal element without being replicated, or can replicate independently as a plasmid. A cell is considered to have been stably transformed when the transforming nucleic acid is replicated with the division of the cell.

As used herein an "expression vector" refers to a DNA molecule, or a clone of such a molecule, which has been modified through human intervention to contain segments of DNA combined and juxtaposed in a manner that would not otherwise exist in nature. DNA constructs can be engineered to include a first DNA segment encoding an acetylation-resistant engineered PDCL3 polypeptide described herein operably linked to additional DNA segments encoding a desired recombinant protein of interest. In addition, an expression vector can comprise additional DNA segments, such as promoters, transcription terminators, enhancers, and other elements. One or more selectable markers can also be included. DNA constructs useful for expressing cloned DNA segments in a variety of prokaryotic and eukaryotic host cells can be prepared from readily available components or purchased from commercial suppliers.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells can be cultured in suspension or while attached to a solid substrate. Fluidized bed bioreactors, hollow fiber bioreactors, roller bottles, shake flasks, or stirred tank bioreactors, with or without microcarriers, can be used.

As used herein, "cell culture medium" is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available.

BRIEF DESCRIPTION OF THE FIGURES

FIG. 1A. HEK-293 cells expressing VEGFR-2 were transfected with different concentrations of C-terminus Myc-tagged PDCL3. After 48 hours cells were lysed and whole cell lysates (WCL) were blotted for VEGFR-2, PDCL3 and Hsp70 for loading control. Quantification of premature (newly synthesized and partially glycosylated VEGFR-2 corresponding to lower molecular weight) and mature (fully glycosylated) forms of VEGFR-2 is shown. Mean results of three independent experiments are shown. *P=0.04 and **p=0.15. FIG. 1B. Human umbilical vein endothelial cells (HUVECs) were transfected with control siRNA or PDCL3-siRNA. After 48 hours cells serum-starved for overnight followed by stimulation with VEGF for 10 minutes. Cells were lysed and whole cell lysates were blotted for phospho-Y1054-VEGFR-2, total VEGFR-2, PDCL3 and Hsp70 for loading control. FIG. 1C. Thermo-induced aggregation of VEGFR-2 was measured using PSA dye as described in the materials and method section. FIG. 1D. In vitro transcription/translation of VEGFR-2 in the absence or presence of exogenous recombinant PDCL3 was performed as described in the materials and method section and schematic of the procedure is shown. FIG. 1E. In vitro translated VEGFR-2 protein in the absence or presence of exogenous recombinant PDCL3 was blotted for VEGFR-2. FIG. 1F. Western blot of in vitro translated VEGFR-2 protein in the absence or presence of exogenous recombinant PDCL3 and MG132 is shown.

FIG. 2A. Illustrated is the schematic of treatment of cells with cycloheximide (CHX) and VEGF. PAE cells co-expressing VEGFR-2 with empty vector (pMSCV) or PDCL3 were incubated with CHX for 90 minutes followed by stimulation with VEGF for indicated times. Whole cell lysates was blotted for VEGFR-2 and loading control protein, PLCγ1. FIG. 2B. Shown are the quantification of the half-life of mature VEGFR-2 and pre-mature VEGFR-2 based on the VEGFR-2 blot from the panel FIG. 2A. FIGS. 2C-2D. PAE cells co-expressing VEGFR-2 with empty vector (pMSCV) or PDCL3 were stimulated with VEGF for indicated times and whole cell lysates were processed as panel FIG. 2A.

FIG. 3A. Fli-eGFP-transgenic adult male and female zebrafish (*Danio rerio*) were mated and the embryos were injected with LACZ or PDCL3 mRNA. The embryos were examined after 28 post fertilization (hpf). FIG. 3B. Graph is quantification of intersegmental vessel (10 fish/group). FIG. 3C. Zebrafish embryos were co-injected with PDCL3 morpholino and control mRNA (LacZ) or with VEGFR-2 mRNA and pictures were taken after 28 hpf. FIG. 3D. Quantification of intersegmental vessel (10 fish/group) is shown. Mean of three independent experiments is shown. Error bars represent SD. *P<0.005.

FIG. 4A. HUVEC cells were incubated in hypoxia or in normal oxygen (normoxia) for overnight. Cells were lysed and whole cell lysates (WCL) was blotted for PDCL3, VEGFR-2 and PLC71. Graphs are the quantification of expression of PDCL3 and VEGFR-2 representative of three independent experiments. FIG. 4B. HUVEC cells were transfected with either control siRNA (ctr. siRNA) or PDCL3 siRNA and after 24 hours cells were incubated in hypoxic condition for overnight. Cells were lysed and whole cell lysates were blotted for VEGFR-2, PDCL3 and PLC71. Graph is representative of three independent experiments. FIG. 4C. Mouse hypoxia-induced angiogenesis was performed as described in the materials and methods section. Immunohistochemistry staining of postnatal day 17 (P17) of normal mouse eye tissue (normoxia) and hypoxia-induced retinopathy of prematurity mouse eye were stained for PDCL3 and VEGFR-2.

FIGS. 5A-5C demonstrate that PDCL3 undergoes N-terminal methionine acetylation. FIG. 5A. Illustrated is mass spectra analysis of acetylated PDCL3 peptide (SEQ ID NO: 14). PAE cells expressing Myc-tagged PDCL3 was immunoprecipitated with anti-Myc antibody and subjected to mass spectrometry analysis as described in materials and methods section. FIG. 5B. Shown is the schematic of HA-tagged N-terminus methionine mutant PDCL3 and wild-type PDCL3 and their expression in PAE cells. FIG. 5C. Pulse-chase analysis (CHX, 20 µg/ml) of wild-type and HA-tagged methionine mutant PDCL3 is shown. HEK-293 cells expressing wild-type PDCL3 and mutant PDCL3, HA-tagged PDCL3 were incubated with CHX as indicated, cells were lysed and whole cell lysates was blotted for PDCL3 or control protein, actin. Quantification of the same blot also is shown.

FIG. 6A. Cell lysates from HEK-293 cells co-expressing PDCL3 with VEGFR-2 or HA-PDCL3 with VEGFR-2 were immunoprecipitated with VEGFR-2 and immunoblotted for PDCL3 using anti-Myc antibody. Whole cell lysates was also blotted for VEGFR-2, PDCL3 and HSp70 as a loading control. Ubiquitination of VEGFR-2 was determined by immunoprecipitation with anti-VEGFR-2 followed by immunoblotting with anti-ubiquitin antibody. FIG. 6B. The graph is quantification of the ubiquitination blot of VEGFR-2. FIG. 6C. Angiogenic potential of wild-type and HA-tagged methionine mutant PDCL3 expressed in PAE cells is shown. PAE cells engineered to express VEGFR-2 alone, VEGFR-2 with wild-type PDCL3 or VEGFR-2 with HA-tagged methionine mutant PDCL3. Cells were plated on matrigel and pictures were taken after 12 hours. Image J was used to quantify tube formation. Graph is representative of three independent experiments.

FIGS. 7A-7E demonstrate that PDCL3 is localized at the ER and associates with the newly synthesized VEGFR-2. FIG. 7A. Cells expressing VEGFR-2 alone or together were subjected cell surface biotinylation. Non-biotinylated and biotinylated fractions were immunoprecipitated with anti-VEGFR-2 antibody and blotted for PDCL3 using anti-c-Myc antibody. Non-biotinylated and biotinylated fractions also were blotted for VEGFR-2 and PARP as a control. FIG. 7B. HEK-293 cells were co-transfected with Myc-tagged PDCL3 and VEGFR-2 and after 48 hours they were treated with BFA or control vehicle. Cells were lysed and whole cell lysates were either blotted for VEGFR-2 or were subjected co-immunoprecipitation using anti-c-Myc antibody followed by immunoblotting with anti-VEGFR-2. FIG. 7C. HEK-293 cells were co-transfected with Myc-tagged PDCL3 and VEGFR-2 and after 48 hours cells were fixed and subjected to IF staining as described in Materials and Method section. Cells were stained with anti-PDCL3, anti-c-myc antibodies (FIGS. 7C-7D) or endoplasmic reticulum specific dye FIG. 7E.

FIG. 8A. HEK-293 cells were co-transfected with Myc-tagged PDCL3 and GFP tagged-KDEL ("KDEL" disclosed as SEQ ID NO: 12) and after 48 hours cells were fixed and subjected to IF staining using anti-PDCL3 antibody as described in Materials and Method section. FIG. 8B. Cells were lysed and subjected to cellular fraction and the fraction enriched in ER compartments was analyzed for PDCL3 and VEGFR-2. GRP78 is used as ER marker. WCL, whole cell lysate.

FIG. 9A. PAE cells expressing wild-type PDCL3 or HA-tagged methionine mutant PDCL3 were incubated in normal (−) or hypoxic (+) environment for 24 hours. Cells were incubated with CHX as indicated, cells were lysed and whole cell lysates was blotted for PDCL3 or control protein, actin. Quantification of the same blot also is shown. FIGS. 9A-9B. Graphs are representative of two independent experiments.

FIG. 12A. Schematic of the experiment is shown. FIG. 12B. In vitro translation and transcription was performed as recommended by the manufacturer except in one group recombinant PDCL3 was added into reaction mixture.

FIG. 13A. Expression of PDCL3 and VEGFR-2 in kidney cancer cell line, 786-0. FIG. 13B. The effect of PDCL3 shRNA on VEGFR-2 expression. FIG. 13C. 3 dimensional growth of 786-O in control and PDCL3-shRNA expressing cells (day (D) 2, 6 and 10 are shown). FIG. 13D. Morphology of cells are shown. PDCL3-shRNA inhibits tumor foci formation.

FIGS. 14A-14B demonstrates identification of novel small molecule inhibitors for PDCL3 using high throughput screening. Given that PDCL3 plays a fundamental role in maturation and folding of receptor tyrosine kinases (RTKs), such as VEGFR-2, and considering that activity of these RTKs are cornerstone of tumor growth and metastasis, it was decided to screen for small molecule inhibitors that could antagonize PDCL3 function in tumor cells. LOPAC1280 (a library of Pharmacologically Active Compounds), which is a collection of 1,280 pharmacologically active compounds, was used. The library is most commonly used to validate new drug discovery assays and characterize orphan targets.

Figure 1A:
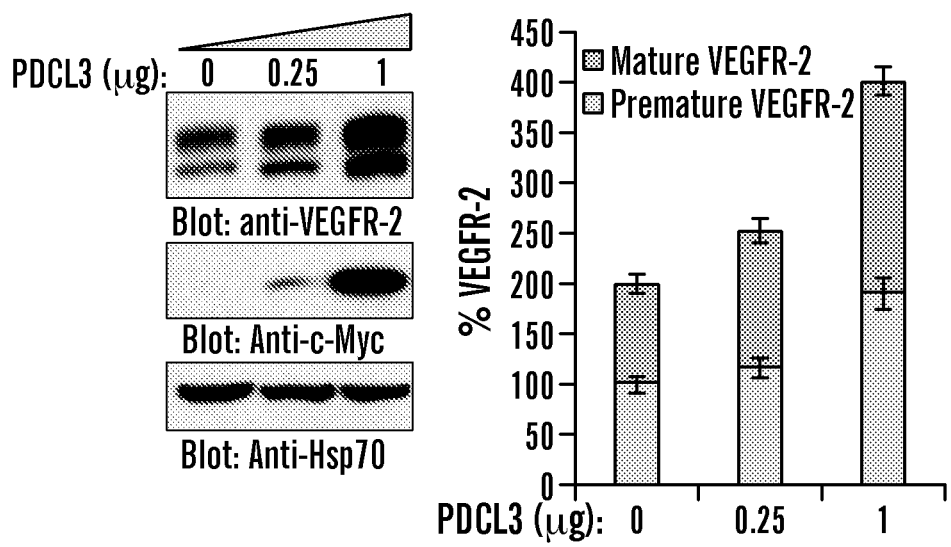
FIGS. 1A-1F demonstrate that PDCL3 promotes VEGFR-2 folding and increases its expression.

16 lead compounds were identified as PDCL3 inhibitors and their potency and efficacy in inhibition of PDCL3 was validated.

DETAILED DESCRIPTION

As described herein, the inventors have identified a novel function for PDCL3 (phosducin-like 3) in the stabilization of VEGFR-2, and discovered that PDCL3 acts as a VEGFR-2 chaperone protein, thereby stabilizing VEGFR-2. PDCL3 co-localizes with VEGFR-2 in cells and recognizes the juxtamembrane domain of VEGFR-2. Over-expression of PDCL3 increases the abundance of VEGFR-2 protein, whereas silencing of PDCL3 expression by siRNA in endothelial cells significantly reduces VEGFR-2 protein, as demonstrated herein. Moreover, as demonstrated herein, PDCL3 activity is required for endothelial cell proliferation and capillary tube formation of primary endothelial cells and angiogenesis in developing zebrafish embryos. PDCL3 exhibits its activity on endothelial cell proliferation and angiogenesis, in part, by rendering VEGFR-2 a more stable protein and preventing its ubiquitylation and proteolytic degradation. Taken together, the data provided herein demonstrate that PDCL3 associates with VEGFR-2 and control its function, and with it angiogenesis and angiogenesis-mediated disorders.

Accordingly, provided herein are PDCL3 antagonist agents, such as a PDCL3 antagonist polypeptide, PDCL3-specific inhibitory nucleic acid, PDCL3 antagonist antibody or antigen-binding fragment thereof, or PDCL3 specific small molecule that inhibits or causes or facilitates a qualitative or quantitative inhibition, decrease, or reduction in one or more processes, mechanisms, effects, responses, functions, activities or pathways mediated by PDCL3, and methods comprising such PDCL3 antagonist agents for modulating and controlling pathological angiogenesis.

Further, as described herein, the inventors have discovered that preventing N-terminal acetylation of PDCL3 potently increases PDCL3 chaperone protein activity. The inventors demonstrate herein that PDCL3 is present at both the endoplasmic reticulum (ER) and cytoplasmic compartments. Consistent with the chaperone function of PDCL3, ER-localized PDCL3 associates with newly synthesized VEGFR-2, where it protects VEGFR-2 from degradation. The data described herein demonstrate that N-terminal methionine acetylation regulates stability of PDCL3. PDCL3 stability plays an important role in angiogenesis, as its expression was upregulated by hypoxia, a master regulator of angiogenesis. Over-expression of an engineered PDCL3 unable to undergo N-terminal acetylation was significantly more potent than the wild type PDCL3 in its ability to stimulate angiogenesis in endothelial cells via increasing PDCL3 stability and chaperone protein activity. Thus, engineered PDCL3 polypeptides are useful in compositions and methods for enhanced expression and production of recombinant proteins and in vitro protein synthesis.

Accordingly, provided herein, in some aspects, are novel compositions comprising engineered PDCL3 polypeptides having enhanced chaperone activity, recombinant cells comprising such engineered PDCL3 polypeptides having enhanced chaperone activity, and methods thereof for therapeutic protein production and in vitro protein synthesis.

PDCL3

PDCL3 is part of the family of phosducin-like proteins (PhLPs) that were initially identified as modulators of G protein signaling. New and unexpected roles for PDCL3 have been identified and are demonstrated herein. PDCL3 is shown herein to act as a novel VEGFR-2 associating protein and further, it has been demonstrated herein that PDCL3 is an essential mediator of VEGFR-2 stability and function. In addition, overexpression of an engineered PDCL3 unable to undergo N-terminal acetylation was significantly more potent than the wild type PDCL3 in its ability to stimulate angiogenesis in endothelial cells via increasing PDCL3 stability and chaperone protein activity.

Accordingly, compositions and methods to inhibit PDCL3-dependent targeting of and association with VEGFR-2 are provided herein as alternative therapeutic strategies to block VEGFR-2 signaling in angiogenesis-associated diseases. Also, engineered PDCL3 polypeptides are provided herein in compositions and methods for enhanced expression and production of recombinant proteins and in vitro protein synthesis.

Accordingly, the terms "PDCL3" or "PhLP3" as used herein, refers to the 239-amino acid human phosducin-like protein 3 (PDCL3) having the amino acid sequence: MQDPNADTEWNDILRKKGILPPKESLKELEEEAEE-EQRILQQSVVKTYEDMTLEELEDHEDEF NEEDERAI-EMYRRRRLAEWKATKLKNKFGEVLEISGKDYVQE-VTKAGEGLWVILHLYKQGI PLCALINQHLSG-LARKFPDVKFIKAISTTCIPNYPDRNLPTIFVYLEG-DIKAQFIGPLVFGGMNL TRDELEWKLSESGAIMTDL-EENPKKPIEDVLLSSVRRSVLMKRDSDSEGD (SEQ ID NO: 1), as described by, e.g., NP_076970.1, and encoded by, e.g., the sequence of NM_024065.4 (SEQ ID NO: 2), together with naturally occurring allelic, splice variants, and naturally occurring processed forms thereof. Other forms of PDCL3 encompassed by the term "PDCL3," include, for example, mouse PDCL3, as described by, e.g., NP_081126.2 (SEQ ID NO: 3), and encoded by the sequence of NM_026850.4 (SEQ ID NO: 4); and rat PDCL3, as described by, e.g., NP_001020880.1 (SEQ ID NO: 5), and encoded by the sequence of NM_001025709.1 (SEQ ID NO: 6). Typically, PDCL3 refers to human PDCL3. The term "PDCL3" is also used to refer to truncated forms or fragments of the polypeptide comprising specific amino acid sequences of the 239-amino acid human PDCL3 having VEGFR-2 inhibitory activity or chaperone activity, as provided herein. Reference to any such forms of PDCL3 can be identified in the application, e.g., by "PDCL3 (1-50)."

Phosducin-like proteins (PhLPs) refer to a conserved family of proteins with thioredoxin-like domains that were initially identified as modulators of G protein signaling (Flanary et al., 2000; Blaauw et al., 2003). Three homologous PhLPs PhLP1, PhLP2, and PhLP3 (also referred to herein as "PDCL3") have been identified, all of which share an N-terminal helical domain, a central thioredoxin-like domain, and a charged carboxyl terminus (Blaauw et al., 2003). There is a high degree of sequence homology between all Pdc family members in the C-terminal ~150 amino acids, indicating that all retain the thioredoxin fold of the C-terminal domain of Pdc. In contrast, their N-terminal regions differ significantly. The N-terminal domains of Pdc and PhLP1 both contain a conserved 11-amino acid sequence of Helix 1 which is imperative in binding Gβγ, while PhLP2 and PDCL3 do not have this sequence and bind Gβγ poorly. PhLPs 1-3 all contain an acidic sequence in the loop between Helix 2 and 3 of the Pdc structure that is not well-conserved in Pdc. This acidic region has been shown to play an important role in the binding of PhLP1 to CCT, and accordingly PhLPs 1-3 all bind CCT while Pdc does not. Apart from this loop and the Helix 3 region that follows, there is very little homology in the N-terminal domain between Pdc subfamily members.

Recent studies suggest that PhLPs are involved in protein-folding machinery system by acting as co-factors and can bind Chaperonin Containing Tcp1 (CCT; also called TCP 1-containing Ring Complex [TRiC]) (McLaughlin et al., 2002; Martŏ'n-Benito et al., 2004; Lukov et al., 2006; Stirling et al., 2006). CCT is composed of eight evolutionary conserved subunits, which are known to bind to nonnative proteins and promote their folding in an ATP-dependent manner (Hartl and Hayer-Hartl, 2002). Although initially the cytoskeletal proteins, tubulin and actin have been described as the only substrates of CCT, recent studies have shown that CCT's substrate spectrum is broader than originally thought (Dunn et al., 2001; Camasses et al., 2003; Liu et al., 2005).

Despite the high degree of homology in their C-terminal domains and their shared ability to bind CCT, PDCL3 is believed to have a physiological function distinct from PhLP2, as PhLP2 and PDCL3 deletions in yeast and Dictyostelium lead to very different phenotypes. The PhLP2 deletion in both organisms resulted in a loss of viability, whereas PDCL3 deletion had no obvious effects. Moreover, PDCL3 over-expression did not rescue the lethality of PhLP2 deletion. Further genetic analyses have indicated a role for PDCL3 in 1-tubulin folding. In yeast, deletion of PDCL3 protected cells against the toxic effects of excess free P-tubulin, indicating that PhLP3 is necessary for 3-tubulin folding. In C. elegans, siRNA-mediated knockdown of PDCL3 resulted in defects in microtubule architecture and aberrant cytokinesis, again pointing to a positive role of PDCL3 in tubulin function. Cryo-EM studies have demonstrated the formation of a ternary complex between PDCL3, tubulin and CCT, indicating that PDCL3 interacts directly with CCT to regulate $\beta$-tubulin folding (Willardson, Cell Signal. 2007 December; 19(12):2417-27).

PDCL3 also has been shown to regulate actin function. Genetic deletion of the pac10 subunit of prefoldin in yeast results in a marked decrease in F-actin in the cell, while dual PhLP3$\Delta$ and pac10$\Delta$ deletions restored F-actin to the same level as wild-type. This finding indicates that PDCL3 can down-regulate actin expression or F-actin formation. In support of this finding, PDCL3 inhibits actin folding in in vitro assays. However, the PhLP3$\Delta$pac10$\Delta$ deletions greatly impaired a number of actin-dependent functions compared to pac10$\Delta$ alone or wild-type cells.

As described herein, novel functions for PDCL3 (phosducin-like 3) in the stabilization of VEGFR-2 have been identified, and it has been discovered that PDCL3 acts as a VEGFR-2 chaperone protein, thereby stabilizing VEGFR-2, and that engineered PDCL3 lacking N-terminal acetylation can act to enhance protein production. PDCL3 co-localizes with VEGFR-2 in cells and recognizes the juxtamembrane domain of VEGFR-2. Over-expression of PDCL3 increases the abundance of VEGFR-2 protein, whereas silencing PDCL3 expression by siRNA in endothelial cells significantly reduces VEGFR-2 protein, as demonstrated herein. Moreover, as demonstrated herein, PDCL3 activity is required for endothelial cell proliferation and capillary tube formation of primary endothelial cells and angiogenesis in developing zebrafish embryos. PDCL3 elicits its activity on endothelial cell proliferation and agiogenesis, in part, by rendering VEGFR-2 a more stable protein and preventing its ubiquitylation and proteolytic degradation. In addition, it has been demonstrated that engineered PDCL3 lacking N-terminal acetylation stabilizes VEGFR-2 and can act to enhance protein production. Taken together, the data provided herein demonstrate that PDCL3 associates with VEGFR-2 and control its function, and with it angiogenesis and angiogenesis-mediated disorders, and that engineered PDCL3 lacking N-terminal acetylation can enhance protein stability and production.

Accordingly, provided herein are novel compositions comprising, for example, PDCL3 polypeptides having VEGFR-2 inhibitory activity, inhibitory PDCL3 antibodies and PDCL3-binding fragments thereof, PDCL3 inhibitory nucleic acid molecules, and methods of their use in anti-angiogenesis and anti-tumor proliferation and invasiveness therapies, such as the treatment of cancer, as well as the treatment of those vascular diseases where pathological angiogenesis plays a role, such as in carotid artery disease, vasa vasorum neovascularization, and plaque neovascularization.

Also provided herein are novel compositions comprising engineered PDCL3 polypeptides having enhanced chaperone activity, recombinant cells comprising such engineered PDCL3 polypeptides having enhanced chaperone activity, and methods thereof for therapeutic protein production and in vitro protein synthesis.

PDCL3 and VEGR2 Interactions and Inhibition of VEGFR2 Signaling

Provided herein are novel compositions and methods for inhibiting PDCL3 interaction with VEGFR-2 and consequently VEGFR-2 activity, for the inhibition of angiogenesis and angiogenesis-mediated disorders.

VEGFR-2, also called KDR in humans and Flk-1 in mice, is a primary receptor and mediator for the pro-angiogenic effects of VEGF signaling. VEGFR-2 is bound and activated by VEGF-A, VEGF-C and VEGF-D. In endothelial cells, VEGFR-2 activation has been shown to stimulate cell proliferation and migration, and in vivo, VEGFR-2 activation has been shown to trigger angiogenesis and increase vasculature permeability. Increased angiogenesis is well-established as an important feature of tumor growth and various retinopathies, while increased permeability of the vasculature is a significant event in many inflammatory responses.

VEGFR-2 signaling has been shown to play a critical role in diverse pathological conditions, ranging from cancer to age-related macular degeneration (Carmeliet, 2003; Folkman, 2006), and regulation of VEGFR-2 expression and function is an important rate-limiting mechanism for induction of angiogenesis. Several mechanisms have been implicated in the expression and stability of VEGFR-2 in endothelial cells. VEGFR-2 is generally expressed at low levels in most adult vessels but its expression is strongly up-regulated in certain pathological conditions such as hypoxia and ischemic conditions (Brogi, 1996; Kanellis, 2002). Upon binding to VEGF family ligands, VEGFR-2 is removed from cell surface through endocytosis and down-regulation (Singh et al., 2005). Ligand-mediated clearance of VEGFR-2 from plasma membrane of endothelial cells is established through 13-Trcp 1, an ubiquitin E3 ligase that recognizes VEGF-stimulated VEGFR-2 through a unique phosphodegradation motif present in the carboxyl tail of VEGFR-2 leading to its ubiquitination and degradation (Meyer et al., 2011).

PDCL3 is demonstrated herein as a novel regulator of VEGFR-2. PDCL3 can co-localize with VEGFR-2 in cells and is shown to specifically recognize and bind to the juxtamembrane domain of VEGFR-2. Over-expression of PDCL3 increases the abundance of VEGFR-2 protein, whereas silencing PDCL3 expression by siRNA in endothelial cells significantly reduces VEGFR-2 protein, as demonstrated herein. Furthermore, hypoxia is shown to regulate PDCL3 expression in endothelial cells and its expression is shown to be required for angiogenesis.

Figure 1B:
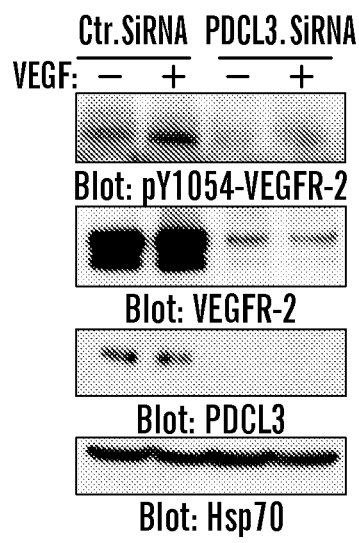

More specifically, it is shown herein that increasing expression of PDCL3 increases the abundance of premature and mature forms of VEGFR-2 in a dose-dependent manner (FIG. 1A) and silencing expression of PDCL3 significantly reduces expression of VEGFR-2 and its activation/tyrosine phosphorylation in response to VEGF stimulation (FIG. 1B).

Figure 1C:
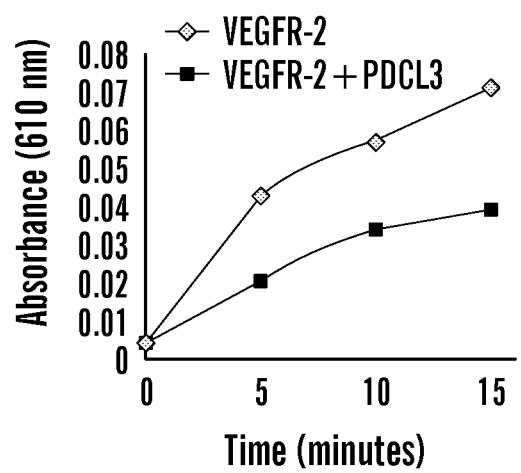
Figure 1D:
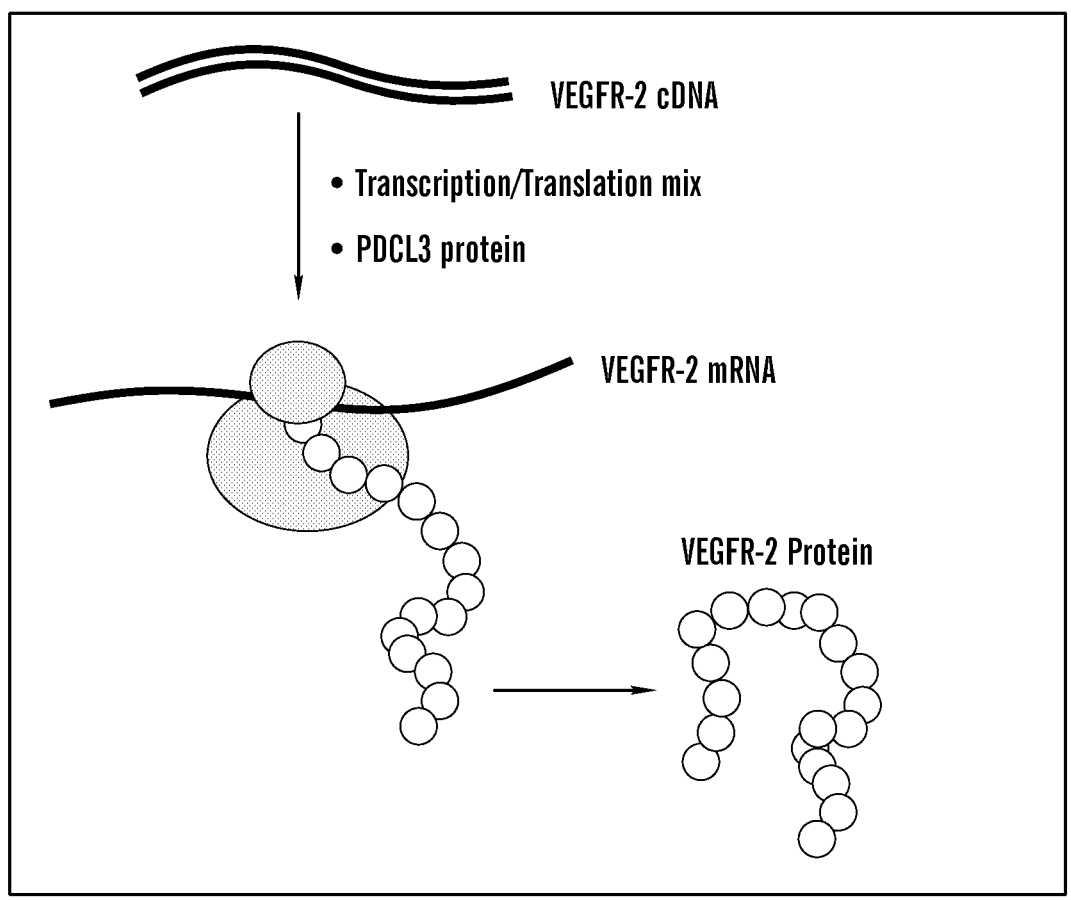
Figure 1E:
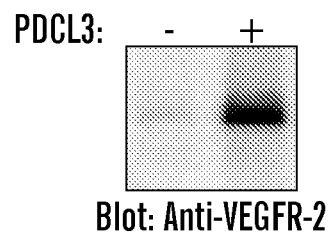
Figure 1F:
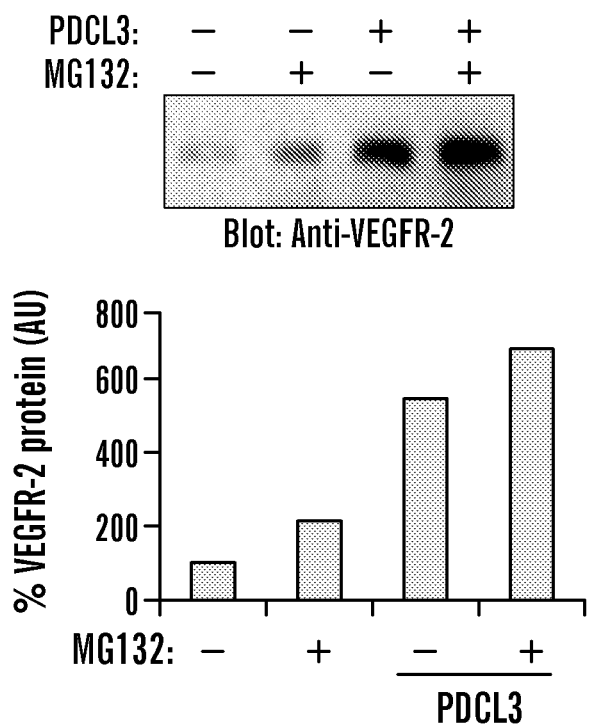

To examine the chaperone function of PDCL3, thermo-induced aggregation of VEGFR-2 was measured. Incubation of immunoprecipitated VEGFR-2 in the presence of PDCL3 at 45° C. significantly reduced aggregation of VEGFR-2 in a time-dependent manner (FIG. 1C). In addition, recombinant PDCL3 protein significantly increased the yield of in vitro translated VEGFR-2 (FIG. 1E) and this effect of PDCL3 was further augmented by proteasome inhibitor, MG132 (FIG. 1F).

Figure 2A:
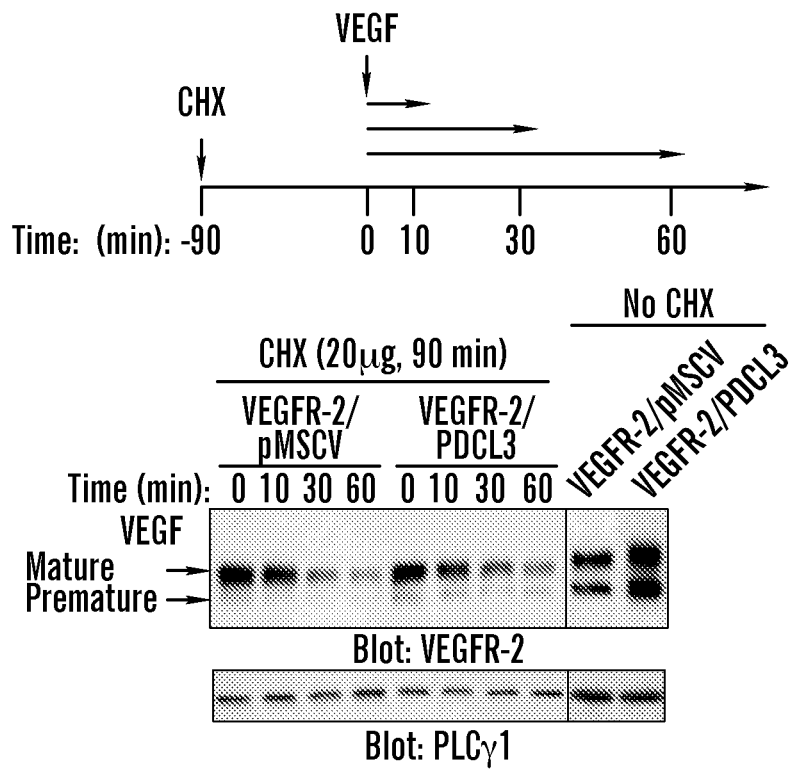
FIGS. 2A-2D demonstrate that PDCL3 increases the stability of newly synthesized VEGFR-2.
Figure 2B:
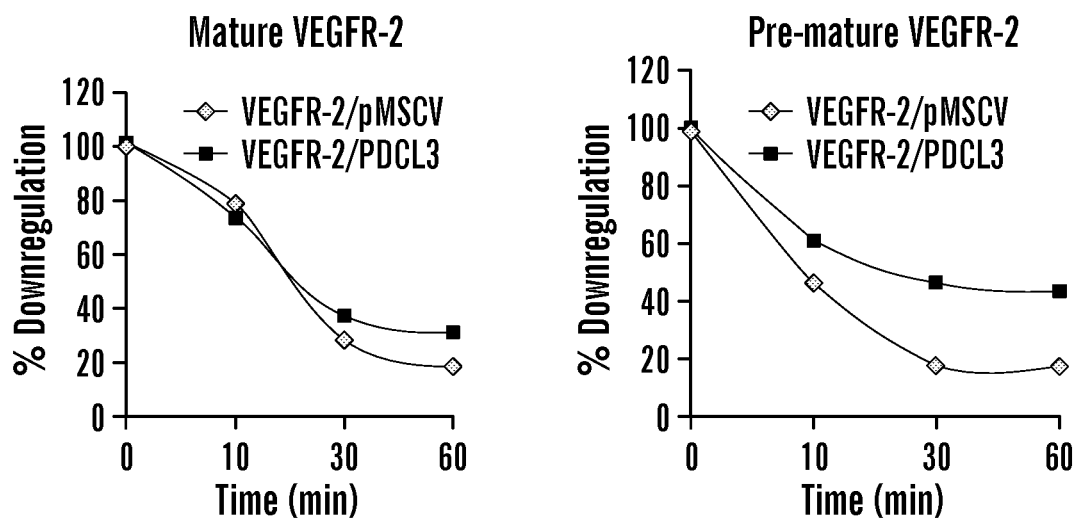

The effect of PDCL3 on the stability of premature VEGFR-2 was tested by treating cells expressing VEGFR-2 alone or co-expressing PDCL3 with a protein synthesis inhibitor, cycloheximide, followed by stimulation of cells with VEGF for various time points. Cycloheximide treatment did not significantly inhibit the appearance of premature VEGFR-2 in cells co-expressing VEGFR-2 with PDCL3 (FIGS. 2A, 2B). The presence of premature VEGFR-2 persisted even when cells were treated with VEGF (FIGS. 2A, 2B). The presence of mature VEGFR-2 and the rate of VEGF-induced downregulation remained the same in the presence of CHX in cells expressing VEGF-2 alone or co-expressing VEGFR-2 with PDCL3 (FIGS. 2A, 2B). The data indicates that PDCL3 by interacting with VEGFR-2 extends the half-life of newly made VEGFR-2. Taken together, the data demonstrate that PDCL3 associates with premature/newly synthesized VEGFR-2 and contributes to its maturation.

Figure 3A:
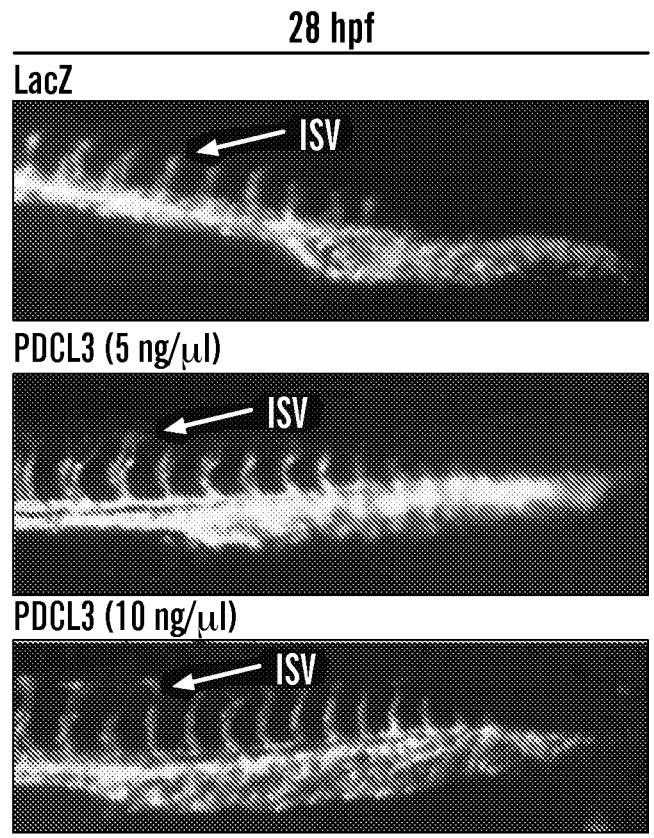
FIGS. 3A-3D demonstrate that PDCL3 promotes angiogenesis in Zebrafish.
Figure 3B:
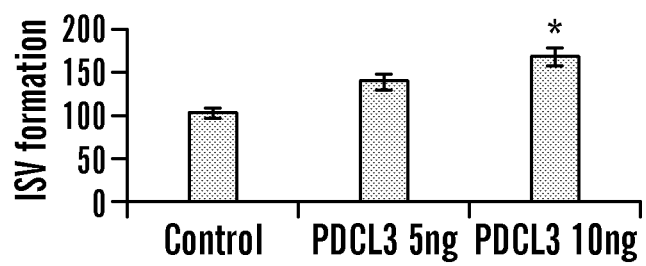
Figure 3C:
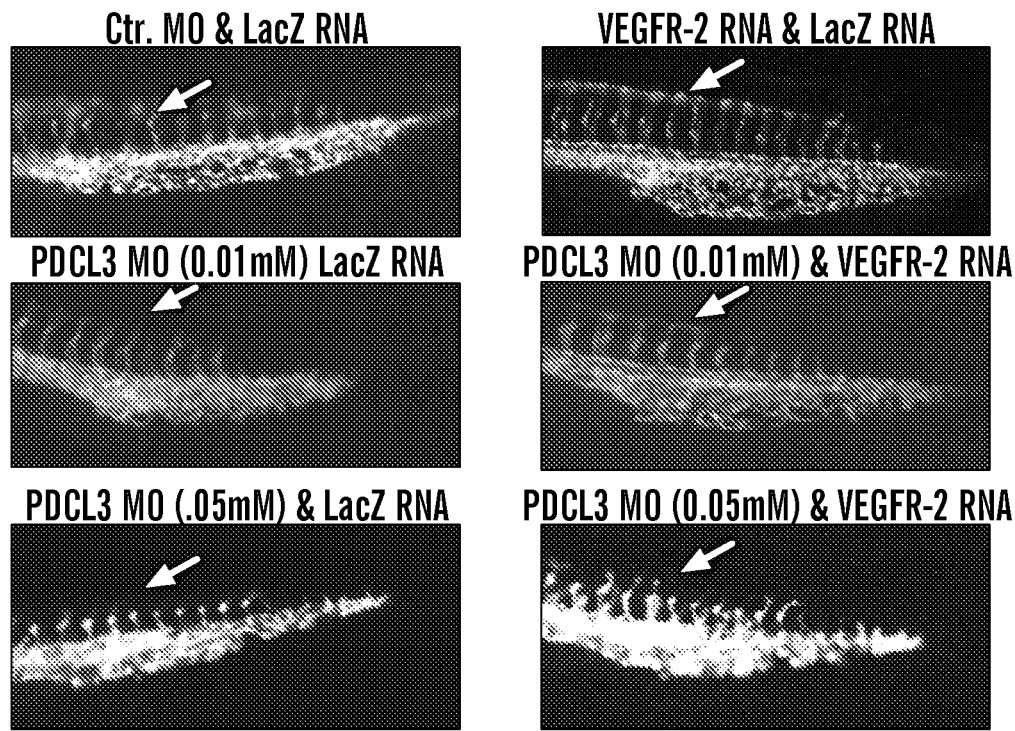

Microinjection of in vitro translated human PDCL3 mRNA into one-stage zebrafish embryos significantly increased angiogenesis in a dose-dependent manner (FIG. 3A). Illustrated is the quantification of blood vessel formation in response to Microinjection of human pdcl3 mRNA (FIG. 3B). In contrast, silencing the expression of PDCL3 in zebrafish by morpholino significantly inhibited angiogenesis (FIG. 3C) and co-injection of pdcl3 morpholino with VEGFR-2 mRNA markedly reversed the effect of pdcl3 knockdown (FIG. 3C) indicating that VEGFR-2 is the primary downstream target of PDCL3.

Figure 4A:
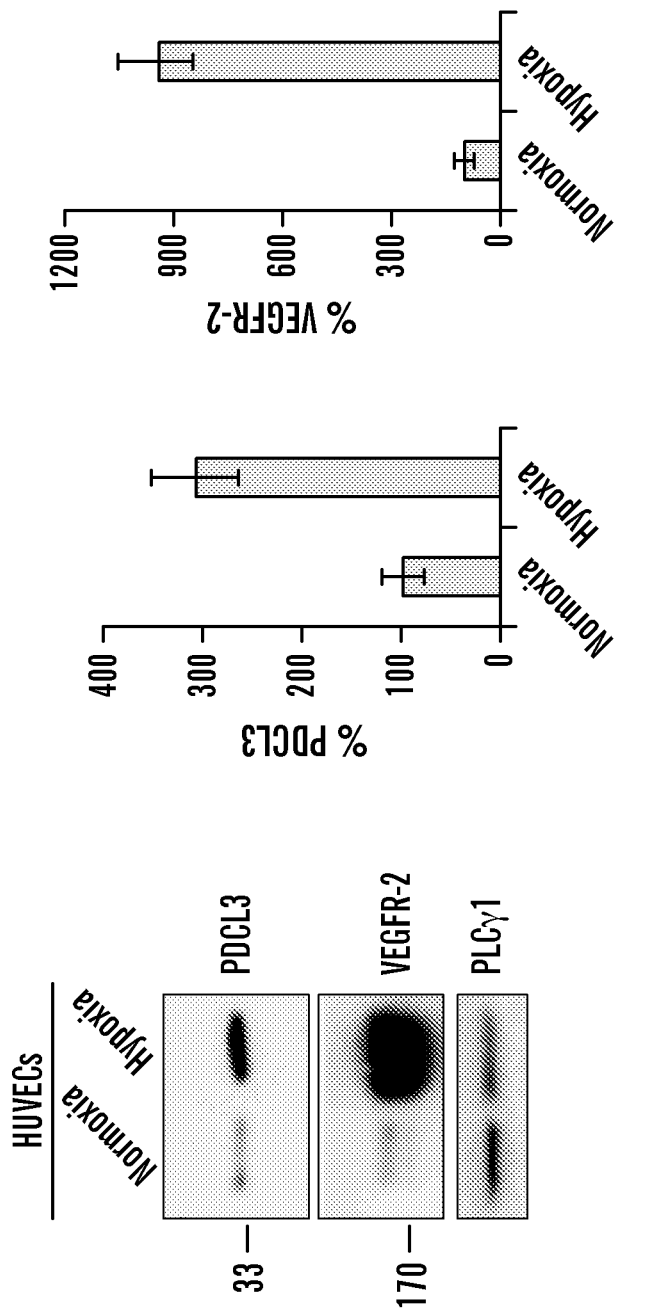
FIGS. 4A-4C demonstrate that hypoxia upregulates expression of PDCL3 in endothelial cellS.
Figure 4B:
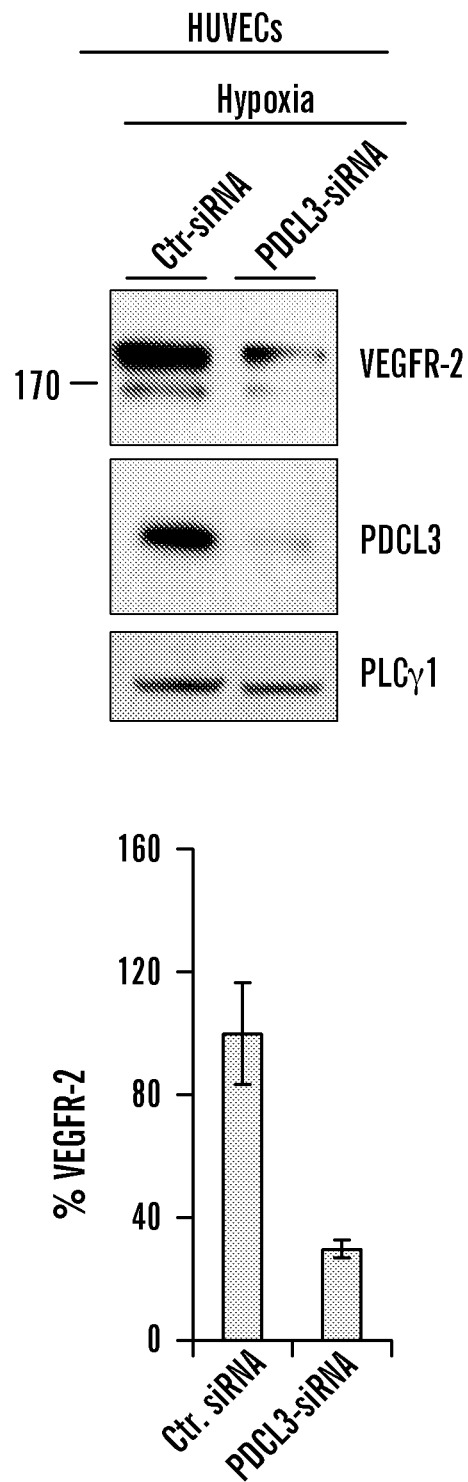
Figures 9A, 9B:
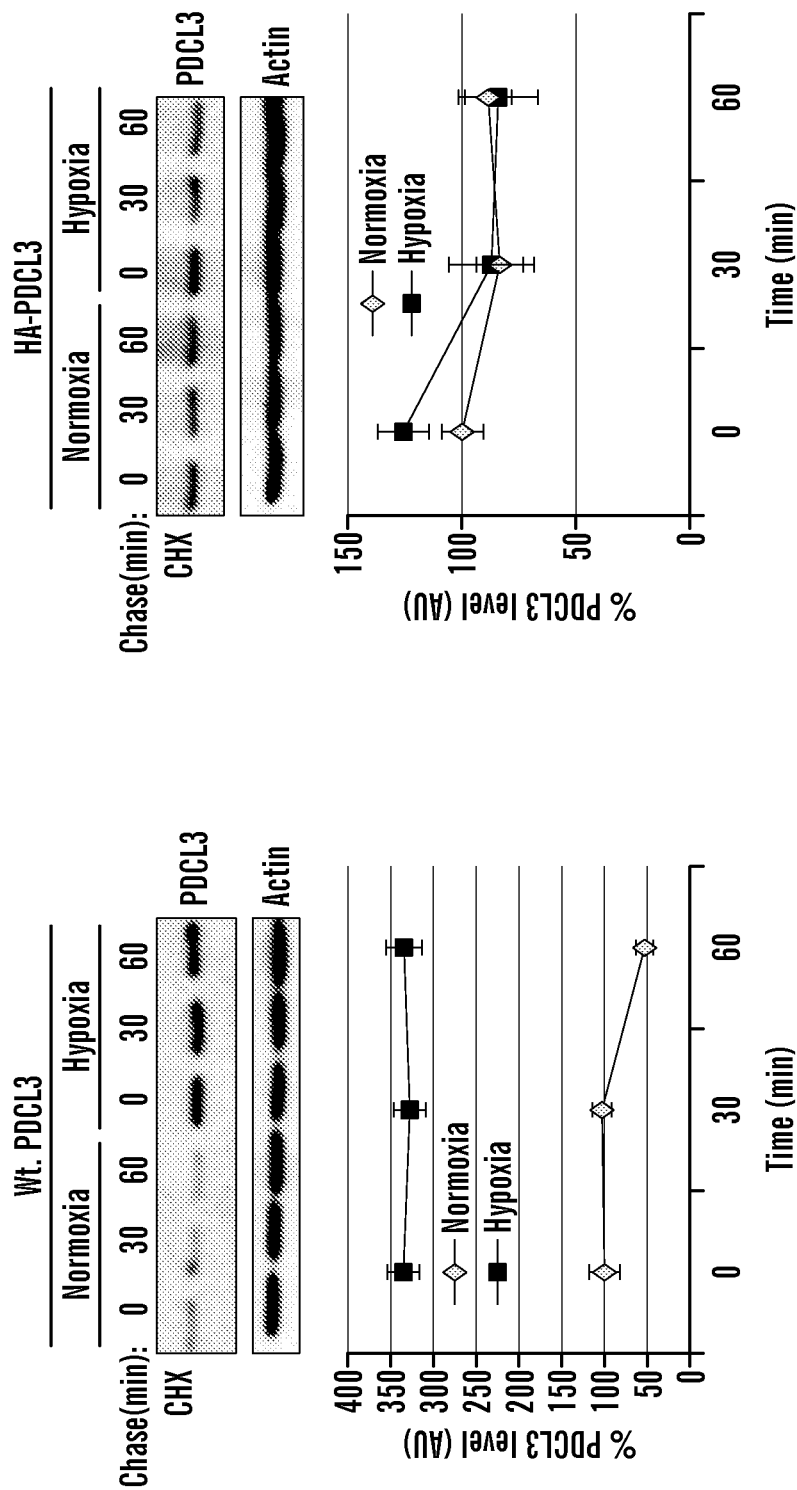
FIGS. 9A-9B demonstrate that blocking N-terminal methionine acetylation inhibits hypoxia-induced upregulation of PDCL3.

Exposure of endothelial cells to hypoxic environment (1% oxygen, 24 hours) significantly increased expression of PDCL3 (FIG. 4A). Similarly, expression of VEGFR-2 was also markedly increased in response to hypoxia (FIG. 4A). Likewise, treatment of cells with chemical hypoxia, cobalt chloride, similarly increased expression of PDCL3 and VEGFR-2 (FIGS. 9A-9B). The knockdown of PDCL3 reduced the hypoxia-mediated upregulation of VEGFR-2 (FIG. 4B).

Figure 4C:
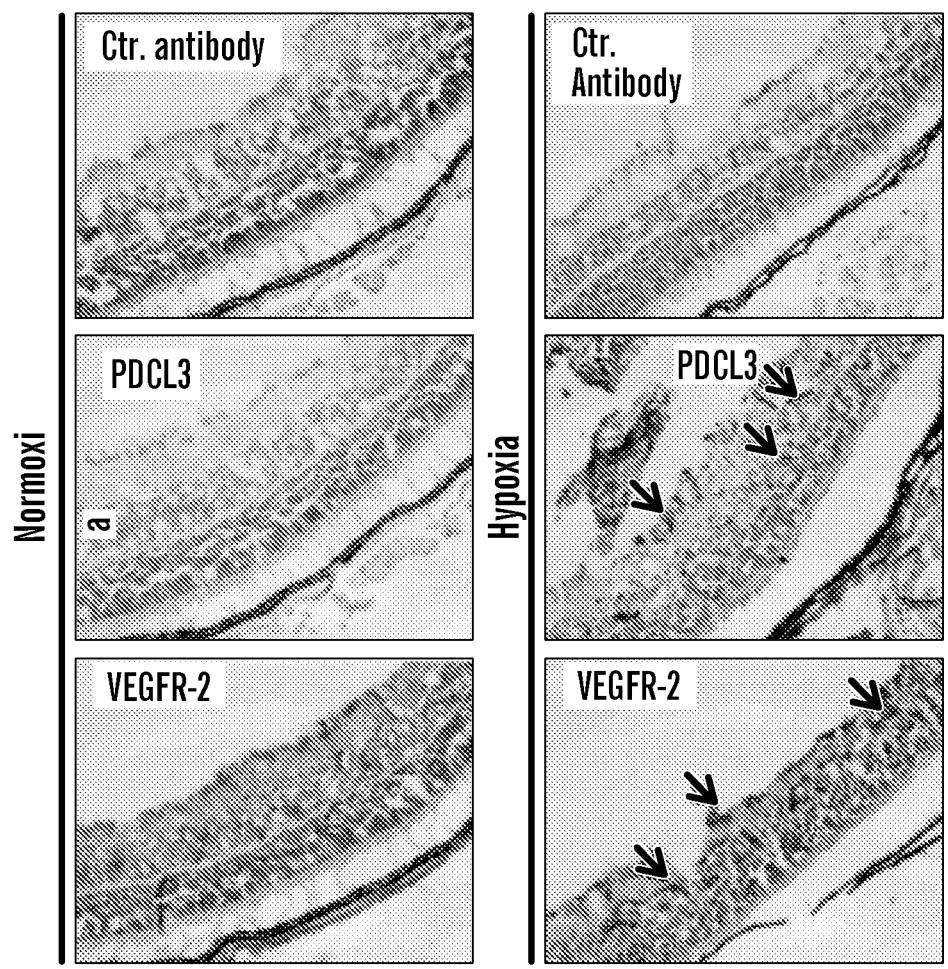

To examine the effect of hypoxia on the expression of PDCL3 in vivo, expression of PDCL3 in a well-characterized mouse model of hypoxia-induced angiogenesis was examined[40]. Immunohistochemistry analysis of ocular tissues showed that the expression of PDCL3 is highly upregulated in response to hypoxia particularly in the blood vessels of the retina (FIG. 4C), whereas its expression was relatively undetectable in normal mouse retinal tissue (FIG. 4C). Expression of VEGFR-2 also was significantly higher in the mouse ocular tissue exposed to hypoxia (FIG. 4C). The data demonstrate that hypoxia affects expression of PDCL3 and that up-regulation of PDCL3, in part, contributes to increased expression of VEGFR-2.

Accordingly, provided herein, in some aspects, are PDCL3 antagonist agents that inhibit VEGFR-2 binding to endogenous PDCL3 for the inhibition of angiogenesis and angiogenesis-mediated disorders. In some embodiments of these aspects and all such aspects described herein, the PDCL3 antagonist agents specifically bind to the VEGFR-2 binding site, and inhibit endogenous PDCL3 binding to VEGFR-2, as described herein.

The terms "VEGFR-2" or "KDR," as used herein, refers to the 1356 amino acid polypeptide having the amino acid sequence of: MQSKVLLAVALWLCVE-TRAASVGLPSVSLDLPRLSIQKDILTIKANTTLQITC-RGQRDLDWL WPNNQSGSEQRVEVTECSDGLFCKTL-TIPKVIGNDTGAYKCFYRETDLASVIYVYVQDYRSP FIASVSDQHGVVYITENKNKTVVIPCLGSISNLNVSL-CARYPEKRFVPDGNRISWDSKKGFTIP SYMISY-AGMVFCEAKINDESYQSIMYIVVVVGYRIYDVVLSP-SHGIELSVGEKLVLNCTARTE LNVGIDFNWEYPSS-KHQHKKLVNRDLKTQSGSEMKKFLSTLTIDGVTRS-DQGLYTCAASSGL MTKKNSTFVRVHEKPFVAFGS-GMESLVEATVGERVRIPAKYLGYPPPEIKWYKN-GIPLESNH TIKAGHVLTIMEVSERDTGNYTVILTN-PISKEKQSHVVSLVVYVPPQIGEKSLISPVDSYQYGT TQTLTCTVYAIPPPHHIHWYWQLEEECANEPSQA-VSVTNPYPCEEWRSVEDFQGGNKIEVNK NQFA-LIEGKNKTVSTLVIQAANVSALYKCEAVNKVGRG-ERVISFHVTRGPEITLQPDMQPTEQ ESVSLWC-TADRSTFENLTWYKLGPQPLPIHVGELPTPVCK-NLDTLWKLNATMFSNSTNDILI MELKNASLQDQ-GDYVCLAQDRKTKKRHCVVRQLTVLERVAPTITGN-LENQTTSIGESIEVSC TASGNPPPQIMWFKDNETLV-EDSGIVLKDGNRNLTIRRVRKEDEGLYTCQACS-VLGCAKVEA FFIIEGAQEKTNLEIIILVGTAVIAMF-FWLLLVIILRTVKRANGGELKTGYLSIVMDPDELPL-DE HCERLPYDASKWEFPRDRLKLGKPLGRGAFGQ-VIEADAFGIDKTATCRTVAVKMLKEGATH SEHRALM-SELKILIHIGHHLNVVNLLGACTKPGGPLMVIVE-FCKFGNLSTYLRSKRNEFVPYK TKGARFRQGKDYV-GAIPVDLKRRLDSITSSQSSASSGFVEEKSLSDVEEEE-APEDLYKDFLTLE HLICYSFQVAKGMEFLAS-RKCIHRDLAARNILLSEKNVVKICDFGLARDIYKDP-DYVRKGDA RLPLKWMAPETIFDRVYTIQSDVW-SFGVLLWEIFSLGASPYPGVKIDEEFCRRLKEGTRM-RAP DYTTPEMYQTMLDCWHGEPSQRPTFSELVEH-LGNLLQANAQQDGKDYIVLPISETLSMEEDS GLSLPTSPVSCMEEEEVCDPKFHYDNTAG-ISQYLQNSKRKSRPVSVKTFEDIPLEEPEVKVIPD DNQTDSGMVLASEELKTLEDRTKLSPSFGGMVPSKS-RESVASEGSNQTSGYQSGYHSDDTDT TVYSSEEAEL-LKLIEIGVQTGSTAQILQPDSGTTLSSPPV (SEQ ID NO: 7), as described by, e.g., NP_002244.1, and encoded by, e.g., NM_002253.2 (SEQ ID NO: 8), together with any naturally occurring allelic, splice variants, and naturally occurring processed forms thereof. Typically, VEGFR-2 refers to human VEGFR-2. The terms "VEGFR-2" or "KDR" are also used to refer to truncated forms or fragments of the VEGFR-2 polypeptide having a desired VEGFR-2 activity. Reference to any such forms or fragments of VEGFR-2 can be identified in the application, e.g., by "VEGFR-2 (1-1204), or "VEGFR-2Δ152" Specific residues of VEGFR-2 can be referred to as, for example, "VEGFR-2 (62)."

A PDCL3 "VEGFR-2 binding site," as used herein, refers to a PDCL3 amino acid sequence to which VEGFR-2 binds or associates. VEGFR-2 associates with PDCL3 via its juxtamembrane domain. By preventing association of VEGFR-2 to the VEGFR-2 binding site of PDCL3 using a PDCL3 antagonist agent, as described herein, VEGFR-2 is not stabilized and undergoes ubiquitin-mediated degradation, and therefore VEGFR-2 mediated signaling and angiogenesis is inhibited. Accordingly, in some embodiments, the PDCL3 antagonist agent prevents the association between the VEGFR-2 juxtamembrane domain and the PDCL3 VEGFR-2 binding site.

Anti-PDCL3 Antagonist Agents

As demonstrated herein, inhibition of PDCL3 expression and/or activity inhibits angiogenesis and angiogenic-mediated disorders, in part due to PDCL3's interaction with VEGFR-2, regulation of VEGFR-2 degradation, and potentiation of ligand-mediated activation of VEGFR-2 and VEGFR-2 signaling. VEGFR-2 is an important drug target for treatment of a variety of disorders, including cancer and age-related macular degeneration. As described herein, PDCL3 (phosducin like 3) has a novel role in the stabilization of VEGFR-2 by serving as a VEGFR-2 chaperone protein. PDCL3 co-localizes with VEGFR-2 in cells and recognizes the juxtamembrane domain of VEGFR-2. Upregulation of PDCL3 expression also markedly increases ligand-mediated tyrosine phosphorylation of VEGFR-2 and activation of VEGFR-2-associated signaling proteins. Further, as demonstrated herein, PDCL3 activity is required for endothelial cell proliferation and capillary tube formation of primary endothelial cells and angiogenesis in developing zebrafish embryos. PDCL3 elicits its activity, in part, by rendering VEGFR-2 to a more stable protein and preventing its ubiquitylation and proteolytic degradation.

Accordingly, provided herein, in various aspects, are compositions comprising PDCL3 antagonist agents, such as polypeptides, antibodies or antigen-binding fragments thereof, nucleic acids, and small molecules, for inhibiting PDCL3 and VEGFR-2 interactions, and methods of use thereof for inhibition of angiogenesis and pathologies associated with aberrant angiogenesis.

As used herein, a "PDCL3 antagonist agent" or "PDCL3 antagonist" refer to an agent, such as a small molecule, antagonist polypeptide, inhibitory nucleic acid, or PDCL3-specific antibody or antigen-binding fragment thereof, that inhibits or causes or facilitates a qualitative or quantitative inhibition, decrease, or reduction in one or more processes, mechanisms, effects, responses, functions, activities or pathways mediated by PDCL3. Thus, the term PDCL3 antagonist agent refers to an agent that inhibits expression of the PDCL3 polypeptide or polynucleotide encoding PDCL3, or one that binds to, partially or totally blocks stimulation, decreases, prevents, delays activation, inactivates, desensitizes, or down regulates the activity of the PDCL3 polypeptide or polynucleotide encoding PDCL3. Such PDCL3 antagonists can e.g., inhibit PDCL3 expression, e.g., PDCL3 translation, post-translational processing of PDCL3, stability, degradation, or nuclear or cytoplasmic localization of the PDCL3 polypeptide, or transcription, post transcriptional processing, stability or degradation of a polynucleotide encoding PDCL3, or, partially or totally block VEGFR-2 binding to PDCL3. In some embodiments of these aspects and all such aspects described herein, a PDCL3 antagonist agent has no effect on the activity or expression of other Phosducin-like proteins (PhLPs), such as PhLP1 or PhLP2.

The term "agent" as used herein in reference to a PDCL3 antagonist agent means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, siRNAs, lipoproteins, aptamers, and modifications and combinations thereof etc. In some embodiments, agents are small molecules having a chemical moiety. For example, chemical moieties include unsubstituted or substituted alkyl, aromatic, or heterocyclyl moieties. Compounds can be known to have a desired activity and/or property, e.g., inhibit PDCL3 activity, or can be selected from a library of diverse compounds, using, for example, screening methods, such as the high-throughput screening methods demonstrated herein.

Anti-PDCL3 Antagonist Polypeptides

In some aspects, provided herein are compositions comprising PDCL3 antagonist polypeptides that inhibit endogenous PDCL3-VEGFR-2 interactions to inhibit or reduce VEGFR-2 stability and thereby inhibit VEGR-2 mediated signaling and angiogenesis. In some such embodiments, the PDCL3 antagonist polypeptide specifically binds VEGFR-2. As used herein, the term "PDCL-3" refers to a family of PDCL3 proteins from any species, such as human PDCL3 (SEQ ID NO: 1) and variants derived from such PDCL3 proteins by mutagenesis or other modification(s). Reference to PDCL3 herein is understood to be a reference to any one of the currently identified forms. Members of the PDCL-3 family belong to a conserved family of proteins with thioredoxin-like domains that were initially identified as modulators of G protein signaling, and have an N-terminal helical domain or "coil-coil domain," a central thioredoxin-like domain, and a charged carboxyl terminus.

The term "PDCL3 antagonist polypeptide," as used herein, includes polypeptides comprising any naturally occurring polypeptide of a PDCL3 family member as well as any variants thereof (including mutants, fragments, fusions, and peptidomimetic forms) that retain a useful activity, such as inhibition of VEGFR-2 mediated signaling and/or angiogenesis. For example, PDCL3 antagonist polypeptides include polypeptides derived from the sequence of any known PDCL3 having a sequence at least about 70% identical to the sequence of a PDCL3 polypeptide, and preferably at least 75%, at least 80%, at least 85%, at least 90%, at least 95%, at least 97%, at least 98%, at least 99%, or more identity. For example, a PDCL3 antagonist polypeptide described herein can bind to and inhibit the function of an endogenous PDCL3 protein and/or inhibit the function of VEGFR-2. Preferably, a PDCL3 antagonist polypeptide that antagonizes VEGFR-2 signaling pathways inhibits angiogenesis. Assays and methods to measure the activity of a given PDCL3 antagonist polypeptide, such as inhibition of VEGFR-2 mediated signaling and/or angiogenesis, are known in the art, and non-limiting assays and methods are provided herein in the Examples.

Accordingly, in some aspects, provided herein are PDCL3 antagonist polypeptides that reduce or inhibit VEGFR-2 mediated activity. In some embodiments of these aspects and all such aspects described herein, a PDCL3 antagonist polypeptide specifically binds to VEGFR-2 and prevents binding of VEGFR-2 to endogenous PDCL3. In some embodiments of these aspects and all such aspects described herein, a PDCL3 antagonist polypeptide comprises a PDCL3 coil-coil domain. In some embodiments of these aspects and all such aspects described herein, a PDCL3 antagonist polypeptide comprises a PDCL3 thioredoxin domain. In some embodiments, of these aspects, and all such aspects described herein, a PDCL3 antagonist polypeptide comprises a PDCL3 C-terminal domain. In some embodiments of these aspects and all such aspects described herein, a PDCL3 antagonist polypeptide comprises a PDCL3 coil-coil domain and a PDCL3 thioredoxin domain. In some embodiments, of these aspects, and all such aspects described herein, a PDCL3 antagonist polypeptide comprises a PDCL3 thioredoxin domain and a PDCL3 C-terminal domain.

In some embodiments of these aspects and all such aspects described herein, a PDCL3 antagonist polypeptide comprises a coiled-coiled domain having the amino acid sequence of: MQDPNADTEWNDILRKKGIL-PPKESLKELEEEAEEEQRILQQSVVKTYED (SEQ ID NO: 9), or a portion, fragment, or derivative thereof, that inhibits VEGFR-2 activity and/or inhibits angiogenesis.

VEGFR-2 inhibition activity can be determined using techniques known in the art, and as provided herein in the Examples. For example, VEGFR-2 antagonist activity can be determined by looking at a wild type VEGFR-2 activity and comparing the inhibition or reduction of such activity when the PDCL3 antagonist polypeptide is used. The polypeptide of SEQ ID NO: 9 can be used as a standard or control. One can use any assay to measure inhibition of VEGFR-2 activity. For example, one can use the human umbilical vein endothelial cell (HUVEC) in vitro angiogenesis assay and in vitro proliferation assay as set forth below in the Examples. Other assays include in vitro tubulogenesis assays, and determination of changes in parameters, such as, for example, mean total tube number, mean total tube length, mean number of branching points, and/or mean number of vessel connections using such in vitro tubulogenesis assays.

Preferably, a PDCL3 antagonist polypeptide results in about at least a 10% or more, at least a 15% or more, at least 20% or more, at least a 25% or more, at least a 30% or more, at least a 35% or more, at least a 40% or more, at least a 45% or more, at least a 50% or more, at least a 55% or more, at least a 60% or more, at least a 65% or more, at least a 70% or more, at least a 75% or more, at least a 80% or more, at least a 85% or more, at least a 90% or more, at least a 95% or more, or at least 100% or complete inhibition of VEGFR-2 activity in comparison to a reference or control level in the absence of the PDCL3 antagonist polypeptide. Inhibition of VEGFR-2 activity can also be determined by inhibition of binding of VEGFR-2 to endogenous PDCL3, inhibition of VEGFR-2 phosphorylation, increase in VEGFR-2 ubiquitylation, and/or increase in VEGFR-2 degradation, as set forth herein below in the Examples.

The ability of PDCL3 antagonist polypeptides to influence angiogenesis can also be determined using a number of know in vivo and in vitro assays. Such assays are disclosed in Jain et al., Nature Medicine 3, 1203-1 208 (1997), the disclosure of which is herein incorporated by reference in ites entirety. For example, assays for the ability to inhibit angiogenesis in vivo include chick chorioallantoic membrane assays and mouse, rat or rabbit corneal pocket assays, see, for example, Polverini et al., 1991, Methods Enzymol. 198: 440-450, as well as embryonic angiogenesis assays as provided herein in the Examples.

As used herein, a "variant" or "derivative" of a PDCL3 antagonist polypeptide is a polypeptide in which one or more physical, chemical, or biological properties has been altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which can result in changes in primary, secondary or tertiary structure. In some embodiments, a PDCL3 antagonist polypeptide derivative comprises a functionally active fragment of PDCL3. However, as used herein, any such PDCL3 antagonist polypeptide derivative or fragment thereof exhibit at least one of the aforementioned VEGFR-2 antagonist or angiogenesis inhibiting activities.

Functionally active fragments of PDCL3 antagonist polypeptides can be obtained by screening polypeptides recombinantly produced from the corresponding fragment of the nucleic acid encoding a PDCL3 antagonist polypeptide, such as for example, that encoded by SEQ ID NO: 9. In addition, fragments can be chemically synthesized using techniques known in the art such as conventional Merrifield solid phase f-Moc or t-Boc chemistry. The PDCL3 antagonist fragments can be produced (recombinantly or by chemical synthesis) and tested to identify those fragments that can function as antagonists (inhibitors) of PDCL3 protein or signaling mediated by VEGFR-2.

In some embodiments of these aspects and all such aspects described herein, a functional fragment of a PDCL3 antagonist polypeptide comprises an amino acid sequence that is at least 75% identical to the amino acid sequence of SEQ ID NO: 9. In some embodiments, the functional fragment has an amino acid sequence at least 80%, 85%, 90%, 95%, 97%, 98%, 99% or 100% identical to the amino acid sequence of SEQ ID NO: 9.

Functional variants or derivatives of a PDCL3 antagonist polypeptide can be generated by modifying the structure of a PDCL3 antagonist polypeptide for such purposes as enhancing therapeutic efficacy, or stability (e.g., ex vivo shelf life and resistance to proteolytic degradation in vivo). Such modified PDCL3 antagonist polypeptide, when selected to retain VEGR-2 inhibitory activity and binding, are considered functional equivalents of the PDCL3 antagonist polypeptide of SEQ ID NO: 9, for example. Modified PDCL3 antagonist polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

Naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Preferred conservative substitutions for use in the PDCL3 antagonist polypeptides described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Whether a change in the amino acid sequence of an PDCL3 antagonist polypeptide results in a functional variant can be readily determined by assessing the ability of the variant PDCL3 polypeptide to produce an inhibitory activity similar to a known PDCL3 antagonist polypeptide, such as that of SEQ ID NO: 9.

In certain embodiments, specific mutations of PDCL3 antagonist polypeptides can be introduced so as to alter the glycosylation of the polypeptide. Such mutations can be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration can also be made by the addition of, or substitution by, one or more serine or threonine residues to the sequence of the wild-type PDCL3 polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a PDCL3 antagonist polypeptide is by chemical or enzymatic coupling of glycosides to the PDCL3 antagonist polypeptide. Depending on the coupling mode used, the sugar(s) can be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a PDCL3 antagonist polypeptide can also be accomplished chemically and/or enzymatically. Chemical deglycosylation can involve, for example, exposure of the PDCL3 antagonist polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on PDCL3 antagonist polypeptides can be achieved by the use of a variety of endo- and exo-glycosidases as described by Thotakura et al. (1987) Meth. Enzymol. 138:350. The sequence of a PDCL3 antagonist polypeptide can be adjusted, as appropriate, depending on the type of expression system used, as mammalian, yeast, insect and plant cells can all introduce differing glycosylation patterns that can be affected by the amino acid sequence of the peptide. In general, PDCL3 antagonist proteins for use in humans will be expressed in a mammalian cell line that provides proper glycosylation, such as HEK293 or CHO cell lines, although other mammalian expression cell lines, yeast cell lines with engineered glycosylation enzymes and insect cells are expected to be useful as well.

Mutagenesis techniques can be used to give rise to PDCL3 antagonist polypeptide variants that have intracellular half-lives dramatically different than the corresponding PDCL3 antagonist polypeptide. For example, the altered protein can be rendered either more stable or less stable to proteolytic degradation or other cellular processes which result in destruction of, or otherwise inactivation of the PDCL3 antagonist polypeptide. Such variants, can for example have increased or decreased half-lives relative to the starting PDCL3 antagonist polypeptide. A PDCL3 antagonist polypeptide having a shorter half-life can give rise to more transient biological effects and can allow tighter control of recombinant PDCL3 antagonist polypeptide levels within the patient. In some embodiments, a fusion protein can be generated, such as an Fc fusion protein with a PDCL3 antagonist polypeptide, such that mutations can be made in the linker (if any) and/or the Fc portion to alter the half-life of the PDCL3 antagonist fusion polypeptide.

A combinatorial library can be produced by way of a degenerate library of genes encoding a library of polypeptides which each include at least a portion of potential PDCL3 antagonist polypeptide sequences. For instance, a mixture of synthetic oligonucleotides can be enzymatically ligated into gene sequences such that the degenerate set of potential PDCL3 antagonist polypeptide sequences are expressible as individual polypeptides, or alternatively, as a set of larger fusion proteins (e.g., for phage display). There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, PDCL3 antagonist polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of PDCL3 antagonist polypeptide.

In certain embodiments, the PDCL3 antagonist polypeptide for use in the compositions and methods described herein can further comprise post-translational modifications in addition to any that are naturally present in the PDCL3 antagonist polypeptide. Such modifications include, but are not limited to, acetylation, carboxylation, glycosylation, phosphorylation, lipidation, and acylation. As a result, the modified PDCL3 antagonist polypeptide can contain non-amino acid elements, such as polyethylene glycols, lipids, poly- or mono-saccharide, and phosphates. Effects of such non-amino acid elements on the functionality of a PDCL3 antagonist polypeptide can be tested as described herein for other PDCL3 antagonist polypeptide variants. When a PDCL3 antagonist polypeptide is produced in cells by cleaving a nascent form of the PDCL3 antagonist polypeptide, post-translational processing can also be important for correct folding and/or function of the protein. Different cells (such as CHO, HeLa, MDCK, 293, WI38, NIH-3T3 or HEK293) have specific cellular machinery and characteristic mechanisms for such post-translational activities and can be chosen to ensure the correct modification and processing of the PDCL3 antagonist polypeptides.

In some embodiments of the aspects pertaining to PDCL3 antagonist polypeptides described herein, functional variants or modified forms of the PDCL3 antagonist polypeptide for use herein include fusion proteins having at least a portion of the PDCL3 antagonist polypeptide and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain can be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6 (SEQ ID NO: 13)) fusion partners. As another example, a fusion domain can be selected so as to facilitate detection of the PDCL3 antagonist polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a PDCL3 antagonist polypeptide is fused with a domain that stabilizes the polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

It is also understood that different elements of the fusion proteins can be arranged in any manner that is consistent with the desired functionality. For example, a PDCL3 antagonist polypeptide can be placed C-terminal to a heterologous domain, or, alternatively, a heterologous domain can be placed C-terminal to a PDCL3 antagonist polypeptide. The PDCL3 antagonist polypeptide domain and the heterologous domain need not be adjacent in a fusion protein, and additional domains or amino acid sequences can be included C- or N-terminal to either domain or between the domains.

In certain embodiments, the PDCL3 antagonist polypeptides for use in the compositions and methods described herein comprise one or more modifications that are capable of stabilizing the PDCL3 antagonist polypeptides. For example, such modifications can enhance the in vitro half life of the PDCL3 antagonist polypeptides, enhance circulatory half life of the PDCL3 antagonist polypeptides, or reduce proteolytic degradation of the PDCL3 antagonist polypeptides. Such stabilizing modifications include, but are not limited to, fusion proteins (including, for example, fusion proteins comprising an PDCL3 antagonist polypeptide and a stabilizer domain), N-terminal acetylation, modifications of a glycosylation site (including, for example, addition of a glycosylation site to a PDCL3 antagonist polypeptide), and modifications of carbohydrate moiety (including, for example, removal of carbohydrate moieties from an PDCL3 antagonist polypeptide). In the case of fusion proteins, a PDCL3 antagonist polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

Nucleic Acid Inhibitors of PDCL3

In some embodiments of the compositions and methods described herein, a PDCL3 antagonist agent is an RNA interference agent that specifically targets PDCL3 and can be used for the inhibition of expression of PDCL3 in vivo. RNA interference (RNAi) uses small interfering RNA (siRNA) duplexes that target the messenger RNA encoding a target polypeptide for selective degradation and is a powerful approach for inhibiting the expression of selected target polypeptides. siRNA-dependent post-transcriptional silencing of gene expression involves cleaving the target messenger RNA molecule at a site guided by the siRNA. "RNA interference (RNAi)," as used herein, refers to the evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In some embodiments, the RNA interference agent or siRNA is a double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, at least 20%, at least 30%, at least 40%, at least 50%, at least 60%, at least 70%, at least 80%, at least 90%, at least 95%, or at least 99% or more as compared to the expression of a target gene or the activity or level of the protein encoded by a target gene which has not been targeted by an RNA interfering agent.

As used herein, siRNAs also include small hairpin (also called stem loop) RNAs (shRNAs). In some embodiments, these shRNAs are composed of a short (e.g., about 19 to about 25 nucleotide) antisense strand, followed by a nucleotide loop of about 5 to about 9 nucleotides, and the analogous sense strand. Alternatively, in other embodiments, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent can be a cellular gene or genomic sequence, e.g., the human PDCL3 genomic sequence. An siRNA can be substantially homologous to the target gene or genomic sequence, or a fragment thereof, i.e., the PDCL3 gene or mRNA. As used in this context, the term "homologous" is defined as being substantially identical, sufficiently complementary, or similar to the target PDCL3 mRNA, or a fragment thereof, to effect RNA interference of the target PDCL3. In addition to native RNA molecules, RNA suitable for inhibiting or interfering with the expression of a target sequence include RNA derivatives and analogs. Preferably, the siRNA is identical to its target. The siRNA preferably targets only one sequence.

Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one can also screen the potential target sequences for similar sequences in the sequence databases to identify potential sequences which may have off-target effects. For example, according to Jackson et al. (Id.), 15, or perhaps as few as 11 contiguous nucleotides, of sequence identity are sufficient to direct silencing of non-targeted transcripts. Therefore, one can initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human PDCL3 mRNA.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence may be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents that effectively target PDCL3 mRNA, including an siRNA (sc-94814) purchased from Santa Cruz Inc., and assays for testing their PDCL3 inhibitory activity.

In some embodiments, the RNA interference agent targeting PDCL3 is delivered or administered in a pharmaceutically acceptable carrier. Additional carrier agents, such as liposomes, can be added to the pharmaceutically acceptable carrier. In another embodiment, the RNA interference agent is delivered by a vector encoding the small hairpin RNA (shRNA) in a pharmaceutically acceptable carrier to the cells in an organ of an individual. The shRNA is converted by the cells after transcription into siRNA capable of targeting PDCL3.

In some embodiments, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods described herein, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs targeting PDCL3 described herein, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting PDCL3 mRNA, can be delivered singly, or in combination with other RNA interference agents, e.g., siRNAs, such as, for example siRNAs directed to other cellular genes.

Synthetic siRNA molecules, including shRNA molecules, can be generated using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule for use in the compositions and methods described herein can be selected from a given target gene sequence, e.g., a PDCL3 coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule for use in the compositions and methods described herein involves identifying a 23 nucleotide sequence motif AA(N19)TT (SEQ. ID. NO: 11) (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as OLIGO-ENGINE®, can also be used to select siRNA sequences against EST libraries to ensure that only one gene is targeted.

Delivery of RNA Interfering Agents

Methods of delivering RNA interference agents, e.g., an siRNA, or vectors containing an RNA interference agent, to the target cells, e.g., lymphocytes or other desired target cells, for uptake include injection of a composition containing the RNA interference agent, e.g., an siRNA targeting PDCL3, or directly contacting the cell, e.g., a lymphocyte, with a composition comprising an RNA interference agent, e.g., an siRNA targeting PDCL3. In other embodiments, an RNA interference agent, e.g., an siRNA targeting PDCL3, can be injected directly into any blood vessel, such as vein, artery, venule or arteriole, via, e.g., hydrodynamic injection or catheterization. Administration can be by a single injection or by two or more injections. The RNA interference agent is delivered in a pharmaceutically acceptable carrier. One or more RNA interference agents can be used simultaneously. In some preferred embodiments, only one siRNA that targets human PDCL3 is used.

In some embodiments, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents targeting PDCL3, e.g., the siRNAs or shRNAs, can be introduced along with components that perform one or more of the following activities: enhance uptake of the RNA interfering agents, e.g., siRNA, by the cell, e.g., lymphocytes or other cells; inhibit annealing of single strands; stabilize single strands; or otherwise facilitate delivery to the target cell and increase inhibition of the target PDCL3. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

PDCL3 Antagonist Antibodies and Antigen-Binding Fragments Thereof

Also provided herein, in some aspects, are compositions comprising PDCL3 antagonist antibodies that specifically bind PDCL3 and inhibit endogenous PDCL3-VEGFR-2 interactions to inhibit or reduce VEGFR-2 stability and thereby inhibit VEGR-2 mediated signaling and angiogenesis. PDCL3 antibody antagonists for use in the composition and methods described herein include complete immunoglobulins, antigen binding fragments of immunoglobulins, as well as antigen-binding fragments that comprise antigen binding domains of immunoglobulins. As used herein, "antigen-binding fragments" of immunoglobulins include, for example, Fab, Fab', F(ab')2, scFv and dAbs. Modified antibody formats have been developed which retain binding specificity, but have other characteristics that can be desirable, including for example, bispecificity, multivalence (more than two binding sites), and compact size (e.g., binding domains alone).

As antibodies can be modified in a number of ways, the term "antibody" should be construed as covering any specific binding member or substance having a binding domain with the required specificity for PDCL3. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

Accordingly, in some aspects, provided herein are PDCL3 antagonist antibodies or antibody fragments thereof that are specific for PDCL3, wherein the PDCL3 antagonist antibodies or antibody fragments thereof thereof specifically binds to PDCL3 and reduces or inhibits PDCL3 biological activity. In some embodiments, PDCL3 is human PDCL3. In some embodiments, PDCL3 has a sequence comprising SEQ ID NO: 1 or an allelic or splice variant thereof.

As used herein, a "PDCL3 antibody" is an antibody that binds to PDCL3 with sufficient affinity and specificity. The antibody selected will normally have a binding affinity for PDCL3, for example, the antibody can bind human PDCL3 with a $K_D$ value between $10^{-5}$ M to $10^{-10}$ M. Antibody affinities can be determined, for example, by a surface plasmon resonance based assay (such as the BIAcore assay described in PCT Application Publication No. WO2005/012359); enzyme-linked immunoabsorbent assay (ELISA); and competition assays (e.g. RIA's), for example. In certain aspects described herein, a PDCL3 antibody can be used as a therapeutic agent in targeting and interfering with diseases or conditions where PDCL3 activity is involved. Also, a PDCL3 antibody can be subjected to other biological activity assays, e.g., in order to evaluate its effectiveness as a therapeutic, or its effectiveness as a diagnostic aid, etc. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). Other biological activity assays that can be used to assess a PDCL3 antibody are described in the Examples section in regard to PDCL3 antagonist polypeptides.

As used herein, a "blocking" antibody or an antibody "antagonist" is one which inhibits or reduces biological activity of the antigen it binds. For example, a PDCL3 antagonist antibody binds PDCL3 and inhibits the ability of PDCL3 to, for example, bind VEGFR-2 and induce angiogenesis, to induce vascular endothelial cell proliferation or to induce vascular permeability. In certain embodiments, blocking antibodies or antagonist antibodies completely inhibit the biological activity of PDCL3.

Thus, PDCL3 antibodies or antibody fragments thereof that are useful in the compositions and methods described herein include any antibodies or antibody fragments thereof that bind with sufficient affinity and specificity to PDCL3, i.e., are specific for PDCL3, and can reduce or inhibit the biological activity of PDCL3, specifically the VEGFR-2 stabilizing activity of PDCL3.

Accordingly, in some embodiments of these aspects, an antibody or antibody fragment thereof that binds to PDCL3 and inhibits PDCL3 biological activity and blocks interaction of PDCL3 with VEGFR-2. In some such embodiments, the VEGFR-2 has a sequence comprising the sequence of SEQ ID NO: 7. In some embodiments, the antibody or antibody fragment thereof is specific for an epitope of PDCL3 comprising a coil-coil domain portion of PDCL3, such as, for example, SEQ ID NO: 9.

As described herein, an "antigen" is a molecule that is bound by a binding site on a polypeptide agent, such as an antibody or antibody fragment thereof. Typically, antigens are bound by antibody ligands and are capable of raising an antibody response in vivo. An antigen can be a polypeptide, protein, nucleic acid or other molecule. In the case of conventional antibodies and fragments thereof, the antibody binding site as defined by the variable loops (L1, L2, L3 and H1, H2, H3) is capable of binding to the antigen.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

In some embodiments of the aspects described herein, a PDCL3 antagonist antibody is a monoclonal antibody. The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or can be made by recombinant DNA methods (see, e.g., U.S. Pat. No. 4,816,567). The "monoclonal antibodies" can also be isolated from phage antibody libraries using the techniques described in Clackson et al., Nature 352:624-628 (1991) or Marks et al., J. Mol. Biol. 222:581-597 (1991), for example.

The PDCL3 antagonist monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al., Proc. Natl. Acad. Sci. USA 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

As used herein, a "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous mouse immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody can be prepared via immortalization of human B lymphocytes producing an antibody directed against a target antigen (such B lymphocytes can be recovered from an individual or can have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

In other embodiments of these aspects, the PDCL3 antagonist antibody is a PDCL3-specific antibody fragment. The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$—$C_H1$-$V_H$—$C_H1$) which, together with complementary light chain polypeptides, form a pair of antigen binding regions (Zapata et al. Protein Eng. 8(10):1057-1062 (1995); and U.S. Pat. No. 5,641,870).

Accordingly, in some such embodiments, the PDCL3 antagonist antibody fragment is a Fab fragment comprising $V_L$, $C_L$, $V_H$ and $C_H1$ domains. In some embodiments, the PDCL3 antagonist antibody fragment is a Fab' fragment, which is a Fab fragment having one or more cysteine residues at the C-terminus of the $C_H1$ domain. In some embodiments, the PDCL3 antagonist antibody fragment is a Fd fragment comprising $V_H$ and $C_H1$ domains. In some embodiments, the PDCL3 antagonist antibody is a Fd' fragment comprising $V_H$ and $C_H1$ domains and one or more cysteine residues at the C-terminus of the $C_{H1}$ domain. In some embodiments, the PDCL3 antagonist antibody fragment is a Fv fragment comprising the $V_L$ and $V_H$ domains of a single arm of an antibody. In some embodiments, the PDCL3 antagonist antibody fragment is a dAb fragment comprising a $V_H$ domain. In some embodiments, the PDCL3 antagonist antibody fragment comprises isolated CDR regions. In some embodiments, the human PDCL3 antagonist antibody fragment is a F(ab')$_2$ fragment, which comprises a bivalent fragment comprising two Fab' fragments linked by a disulphide bridge at the hinge region. In some embodiments, the PDCL3 antagonist antibody fragment is a single chain antibody molecule, such as a single chain Fv. In some embodiments, the PDCL3 antagonist antibody fragment is a diabody comprising two antigen binding sites, comprising a heavy chain variable domain ($V_H$) connected to a light chain variable domain ($V_L$) in the same polypeptide chain. In some embodiments, the PDCL3 antagonist antibody fragment is a linear antibody comprising a pair of tandem Fd segments ($V_H$—$C_H 1$-$V_H$—$C_H 1$) which, together with complementary light chain polypeptides, form a pair of antigen binding regions.

Antibodies to PDCL3 are commercially available and can be raised by one of skill in the art using well known methods. The PDCL3 inhibitory activity of a given antibody, or, for that matter, any PDCL3 antagonist, can be assessed using methods known in the art or described herein—to avoid doubt, an antibody or antibody fragment thereof that inhibits PDCL3 expression or activity useful in the compositions and methods described herein will inhibit VEGFR-2 binding to PDCL3 and/or VEGR-2 signaling activity. Antibody antagonists or inhibitors of PDCL3 for use in the composition and methods described herein can be obtained from commercial sources such as AbCam (Cambridge, Mass.), New England Biolabs (Ipswich, Mass.), Santa Cruz Biotechnologies (Santa Cruz, Calif.), Biovision (Mountain View, Calif.), R&D Systems (Minneapolis, Minn.), and Cell Signaling (Danvers, Mass.), among others. Antibodies can also be raised against a polypeptide or portion of a polypeptide by methods known to those skilled in the art. Antibodies are readily raised in animals such as rabbits or mice by immunization with the gene product or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., Eds., Antibodies: A Laboratory Manual, Cold Spring Harbor Laboratory, New York (1988), which is hereby incorporated by reference in its entirety. While both polyclonal and monoclonal antibody inhibitors of PDCL3 can be used in the methods described herein, it is preferred that a monoclonal antibody inhibitor of PDCL3 is used where conditions require increased specificity for a particular protein.

Other Antibody Modifications

In some embodiments of these aspects, amino acid sequence modification(s) of the antibodies or antibody fragments thereof specific for PDCL3 described herein are contemplated. For example, it can be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also can alter post-translational processes of the antibody, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated for use in the PDCL3 antagonist antibodies or antibody fragments thereof described herein.

Substantial modifications in the biological properties of the antibodies or antibody fragments thereof specific for PDCL3 are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids can be grouped according to similarities in the properties of their side chains (in A. L. Lehninger, in Biochemistry, second ed., pp. 73-75, Worth Publishers, New York (1975)): (1) nonpolar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Any cysteine residue not involved in maintaining the proper conformation of the PDCL3 antibodies or antibody fragments thereof can be substituted, generally with serine, to improve the oxidative stability of the molecule and prevent aberrant crosslinking Conversely, cysteine bond(s) can be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used.

Addition of glycosylation sites to the PDCL3 antibodies or antibody fragments thereof is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites).

Where the antibody comprises an Fc region, the carbohydrate attached thereto can be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

To increase the serum half life of PDCL3 antibodies described herein, one can incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

In other embodiments, the PDCL3 antibody or antibody fragment thereof can be conjugated to a "receptor" (such streptavidin) for utilization in tumor pretargeting wherein the antibody-receptor conjugate is administered to the subject, followed by removal of unbound conjugate from the circulation using a clearing agent and then administration of a "ligand" (e.g. avidin) which is conjugated to a cytotoxic agent (e.g. a radionucleotide).

The PDCL3 antibodies and antibody fragments thereof described herein can also be formulated as immunoliposomes, in some embodiments. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated, for example, by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the PDCL3 antibodies described herein can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19)1484 (1989)

Small Molecule Inhibitors of PDCL3

In some embodiments of the compositions and methods described herein, a PDCL3 antagonist agent is a small molecule antagonist or agent that specifically targets PDCL3 and can be used for the inhibition of expression or activity of PDCL3 in vivo for inhibiting pathological angiogenesis. Useful small molecule inhibitors include protein tyrosine kinase inhibitors, such as DAPH, Emodin, Sunitinib malate, GW2974, Tyrphostin AG 112, Tyrphostin 23, Tyrphostin 51, and I-Ome-Tyrophostin AG 538; inhibitors of vesicular catecholine and serotonin uptake, such as Reserpine; subtype selective retinoic acid receptor inhibitors, such as AC-93253 iodide; soluble guanylyl cyclase activator and aldose reductase inhibitors, such as Urapidil Hydrochloride; Nicotinic acetylcholine receptor antagonists, such as Mecamylamine hydrochloride; (−)-MK-801 hydrogen maleate; SIRT2 inhibitors, such as AGK2; and alpha1 Adrenoceptor antagonists, such as Isoliquiritgenin. 16 lead compounds within these above-mentioned groups were identified as PDCL3 inhibitors and their potency and efficacy in inhibition of PDCL3 was validated.

As demonstrated herein, novel small molecule inhibitors for PDCL3 were identified using high throughput screening. Given that PDCL3 plays a fundamental role in maturation and folding of receptor tyrosine kinases (RTKs), such as VEGFR-2, and considering that activity of these RTKs are cornerstone of tumor growth and metastasis, it was decided to screen for small molecule inhibitors that could antagonize PDCL3 function in tumor cells. LOPAC1280 (a library of Pharmacologically Active Compounds), which is a collection of 1,280 pharmacologically active compounds, was used. The library is most commonly used to validate new drug discovery assays and characterize orphan targets. 16 lead compounds were identified as PDCL3 inhibitors and their potency and efficacy in inhibition of PDCL3 was validated. The structures of these 16 lead compounds, namely, Reserpine, DAPH, AC-93253 iodide, Emodin, Sunitinib malate, GW2974, Urapidil Hydrochloride, Mecamylamine hydrochloride, (−)-MK-801 hydrogen maleate, AGK2, Tyrphostin AG 112, Tyrphostin 23, Tyrphostin 51, I-Ome-Tyrophostin AG 538, and Isoliquiritgenin are provided herein at FIG. 14B.

Accordingly, in some embodiments of the aspects described herein, the small molecule antagonist or agent that specifically targets or inhibits PDCL3 is selected from Reserpine, DAPH, AC-93253 iodide, Emodin, Sunitinib malate, GW2974, Urapidil Hydrochloride, Mecamylamine hydrochloride, (−)-MK-801 hydrogen maleate, AGK2, Tyrphostin AG 112, Tyrphostin 23, Tyrphostin 51, I-Ome-Tyrophostin AG 538, and Isoliquiritgenin.

In some embodiments of the aspects described herein, the small molecule antagonist or agent that specifically targets or inhibits PDCL3 is Reserpine (Methyl (3β,16β,17α,18β,20α)-11,17-dimethoxy-18-[(3,4,5-trimethoxybenzoyl)oxy] yohimban-16-carboxylate) or a derivative or analog thereof that can inhibit PDCL3, such as any of those described in U.S. Pat. Nos. 2,752,351, 2,788,309, 3,365,456, 2,883,384, or 3978065, the contents of which are herein incorporated by reference in their entireties.

In some embodiments of the aspects described herein, the small molecule antagonist or agent that specifically targets or inhibits PDCL3 is DAPH (5,6-Dianilino-1H-isoindole-1, 3(2H)-dione) or a derivative or analog thereof that can inhibit PDCL3.

In some embodiments of the aspects described herein, the small molecule antagonist or agent that specifically targets or inhibits PDCL3 is AC-93253 iodide (3-Ethyl-2-[(1E,3E)-3-(1,3,3-trimethyl-1,3-dihydro-2H-indol-2-ylidene)-1-propen-1-yl]-1,3-benzothiazol-3-ium iodide) or a derivative or analog thereof that can inhibit PDCL3.

In some embodiments of the aspects described herein, a a small molecule antagonist or agent that specifically targets or inhibits PDCL3 is Emodin (1,3,8-Trihydroxy-6-methyl-9,10-anthraquinone) or a derivative or analog thereof that can inhibit PDCL3, such as any of those described in U.S. Pat. No. 4,670,265 or 7,268,162, the contents of which are herein incorporated by reference in their entireties.

In some embodiments of the aspects described herein, the small molecule antagonist or agent that specifically targets or inhibits PDCL3 is Sunitinib malate ((2S)-2-Hydroxysuccinic acid-N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide (1:1)) or a derivative or analog thereof that can inhibit PDCL3, such as any of those described in U.S. Pat. Nos. 8,329,740, 8,703,967, or US Patent publication US20110257237, the contents of which are herein incorporated by reference in their entireties.

In some embodiments of the aspects described herein, the small molecule antagonist or agent that specifically targets or inhibits PDCL3 is GW2974 (N4-(1-Benzyl-1H-indazol-5-yl)-N6,N6-dimethylpyrido[3,4-d]pyrimidine-4,6-diamine) or a derivative or analog thereof that can inhibit PDCL3.

In some embodiments of the aspects described herein, the small molecule antagonist or agent that specifically targets or inhibits PDCL3 is Urapidil Hydrochloride (6-({3-[4-(2-Methoxyphenyl)-1-piperazinyl]propyl}amino)-1,3-dimethyl-2,4(1H,3H)-pyrimidinedione) or a derivative or analog thereof that can inhibit PDCL3, such as any of those described in U.S. Pat. No. 4,131,678 or EP0275444A1, the contents of which are herein incorporated by reference in their entireties.

In some embodiments of the aspects described herein, the small molecule antagonist or agent that specifically targets or inhibits PDCL3 is Mecamylamine hydrochloride (N,2,3,3-Tetramethylbicyclo[2.2.1]heptan-2-amine hydrochloride (1:1)) or a derivative or analog thereof that can inhibit PDCL3.

In some embodiments of the aspects described herein, the small molecule antagonist or agent that specifically targets or inhibits PDCL3 is (−)-MK-801 hydrogen maleate (1-Methyl-16-azatetracyclo[7.6.1.02,7.010,15]hexadeca-2,4,6,10,12,14-hexaene (2E)-2-butenedioate (1:1)) or a derivative or analog thereof that can inhibit PDCL3.

In some embodiments of the aspects described herein, the small molecule antagonist or agent that specifically targets or inhibits PDCL3 is AGK2 ((2E)-2-Cyano-3-[5-(2,5-dichlorophenyl)-2-furyl]-N-(5-quinolinyl)acrylamide) or a derivative or analog thereof that can inhibit PDCL3.

In some embodiments of the aspects described herein, the small molecule antagonist or agent that specifically targets or inhibits PDCL3 is Tyrphostin AG 112 ((3Z)-2-Amino-4-(4-hydroxyphenyl)-1,3-butadiene-1,1,3-tricarbonitrile) or a derivative or analog thereof that can inhibit PDCL3.

In some embodiments of the aspects described herein, the small molecule antagonist or agent that specifically targets or inhibits PDCL3 is Tyrphostin 23 ((3,4-Dihydroxybenzylidene)malononitrile) or a derivative or analog thereof that can inhibit PDCL3, such as any of those described in U.S. Pat. No. 5,217,999 or EP0614661A2 or WO1991016892A1, the contents of which are herein incorporated by reference in their entireties.

In some embodiments of the aspects described herein, the small molecule antagonist or agent that specifically targets or inhibits PDCL3 is Tyrphostin 51 ((3Z)-2-Amino-4-(3,4,5-trihydroxyphenyl)-1,3-butadiene-1,1,3-tricarbonitrile) or a derivative or analog thereof that can inhibit PDCL3.

In some embodiments of the aspects described herein, the small molecule antagonist or agent that specifically targets or inhibits PDCL3 is I-Ome-Tyrophostin AG 538 (α-Cyano-(3-methoxy-4-hydroxy-5-iodocinnamoyl)-(3',4'-dihydroxyphenyl)ketone or a derivative or analog thereof that can inhibit PDCL3.

In some embodiments of the aspects described herein, the small molecule antagonist or agent that specifically targets or inhibits PDCL3 is Isoliquiritgenin ((E)-1-(2,4-dihydroxyphenyl)-3-(4-hydroxyphenyl)prop-2-en-1-one) or a derivative or analog thereof that can inhibit PDCL3.

In some embodiments of the aspects described herein, the small molecule antagonist or agent that specifically targets or inhibits PDCL3 is a protein tyrosine kinase inhibitor. In some such embodiments, the protein tyrosine kinase inhibitor is selected from DAPH, Emodin, Sunitinib malate, GW2974, Tyrphostin AG 112, Tyrphostin 23, Tyrphostin 51, and I-Ome-Tyrophostin AG 538.

In some embodiments of the aspects described herein, the small molecule antagonist or agent that specifically targets or inhibits PDCL3 is a protein tyrosine kinase inhibitor specific for or having specificity for EGFR. Protein tyrosine kinase inhibitor specific for or having specificity for EGFR for use in some embodiments of the aspects described herein include, but are not limited to, GW2974, Tyrphostin 23, Tyrphostin 51, Gefitinib, erlotinib, brigatinib, lapatinib, afatinib, CL-387785 (EKI-785), Canertinib (CI-1033), AZD9291, PD168393, Neratinib (HKI-272), AG-490 (Tyrphostin B42), CP-724714, Dacomitinib (PF299804, PF299), WZ4002, AZD8931 (Sapitinib), CUDC-101, AG-1478 (Tyrphostin AG-1478), PD153035 HCl, Pelitinib (EKB-569), AEE788 (NVP-AEE788), AC480 (BMS-599626), OSI-420, WZ3146, AST-1306, Rociletinib (CO-1686, AVL-301), Varlitinib, Icotinib, TAK-285, WHI-P154, PD168393, CNX-2006, Tyrphostin 9, AG-18, Poziotinib (HM781-36B), and AZ5104. In some such embodiments, the protein tyrosine kinase inhibitor specific for EGFR is selected from DAPH, GW2974, Tyrphostin 23, and Tyrphostin 51.

In some embodiments of the aspects described herein, the small molecule antagonist or agent that specifically targets or inhibits PDCL3 is an inhibitor of vesicular catecholine and/or serotonin uptake. In some such embodiments, the inhibitor of vesicular catecholine and/or serotonin uptake is Reserpine.

In some embodiments of the aspects described herein, the small molecule antagonist or agent that specifically targets or inhibits PDCL3 is a subtype selective retinoic acid receptor inhibitor. In some such embodiments, the subtype selective retinoic acid receptor inhibitor is AC-93253 iodide.

In some embodiments of the aspects described herein, the small molecule antagonist or agent that specifically targets or inhibits PDCL3 is a soluble guanylyl cyclase activator and/or aldose reductase inhibitor. In some such embodiments, the soluble guanylyl cyclase activator and/or aldose reductase inhibitor is Urapidil Hydrochloride.

In some embodiments of the aspects described herein, the small molecule antagonist or agent that specifically targets or inhibits PDCL3 is a nicotinic acetylcholine receptor antagonist. In some such embodiments, the nicotinic acetylcholine receptor antagonist is Mecamylamine hydrochloride.

In some embodiments of the aspects described herein, the small molecule antagonist or agent that specifically targets or inhibits PDCL3 is a SIRT2 inhibitor. In some such embodiments, the SIRT2 inhibitor is AGK2.

In some embodiments of the aspects described herein, the small molecule antagonist or agent that specifically targets or inhibits PDCL3 is an alpha1 Adrenoceptor antagonist. In some such embodiments, the alpha1 Adrenoceptor antagonist is Isoliquiritgenin.

In some embodiments of the aspects described herein, the small molecule antagonist or agent that specifically targets PDCL3 As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments, a small molecule antagonist of PDCL3 selectively binds to PDCL3. As used herein, "selectively binds" or "specifically binds" refers to the ability of a PDCL3 antagonist described herein to bind to the PDCL3 polypeptide, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if an antagonist described herein binds to the PDCL3 polypeptide with a $K_D$ of $10^{-5}$ M or lower, but not to other molecules, or a related homologue, then the agent is said to specifically bind the PDCL3 polypeptide. Specific binding can be influenced by, for example, the affinity and avidity of the antagonist and the concentration of the antagonist used. A person of ordinary skill in the art can determine appropriate conditions under which the antagonists described herein selectively bind using any suitable methods, such as titration of a PDCL3 antagonist in a suitable cell binding assay, such as those described herein in the Examples.

Pharmaceutical PDCL3 Antagonist Compositions and Therapeutic Methods Thereof

Certain aspects described herein are based, in part, on the discovery by the inventors that PDCL3 regulates VEGFR-2 stability, and therefore plays a critical role in regulating angiogenesis during embryonic development, as well as in pathological conditions mediated by aberrant angiogenesis. The inventors further discovered that inhibition of PDCL3 using PDCL3-specific antagonist agents, such as PDCL3 antagonist polypeptides or PDCL3 RNA interference agents, can inhibit VEGFR-2 mediated endothelial cell proliferation, and a variety of parameters that characterize angiogenesis, including capillary tube formation.

Accordingly, the PDCL3-specific antagonist agents, such as PDCL3 antagonist polypeptides or PDCL3 RNA interference agents, described herein can be used in methods of antiangiogenic therapy, such as novel cancer treatment strategies aimed at inhibiting existing tumor blood vessels and development of tumor blood vessels required for providing nutrients to support tumor growth. Because angiogenesis is involved in both primary tumor growth and metastasis, the antiangiogenic treatments using the PDCL3-specific antagonist agents, such as PDCL3 antagonist polypeptides or PDCL3 RNA interference agents, described herein are capable, for example, of inhibiting the neoplastic growth of tumor at the primary site, as well as preventing micro- and macrometastasis of tumors at the secondary sites, therefore allowing attack of the tumors by other therapeutics. Additionally, the PDCL3-specific antagonist agents, such as PDCL3 antagonist polypeptides or PDCL3 RNA interference agents, described herein can be used in methods of anti-metastasis therapy, such as novel cancer treatment strategies aimed at inhibiting tumor cell invasiveness for treatment and/or inhibition of micrometastasis and macrometastasis.

Angiogenesis is a process of tissue vascularization that involves both the growth of new developing blood vessels into a tissue (neo-vascularization) and co-opting of existing blood vessels to a target site. Blood vessels are the means by which oxygen and nutrients are supplied to living tissues and waste products are removed from living tissue. Angiogenesis can be a critical biological process. For example, angiogenesis is essential in reproduction, development and wound repair. Conversely, inappropriate angiogenesis can have severe negative consequences. For example, it is only after solid tumors are vascularized as a result of angiogenesis that the tumors have a sufficient supply of oxygen and nutrients that permit it to grow rapidly and metastasize.

Accordingly, angiogenesis-dependent diseases and disorders that can be treated using the methods and compositions comprising PDCL3-specific antagonist agents, such as PDCL3 antagonist polypeptides or PDCL3 RNA interference agents, described herein, are those diseases and disorders affected by vascular growth. In other words, an "angiogenesis-dependent disease or disorder" refers to those diseases or disorders that are dependent on a rich blood supply and blood vessel proliferation for the diseases' pathological progression (e.g., metastatic tumors), or diseases or disorders that are the direct result of aberrant blood vessel proliferation (e.g., diabetic retinopathy and hemangiomas). Non-limiting examples include abnormal vascular proliferation, ascites formation, psoriasis, age-related macular degeneration, thyroid hyperplasia, preeclampsia, rheumatoid arthritis and osteoarthritis, carotid artery disease, vaso vasorum neovascularization, vulnerable plaque neovascularization, neurodegenerative disorders, Alzheimer's disease, obesity, pleural effusion, atherosclerosis, endometriosis, diabetic/other retinopathies, ocular neovascularizations such as neovascular glaucoma and corneal neovascularization, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma, cancers which require neovascularization to support tumor growth, etc.

Accordingly, provided herein, in some aspects, are methods of inhibiting angiogenesis in a tissue of a subject or individual having a disease or disorder dependent or modulated by angiogenesis, where the disease or disorder can be treated by the inhibition of angiogenesis. Generally, the methods comprise administering to the subject having a disease or disorder dependent or modulated by angiogenesis a therapeutically effective amount of a composition comprising an angiogenesis-inhibiting amount of a PDCL3-specific antagonist agent, such as a PDCL3 antagonist polypeptide or PDCL3 RNA interference agent.

In some embodiments of these methods and all such methods described herein, the disease or disorder dependent or modulated by angiogenesis is cancer, where the rapidly dividing neoplastic cancer cells require an efficient blood supply to sustain their continual growth of the tumor. Inhibition of angiogenesis or tumor cell invasiveness or a combination thereof using the compositions and therapeutic methods described herein at the primary tumor site and secondary tumor site serve to prevent and limit metastasis and progression of disease.

In some aspects, provided herein are methods to treat a subject having a cancer or tumor comprising administering an effective amount of a PDCL3-specific antagonist agent, such as a PDCL3 antagonist polypeptide or PDCL3 RNA interference agent or a small molecule antagonist or agent that specifically targets or inhibits PDCL3.

In some embodiments of these methods and all such methods described herein, the PDCL3 antagonist agent is a PDCL3 antagonist polypeptide that reduces or inhibits VEGFR-2 mediated activity. In some such embodiments, the PDCL3 antagonist polypeptide specifically binds to VEGFR-2 and prevents binding of VEGFR-2 to endogenous PDCL3. In some embodiments of these methods and all such methods described herein, the PDCL3 antagonist polypeptide comprises a PDCL3 coil-coil domain. In some embodiments of these methods and all such methods described herein, the PDCL3 antagonist polypeptide comprises a PDCL3 thioredoxin domain. In some embodiments of these methods and all such methods described herein, the PDCL3 antagonist polypeptide comprises a PDCL3 C-terminal domain. In some embodiments of these methods and all such methods described herein, the PDCL3 antagonist polypeptide comprises a PDCL3 coil-coil domain and a PDCL3 thioredoxin domain. In some embodiments of these methods and all such methods described herein, the PDCL3 antagonist polypeptide comprises a PDCL3 thioredoxin domain and a PDCL3 C-terminal domain.

In some embodiments of these methods and all such methods described herein, the PDCL3 antagonist polypeptide comprises a coiled-coiled domain having the amino acid sequence of: MQDPNADTEWNDILRKKGIL-PPKESLKELEEEAEEEQRILQQSVVKTYED (SEQ ID NO: 9), or a portion, fragment, or derivative thereof, that inhibits VEGFR-2 activity and/or inhibits angiogenesis. In some such embodiments, the PDCL3 antagonist polypeptide portion, fragment, or derivative thereof results in about at least a 10% or more, at least a 15% or more, at least 20% or more, at least a 25% or more, at least a 30% or more, at least a 35% or more, at least a 40% or more, at least a 45% or more, at least a 50% or more, at least a 55% or more, at least a 60% or more, at least a 65% or more, at least a 70% or more, at least a 75% or more, at least a 80% or more, at least a 85% or more, at least a 90% or more, at least a 95% or more, or at least 100% or complete inhibition of VEGFR-2 activity in comparison to a reference or control level in the absence of the PDCL3 antagonist polypeptide portion, fragment, or derivative thereof.

In some embodiments of these methods and all such methods described herein, the PDCL3 antagonist agent is an RNA interference agent that specifically targets PDCL3 and reduces or inhibits VEGFR-2 mediated activity. In some such embodiments, the RNA interference agent is a double stranded RNA (dsRNA) targeting PDCL3. In some such embodiments, the RNA interference agent is an shRNA targeting PDCL3.

In some embodiments of these methods and all such methods described herein, the PDCL3 antagonist agent is an antagonist antibody or antibody fragment thereof that specifically binds to PDCL3 and reduces or inhibits PDCL3 mediated activity. In some such embodiments, the PDCL3-mediated activity is the VEGFR-2 stabilizing activity of PDCL3. In some such embodiments, PDCL3 is human PDCL3. In some such embodiments, PDCL3 has a sequence comprising SEQ ID NO: 1 or an allelic or splice variant thereof. In some such embodiments, the PDCL3 antagonist antibody binds PDCL3 and inhibits the ability of PDCL3 to, for example, bind VEGFR-2 and induce angiogenesis, to induce vascular endothelial cell proliferation or induce vascular permeability. In some such embodiments, the antagonist antibody or antibody fragment thereof that binds to PDCL3 and inhibits PDCL3 biological activity blocks interaction of PDCL3 with VEGFR-2. In some such embodiments, the VEGFR-2 has a sequence comprising the sequence of SEQ ID NO: 7. In some embodiments, the antagonist antibody or antibody fragment thereof is specific for an epitope of PDCL3 comprising a coil-coil domain portion of PDCL3, such as, for example, SEQ ID NO: 9. The ability of an antagonist antibody or antibody fragment that specifically binds to PDCL3 and reduces or inhibits PDCL3 mediated activity to inhibit angiogenesis can be assayed using methods described herein, such as, for example, measuring mean total tube number in an in vitro tubulogenesis assay, mean total tube length in an in vitro tubulogenesis assay, mean number of branching points in an in vitro tubulogenesis assay, mean number of vessel connections in an in vitro tubulogenesis assay, and tumor cell invasiveness.

In some embodiments of these methods and all such methods described herein, the PDCL3 antagonist antibody fragment is a Fab fragment. In some embodiments, the PDCL3 antagonist antibody fragment is a Fab' fragment. In some embodiments, the PDCL3 antagonist antibody fragment is a Fd fragment. In some embodiments, the PDCL3 antagonist antibody fragment is a Fd' fragment. In some embodiments, the PDCL3 antagonist is a Fv fragment. In some embodiments, the PDCL3 antagonist antibody fragment is a dAb fragment. In some embodiments, the PDCL3 antagonist antibody fragment comprises isolated CDR regions. In some embodiments, the PDCL3 antagonist antibody fragment is a F(ab')$_2$ fragment. In some embodiments, the PDCL3 antagonist antibody fragment is a single chain antibody molecule. In some embodiments, the PDCL3 antagonist antibody fragment is a diabody comprising two antigen binding sites. In some embodiments, the PDCL3 antagonist antibody fragment is a linear antibody comprising a pair of tandem Fd segments ($V_H$—$C_H1$-$V_H$—$C_H1$).

In some embodiments of these methods and all such methods described herein, the small molecule antagonist or agent that specifically targets or inhibits PDCL3 is selected from the group consisting of Reserpine, DAPH, AC-93253 iodide, Emodin, Sunitinib malate, GW2974, Urapidil Hydrochloride, Mecamylamine hydrochloride, (−)-MK-801 hydrogen maleate, AGK2, Tyrphostin AG 112, Tyrphostin 23, Tyrphostin 51, I-Ome-Tyrophostin AG 538, and Isoliquiritgenin.

Examples of additional PDCL3 antagonist agents for use in the therapeutic methods described herein include, but are not limited to, small molecule agents which block the binding of VEGFR-2 to PDCL3, small molecule agents that interfere with downstream signaling events of PDCL3, or other compounds or agents that inhibit activity and/or expression of PDCL3. Such compounds can bind to the VEGFR-2 binding site of PDCL3 and prevent binding of VEGFR-2, for example.

Where the growth of new blood vessels is the cause of, or contributes to, the pathology associated with a disease, inhibition of angiogenesis will reduce the deleterious effects of the disease. Non-limiting examples include tumors, carotid artery disease, rheumatoid arthritis, diabetic retinopathy, inflammatory diseases, restenosis, and the like. Where the growth of new blood vessels is required to support growth of a deleterious tissue, inhibition of angiogenesis will reduce the blood supply to the tissue and thereby contribute to reduction in tissue mass based on blood supply requirements. Non-limiting examples include growth of tumors where neovascularization is a continual requirement in order that the tumor growth beyond a few millimeters in thickness, and for the establishment of solid tumor metastases. Another example is coronary plaque enlargement.

There are a variety of diseases or disorders in which angiogenesis is believed to lead to negative consequences, referred to as pathological angiogenesis, or diseases or disorders dependent or modulated by angiogenesis, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

Accordingly, in some aspects and embodiments of the methods described herein, the methods are directed to inhibiting angiogenesis in a subject having or at risk for cancer.

The terms "cancer" and "cancerous" refer to or describe the physiological condition in mammals that is typically characterized by unregulated cell growth. Included in this definition are benign and malignant cancers, as well as dormant tumors or micrometastases. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In other aspects and embodiments, the methods described herein are used in blocking or inhibiting angiogenesis that occurs in age-related macular degeneration. It is known, for example, that VEGF contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula. Accordingly, encompassed in the methods disclosed herein are subjects treated for age-related macular degeneration with anti-angiogenic therapy.

In other aspects and embodiments, the methods described herein are used in blocking or inhibiting angiogenesis that occurs in a subject having diabetic retinopathy, where abnormal blood vessel growth is associated with diabetic eye diseases and diabetic macular edema. When normal blood vessels in the retina are damaged by tiny blood clots due to diabetes, a chain reaction is ignited that culminates in new blood vessel growth. However, the backup blood vessels are faulty; they leak (causing edema), bleed and encourage scar tissue that detaches the retina, resulting in severe loss of vision. Such growth is the hallmark of diabetic retinopathy, the leading cause of blindness among young people in developed countries. Therefore, encompassed in the methods disclosed herein are subjects treated for diabetic retinopathy and/or diabetic macular edema.

In some aspects and embodiments, the methods described herein are used in blocking or inhibiting angiogenesis that occurs in a subject having rheumatoid arthritis. Rheumatoid arthritis (RA) is characterized by synovial tissue swelling, leukocyte ingress and angiogenesis, or new blood vessel growth. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognized as a key event in the formation and maintenance of the pannus in RA (Paleolog, E. M., Arthritis Res. 2002; 4 Suppl 3:S81-90; Afuwape A O, Histol Histopathol. 2002; 17(3):961-72). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur (Koch, A. E., Ann. Rheum. Dis. 2000, 59 Suppl 1:i65-71). Disruption of the formation of new blood vessels would not only prevent delivery of nutrients to the inflammatory site, it could also reduce joint swelling due to the additional activity of VEGF, a potent proangiogenic factor in RA, as a vascular permeability factor. Anti-VEGF hexapeptide RRKRRR (dRK6; SEQ ID NO: 15) can suppress and mitigate the arthritis severity (Seung-Ah Yoo, et. al., 2005, supra). Accordingly, encompassed in the methods disclosed herein are subjects having or being treated for rheumatoid arthritis.

In some aspects and embodiments, the methods described herein are used in blocking or inhibiting angiogenesis that occurs in Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with an anti-angiogenic effects, seem to prevent Alzheimer's disease and/or influence the outcome of AD patients. Therefore, AD angiogenesis in the brain vasculature can play an important role in AD. In Alzheimer's disease, the brain endothelium secretes the precursor substrate for the beta-amyloid plaque and a neurotoxic peptide that selectively kills cortical neurons. Moreover, amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies can interfere with endothelial cell activation in AD (Schultheiss C., el. al., 2006; Grammas P., et. al., 1999) and can be used for preventing and/or treating AD. Accordingly, encompassed in the methods disclosed herein are subjects being treated for Alzheimer's disease.

In other aspects and embodiments, the methods described herein are used in blocking or inhibiting angiogenesis that occurs in obesity. Adipogenesis in obesity involves interplay between differentiating adipocytes, stromal cells, and blood vessels. Close spatial and temporal interrelationships between blood vessel formation and adipogenesis, and the sprouting of new blood vessels from preexisting vasculature was coupled to adipocyte differentiation. Adipogenic/angiogenic cell clusters can morphologically and immunohistochemically be distinguished from crown-like structures frequently seen in the late stages of adipose tissue obesity. It has been shown that administration of anti-vascular endothelial growth factor (VEGF) antibodies inhibited not only angiogenesis but also the formation of adipogenic/angiogenic cell clusters, indicating that the coupling of adipogenesis and angiogenesis is essential for differentiation of adipocytes in obesity and that VEGF is a key mediator of that process. (Satoshi Nishimura et. al., 2007, Diabetes 56:1517-1526). It has been shown that the angiogenesis inhibitor, TNP-470 was able to prevent diet-induced and genetic obesity in mice (Ebba Brakenhielm et. al., Circulation Research, 2004; 94:1579). TNP-470 reduced vascularity in the adipose tissue, thereby inhibiting the rate of growth of the adipose tissue and obesity development. Accordingly, encompassed in the methods disclosed herein are subjects suffering from obesity.

In some aspects and embodiments, the methods described herein are used in blocking or inhibiting angiogenesis that occurs in endometriosis. Excessive endometrial angiogenesis is proposed as an important mechanism in the pathogenesis of endometriosis (Healy, D L., et. al., Hum Reprod Update. 1998 September-October; 4(5):736-40). The endometrium of patients with endometriosis shows enhanced endothelial cell proliferation. Moreover there is an elevated expression of the cell adhesion molecule integrin vβ3 in more blood vessels in the endometrium of women with endometriosis when compared with normal women. The U.S. Pat. No. 6,121,230 described the use of anti-VEGF agents in the treatment of endometriosis and is Patent is incorporated hereby reference. Accordingly, encompassed in the methods disclosed herein are subjects having or being treated for endometriosis.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

The individual or subject to be treated in the various aspects and embodiments described herein is desirably a human patient, although it is to be understood that the methods are effective with respect to all mammals, which are intended to be included in the term "patient" or "subject". In this context, a mammal is understood to include any mammalian species in which treatment of diseases associated with angiogenesis is desirable. The terms "subject" and "individual" are used interchangeably herein, and refer to an animal, for example a human, recipient of the PDCL3-specific antagonist agents, such as a PDCL3 antagonist polypeptide or PDCL3 RNA interference agent described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

Combination Therapies

In other aspects, the methods provided for inhibiting angiogenesis in a tissue of a subject or individual having a disease or disorder dependent or modulated by angiogenesis by administering to the subject a therapeutically effective amount of a composition comprising an angiogenesis-inhibiting amount of a PDCL3-specific antagonist agent, such as a PDCL3 antagonist polypeptide or PDCL3 RNA interference agent, can further comprise one or more additional treatments such as angiogenic inhibitors, chemotherapy, radiation, surgery, or other treatments known to those of skill in the art to inhibit angiogenesis.

In some embodiments of these aspects and all such aspects described herein, the methods described herein further comprise administration of a combination of at least one PDCL3-specific antagonist agent, such as a PDCL3 antagonist polypeptide or PDCL3 RNA interference agent, with one or more additional anti-cancer therapies. Examples of additional anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the PDCL3 antagonist agents.

In some embodiments, the methods comprise administering effective amounts of a PDCL3-specific antagonist agent, such as a PDCL3 antagonist polypeptide or PDCL3 RNA interference agent, and one or more chemotherapeutic agents to a subject susceptible to, or diagnosed with, locally recurrent or previously untreated cancer. A variety of chemotherapeutic agents can be used in the combined treatment methods and uses of the invention. An exemplary and non-limiting list of chemotherapeutic agents contemplated for use in the methods described herein is provided under "Definition," or described herein.

In some embodiments, the methods described herein comprise administration of a PDCL3-specific antagonist agent, such as a PDCL3 antagonist polypeptide or PDCL3 RNA interference agent, with one or more chemotherapeutic agents (e.g., a cocktail) or any combination thereof. In certain embodiments, the chemotherapeutic agent is for example, capecitabine, taxane, anthracycline, paclitaxel, docetaxel, paclitaxel protein-bound particles (e.g., Abraxane™), doxorubicin, epirubicin, 5-fluorouracil, cyclophosphamide or combinations thereof therapy. As used herein, combined administration includes simultaneous administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents can be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). Accordingly, in some embodiments, the chemotherapeutic agent can precede, or follow administration of the PDCL3-specific antagonist agent, or can be given simultaneously therewith.

In some other embodiments of the methods described herein, other therapeutic agents useful for combination tumor therapy with the PDCL3-specific antagonist agents, such as PDCL3 antagonist polypeptides or PDCL3 RNA interference agents described herein, include antagonists of other factors that are known to be involved in tumor growth, such as EGFR, ErbB2 (also known as Her2), ErbB3, ErbB4, or TNF. In some embodiments, it can be beneficial to also administer one or more cytokines to the subject. In some embodiments, the PDCL3 antagonist agent is co-administered with a growth inhibitory agent. For example, the growth inhibitory agent can be administered first, followed by the PDCL3-specific antagonist agent. However, simultaneous administration or administration of the PDCL3 antagonist agent first is also contemplated. Suitable dosages for the growth inhibitory agent are those presently used and can be lowered due to the combined action (synergy) of the growth inhibitory agent and the PDCL3 antagonist agent.

Examples of additional angiogenic inhibitors that can be used in combination with the PDCL3-specific antagonist agents, such as a PDCL3 antagonist polypeptide or PDCL3 RNA interference agent, described herein include, but are not limited to: direct angiogenesis inhibitors, Angiostatin, Bevacizumab (Avastin®), Arresten, Canstatin, Combretastatin, Endostatin, NM-3, Thrombospondin, Tumstatin, 2-methoxyestradiol, cetuximab (Erbitux®), panitumumab (Vectibix™), trastuzumab (Herceptin®) and Vitaxin; and indirect angiogenesis inhibitors: ZD1839 (Iressa), ZD6474, OSI774 (Tarceva), CI1033, PKI1666, IMC225 (Erbitux), PTK787, SU6668, SU11248, Herceptin, and IFN-α, CELEBREX® (Celecoxib), THALOMID® (Thalidomide), and IFN-α.

In some embodiments, the additional angiogenesis inhibitors for use in the methods described herein include but are not limited to small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®).

In some embodiments, the angiogenesis inhibitors for use in the methods described herein include but are not limited to inhibitors of mTOR (mammalian target of rapamycin) such as temsirolimus (TORICEL™), bortezomib (VELCADE®), thalidomide (THALOMID®), and Doxycyclin.

In other embodiments, the angiogenesis inhibitors for use in the methods described herein include one or more drugs that also target the VEGF pathway. Bevacizumab (AVASTIN®) was the first drug that targeted new blood vessels to be approved for use against cancer. It is a monoclonal antibody that binds to VEGF, thereby blocking VEGF from reaching the VEGF receptor (VEGFR). Other drugs, such as sunitinib (SUTENT®) and sorafenib (NEXAVAR®), are small molecules that attach to the VEGF receptor itself, preventing it from being turned on. Such drugs are collectively termed VEGF inhibitors. As the VEGF/VPF protein interacts with the VEGFRs, inhibition of either the ligand VEGF, e.g. by reducing the amount that is available to interact with the receptor; or inhibition of the receptor's intrinsic tyrosine kinase activity, blocks the function of this pathway. This pathway controls endothelial cell growth, as well as permeability, and these functions are mediated through the VEGFRs.

Accordingly, as described herein, "VEGF inhibitors" for use as angiogenesis inhibitors include any compound or agent that produces a direct or indirect effect on the signaling pathways that promote growth, proliferation and survival of a cell by inhibiting the function of the VEGF protein, including inhibiting the function of VEGF receptor proteins, with the exception of the PDCL3 antagonist agents described herein. These include any organic or inorganic molecule, including, but not limited to modified and unmodified nucleic acids such as antisense nucleic acids, RNAi agents such as siRNA or shRNA, peptides, peptidomimetics, receptors, ligands, and antibodies that inhibit the VEGF signaling pathway. The siRNAs are targeted at components of the VEGF pathways and can inhibit the VEGF pathway. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Eterna Zentaris Inc; Quebec City, Calif.), ZM323881 (CalBiochem. Calif., USA), pegaptanib (Macugen) (Eyetech Pharmaceuticals), an anti-VEGF aptamer and combinations thereof.

VEGF inhibitors are also disclosed in U.S. Pat. Nos. 6,534,524 and 6,235,764, the contents of both of which are herein incorporated in their entirety. Additional VEGF inhibitors are described in, for example in WO 99/24440 (published May 20, 1999), International Application PCT/IB99/00797 (filed May 3, 1999), in WO 95/21613 (published Aug. 17, 1995), WO 99/61422 (published Dec. 2, 1999), U.S. Pat. Publ. No. 20060094032 "siRNA agents targeting VEGF", U.S. Pat. No. 6,534,524 (discloses AG13736), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), WO 01/02369 (published Jan. 11, 2001); U.S. Provisional Application No. 60/491,771 piled Jul. 31, 2003); U.S. Provisional Application No. 60/460,695 (filed Apr. 3, 2003); and WO 03/106462A1 (published Dec. 24, 2003). Other examples of VEGF inhibitors are disclosed in International Patent Publications WO 99/62890 published Dec. 9, 1999, WO 01/95353 published Dec. 13, 2001 and WO 02/44158 published Jun. 6, 2002.

In other embodiments, the angiogenesis inhibitors for use in the methods described herein include anti-angiogenic factors such as alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C-X-C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-b), vasculostatin, and vasostatin (calreticulin fragment).pamidronate thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et. al., British Journal of Cancer (2004) 90, 245-252), anti-VEGF peptide RRKRRR (dRK6) (SEQ ID NO: 15) (Seung-Ah Yoo, J. Immuno, 2005, 174: 5846-5855).

Thus, in connection with the administration of a PDCL3-specific antagonist agent, such as a PDCL3 antagonist polypeptide or PDCL3 RNA interference agent, a compound which inhibits angiogenesis indicates that administration in a clinically appropriate manner results in a beneficial effect for at least a statistically significant fraction of patients, such as improvement of symptoms, a cure, a reduction in disease load, reduction in tumor mass or cell numbers, extension of life, improvement in quality of life, or other effect generally recognized as positive by medical doctors familiar with treating the particular type of disease or condition.

The compositions described herein can also contain more than one active compound as necessary for the particular indication being treated, and these active compounds are preferably those with complementary activities that do not adversely affect each other. For example, it can be desirable to further provide antibodies or antagonists that bind to EGFR, VEGF, VEGFR, or ErbB2 (e.g., Herceptin™). Alternatively, or in addition, the composition can comprise a cytotoxic agent, cytokine, growth inhibitory agent and/or VEGFR antagonist. Such molecules are suitably present in combination in amounts that are effective for the purpose intended.

In certain aspects of any of the methods and uses described herein, other therapeutic agents useful for combination cancer therapy with the PDCL3-specific antagonist agent, such as a PDCL3 antagonist polypeptide or PDCL3 RNA interference agent, described herein include other anti-angiogenic agents. Many anti-angiogenic agents have been identified and are known in the arts, including those listed by Carmeliet and Jain (2000). In some embodiments, the PDCL3-specific antagonist agent, such as a PDCL3 antagonist polypeptide or PDCL3 RNA interference agent, described herein is used in combination with a VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more PDCL3 antagonist agents can be co-administered to the subject.

For the treatment of diseases, as described herein, the appropriate dosage of PDCL3 specific antagonist agents will depend on the type of disease to be treated, as defined above, the severity and course of the disease, whether the PDCL3 antagonist agent is administered for preventive or therapeutic purposes, previous therapeutic indications, the subject's clinical history and response to the PDCL3 antagonist agent, and the discretion of the attending physician. The PDCL3 antagonist agent is suitably administered to the subject at one time or over a series of treatments. In a combination therapy regimen, the PDCL3 antagonist agent and the one or more anti-cancer therapeutic agents described herein are administered in a therapeutically effective or synergistic amount. As used herein, a therapeutically effective amount is such that co-administration of a PDCL3 antagonist agent and one or more other therapeutic agents, or administration of a composition described herein, results in reduction or inhibition of the cancer as described herein. A therapeutically synergistic amount is that amount of a PDCL3 antagonist agent and one or more other therapeutic agents necessary to synergistically or significantly reduce or eliminate conditions or symptoms associated with a particular disease, such as cancer.

The PDCL3 antagonist agent and the one or more other therapeutic agents can be administered simultaneously or sequentially in an amount and for a time sufficient to reduce or eliminate the occurrence or recurrence of a tumor, a dormant tumor, or a micrometastases. The PDCL3 antagonist agent and the one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject can be subjected to radiation therapy, in some embodiments of the methods described herein.

Modes of Administration

The PDCL3-specific antagonist agents, such as PDCL3 antagonist polypeptides or PDCL3 RNA interference agents, described herein can be administered to a subject in need thereof by any appropriate route which results in an effective treatment in the subject. As used herein, the terms "administering," and "introducing" are used interchangeably and refer to the placement of a PDCL3-specific antagonist agent, such as a PDCL3 antagonist polypeptide or PDCL3 RNA interference agent, into a subject by a method or route which results in at least partial localization of such agents at a desired site, such as a site of inflammation or a site of angiogenesis, such that a desired effect(s) is produced.

In some embodiments, the PDCL3-specific antagonist agent, such as a PDCL3 antagonist polypeptide or PDCL3 RNA interference agent, is administered to a subject having an angiogenic disorder to be inhibited by any mode of administration that delivers the agent systemically or to a desired surface or target, and can include, but is not limited to, injection, infusion, instillation, and inhalation administration. To the extent that PDCL3-specific antagonist agents, such as PDCL3 antagonist polypeptides or PDCL3 RNA interference agents, can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the PDCL3-specific antagonist agents, such as PDCL3 antagonist polypeptides or PDCL3 RNA interference agents, for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the PDCL3-specific antagonist agent other than directly into a target site, tissue, or organ, such as a tumor site, such that it enters the subject's circulatory system and, thus, is subject to metabolism and other like processes.

The term "intravenous infusion" refers to introduction of a PDCL3-specific antagonist agent into the vein of an animal or human subject over a period of time greater than approximately 5 minutes, in some embodiments between approximately 30 to 90 minutes, and in some embodiments, intravenous infusion is administered for 10 hours or less. The term "intravenous bolus" or "intravenous push" refers to administration into a vein of an animal or human such that the body receives the drug, such as a PDCL3-specific antagonist agent, in approximately 15 minutes or less, preferably 5 minutes or less.

The term "subcutaneous administration" refers to introduction of a a PDCL3-specific antagonist agent under the skin of an animal or human subject, preferable within a pocket between the skin and underlying tissue, by relatively slow, sustained delivery from a drug receptacle. The pocket can be created by pinching or drawing the skin up and away from underlying tissue.

The term "subcutaneous infusion" refers to introduction of an agent, such as a PDCL3-specific antagonist agent, under the skin of an animal or human subject, preferably within a pocket between the skin and underlying tissue, by relatively slow, sustained delivery from a drug receptacle for a period of time including, but not limited to, 30 minutes or less, or 90 minutes or less. Optionally, the infusion can be made by subcutaneous implantation of a drug delivery pump implanted under the skin of the animal or human subject, wherein the pump delivers a predetermined amount of agent for a predetermined period of time, such as 30 minutes, 90 minutes, or a time period spanning the length of the treatment regimen.

Pharmaceutical Formulations

For the clinical use of the methods described herein, administration of the PDCL3-specific antagonist agents, such as PDCL3 antagonist polypeptides or PDCL3 RNA interference agents, can include formulation into pharmaceutical compositions or pharmaceutical formulations for parenteral administration, e.g., intravenous; mucosal, e.g., intranasal; ocular, or other mode of administration. In some embodiments, the PDCL3-specific antagonist agents described herein can be administered along with any pharmaceutically acceptable carrier compound, material, or composition which results in an effective treatment in the subject. Thus, a pharmaceutical formulation for use in the methods described herein can contain a PDCL3-specific antagonist agent, such as a PDCL3 antagonist polypeptide or PDCL3 RNA interference agent, as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an PDCL3 antagonist antibody or antibody fragment thereof. Each carrier must be "acceptable" in the sense of being compatible with the other ingredients of the formulation and not injurious to the patient. The terms "excipient", "carrier", "pharmaceutically acceptable carrier" or the like are used interchangeably herein.

The PDCL3-specific antagonist agents, such as PDCL3 antagonist polypeptides or PDCL3 RNA interference agents, described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a PDCL3-specific antagonist agent, such as a PDCL3 antagonist polypeptide or PDCL3 RNA interference agent, can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Therapeutic formulations of the PDCL3-specific antagonist agents, such as PDCL3 antagonist polypeptides or PDCL3 RNA interference agenta, described herein can be prepared for storage by mixing a PDCL3 antagonist agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary lyophilized anti-VEGF antibody formulations are described in WO 97/04801, expressly incorporated herein be reference.

Optionally, but preferably, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The therapeutic formulations of the compositions comprising PDCL3 antagonist agents described herein can also contain more than one active compound as necessary for the particular indication being treated, preferably those with complementary activities that do not adversely affect each other. For example, in some embodiments, it can be desirable to further provide antibodies which bind to EGFR, VEGF (e.g. an antibody which binds a different epitope on VEGF), VEGFR, or ErbB2 (e.g., HERCEPTIN™). Alternatively, or in addition, the composition can comprise a cytotoxic agent, cytokine, growth inhibitory agent and/or VEGFR antagonist. Such molecules are suitably present in combination in amounts that are effective for the purpose intended.

The active ingredients of the therapeutic formulations of the compositions comprising PDCL3 antagonist agents described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release preparations can be used. Suitable examples of sustained-release preparations include semipermeable matrices of solid hydrophobic polymers containing the PDCL3-specific antagonist agent, such as a PDCL3 antagonist polypeptide or PDCL3 RNA interference agent, in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The therapeutic formulations to be used for in vivo administration, such as parenteral administration, in the methods described herein can be sterile, which is readily accomplished by filtration through sterile filtration membranes, or other methods known to those of skill in the art.

Dosages and Duration

The PDCL3-specific antagonist agents described herein, such as PDCL3 antagonist polypeptides or PDCL3 RNA interference agents, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" of the PDCL3 antagonist agent to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The PDCL3-specific antagonist agent, such as a PDCL3 antagonist polypeptide or PDCL3 RNA interference agent, is optionally formulated with one or more additional therapeutic agents currently used to prevent or treat cancer or a risk of developing a cancer. The effective amount of such other agents depends on the amount of PDCL3 antagonist agent present in the formulation, the type of disorder or treatment, and other factors discussed above. These are generally used in the same dosages and with administration routes as used herein before or about from 1 to 99% of the heretofore employed dosages.

Depending on the type and severity of the disease, about 1 g/kg to 100 mg/kg (e.g., 0.1-20 mg/kg) of a PDCL3-specific antagonist agent, such as a PDCL3 antagonist polypeptide or PDCL3 RNA interference agent, is an initial candidate dosage for administration to a subject, whether, for example, by one or more separate administrations, or by continuous infusion. A typical daily dosage might range from about 1 µg/kg to about 100 mg/kg or more, depending on the factors mentioned above. Particularly desirable dosages include, for example, 5 mg/kg, 7.5 mg/kg, 10 mg/kg, and 15 mg/kg. For repeated administrations over several days or longer, depending on the condition, the treatment is sustained until, for example, the cancer is treated, as measured by the methods described above or known in the art. However, other dosage regimens can be useful. In one non-limiting example, if the PDCL3-specific antagonist agent is a PDCL3 antagonist polypeptide, the PDCL3 antagonist polypeptide is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. The progress of using the methods described herein can be easily monitored by conventional techniques and assays.

The duration of a therapy using the methods described herein will continue for as long as medically indicated or until a desired therapeutic effect (e.g., those described herein) is achieved. In certain embodiments, the PDCL3 antagonist agent therapy, such as a PDCL3 antagonist polypeptide or PDCL3 specific RNA interference agent, described herein is continued for 1 month, 2 months, 4 months, 6 months, 8 months, 10 months, 1 year, 2 years, 3 years, 4 years, 5 years, 10 years, 20 years, or for a period of years up to the lifetime of the subject.

The PDCL3-specific antagonists described herein are administered to a subject, e.g., a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration, for example, to a tumor or cancer site where angiogenesis is occurring, is particularly desired if extensive side effects or toxicity is associated with the use of the PDCL3 antagonist agent. An ex vivo strategy can also be used for therapeutic applications in some embodiments. Ex vivo strategies involve transfecting or transducing cells obtained from a subject with a polynucleotide encoding a PDCL3 antagonist. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

In some embodiments, the PDCL3 antagonist agent is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In some embodiments, the antibody or antibody fragment thereof is suitably administered by pulse infusion, particularly with declining doses of the antibody. Preferably the dosing is given by injections, most preferably intravenous or subcutaneous injections, depending in part on whether the administration is brief or chronic.

In some embodiments, the PDCL3 antagonist agent is administered locally, e.g., by direct injections, when the disorder or location of the tumor permits, and the injections can be repeated periodically. The PDCL3 antagonist agent can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Efficacy of the Treatment

The efficacy of the treatment methods for cancer comprising therapeutic formulations of the compositions comprising the PDCL3 antagonist agents described herein can be measured by various endpoints commonly used in evaluating cancer treatments, including but not limited to, tumor regression, tumor weight or size shrinkage, time to progression, duration of survival, progression free survival, overall response rate, duration of response, and quality of life. Because the PDCL3 antagonist agents, e.g., PDCL3 antagonist polypeptides or PDCL3-specific RNA interference agents, described herein target the tumor vasculature and some cancer stem cells, they represent a unique class of anticancer drugs, and therefore can require unique measures and definitions of clinical responses to drugs. For example, tumor shrinkage of greater than 50% in a 2-dimensional analysis is the standard cut-off for declaring a response. However, the PDCL3 antagonist agents described herein can cause inhibition of metastatic spread without shrinkage of the primary tumor, or can simply exert a tumoristic effect. Accordingly, novel approaches to determining efficacy of an anti-angiogenic therapy should be employed, including for example, measurement of plasma or urinary markers of angiogenesis, and measurement of response through molecular imaging. In the case of cancers, the therapeutically effective amount of the PDCL3 antagonist agent can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent that the PDCL3 antagonist agent can prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

In other embodiments, described herein are methods for increasing progression free survival of a human subject susceptible to or diagnosed with a cancer. Time to disease progression is defined as the time from administration of the drug until disease progression or death. In a preferred embodiment, the combination treatment of the invention using a PDCL3 antagonist agent, such as a PDCL3 antagonist polypeptide or PDCL3-specific RNA interference agent, and one or more chemotherapeutic agents significantly increases progression free survival by at least about 1 month, 1.2 months, 2 months, 2.4 months, 2.9 months, 3.5 months, preferably by about 1 to about 5 months, when compared to a treatment with chemotherapy alone. In another embodiment, the methods described herein significantly increase response rates in a group of human subjects susceptible to or diagnosed with a cancer who are treated with various therapeutics. Response rate is defined as the percentage of treated subjects who responded to the treatment. In one embodiment, the combination treatment described herein using a PDCL3 antagonist agent, such as a PDCL3 antagonist polypeptide or PDCL3-specific RNA interference agent, and one or more chemotherapeutic agents significantly increases response rate in the treated subject group compared to the group treated with chemotherapy alone.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the PDCL3 antagonist agents, such as PDCL3 antagonist polypeptides or PDCL3-specific RNA interference agents, thereof described herein to a subject in order to alleviate a symptom of a cancer, or other such disorder characterized by excess or unwanted angiogenesis. As used herein, "alleviating a symptom of a cancer" is ameliorating or reducing any condition or symptom associated with the cancer. As compared with an equivalent untreated control, such reduction or degree of prevention is at least 5%, at least 10%, at least 20%, at least 40%, at least 50%, at least 60%, at least 80%, at least 90%, at least 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer.

The term "effective amount" as used herein refers to the amount of a PDCL3 antagonist agent, needed to alleviate at least one or more symptom of the disease or disorder, and relates to a sufficient amount of pharmacological composition to provide the desired effect, i.e., inhibit the formation of new blood vessels. The term "therapeutically effective amount" therefore refers to an amount of a PDCL3 antagonist agent, such as a PDCL3 antagonist polypeptide or PDCL3-specific RNA interference agent, using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the PDCL3 antagonist agent), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Engineered PDCL3 and Protein Production

As demonstrated herein, preventing N-terminal acetylation of PDCL3 potently increases PDCL3 chaperone protein activity. It is demonstrated herein that PDCL3 is present at both the endoplasmic reticulum (ER) and cytoplasmic compartments. Consistent with the chaperone function of PDCL3, ER-localized PDCL3 associates with newly synthesized VEGFR-2 where it protects VEGFR-2 from degradation. The data described herein demonstrate that N-terminal methionine acetylation regulates stability of PDCL3. PDCL3 stability plays an important role in angiogenesis, as its expression was upregulated by hypoxia, a master regulator of angiogenesis. Furthermore, zebrafish experiments confirmed its biological importance to angiogenesis. Over-expression of an engineered PDCL3 unable to undergo N-terminal acetylation was significantly more potent than the wild type PDCL3 in its ability to stimulate angiogenesis in endothelial cells.

Figure 5A:
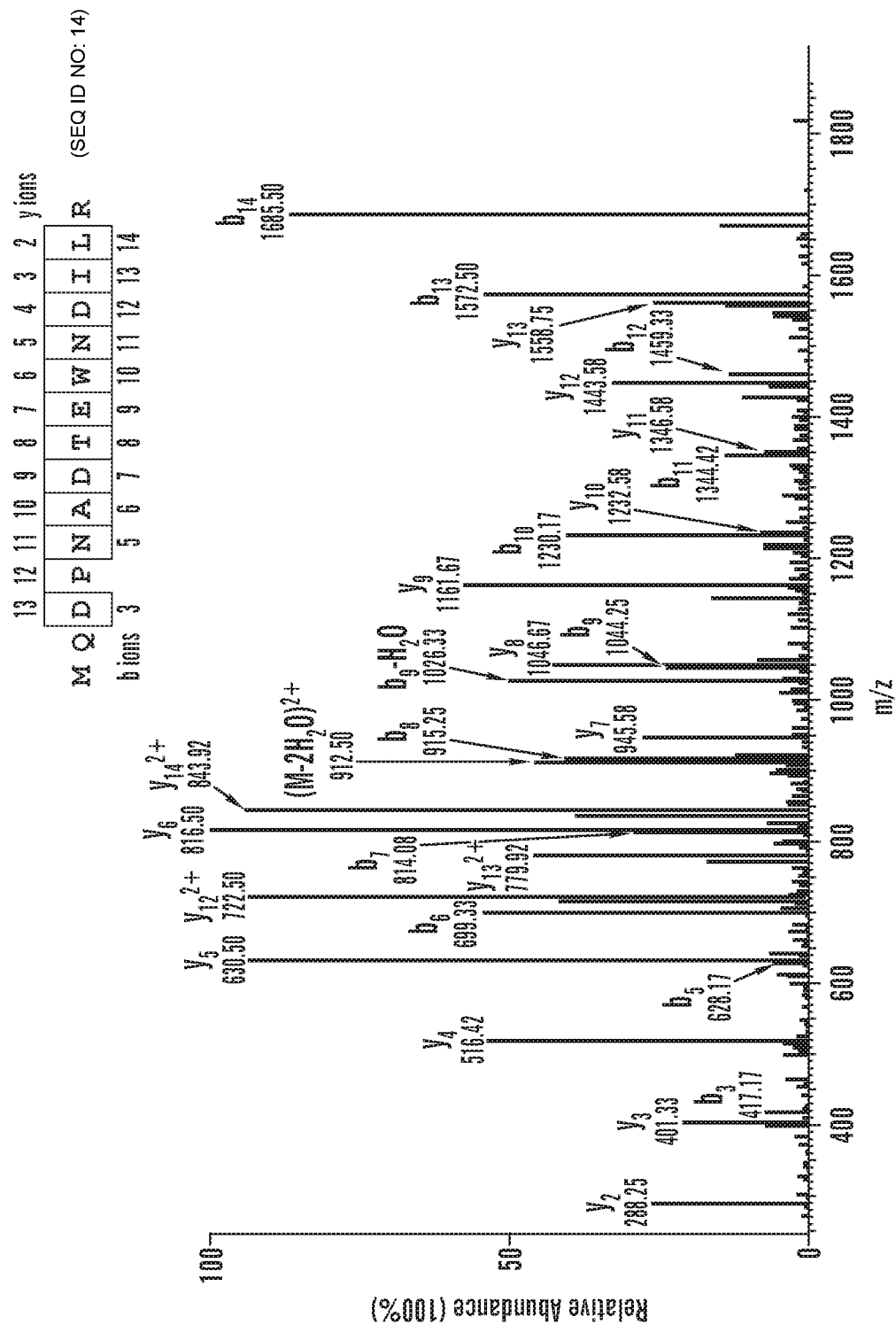

More specifically, to further examine hypoxia-mediated expression of PDCL3, posttranslational modification on PDCL3 by liquid chromatography-tandem mass spectrometry (LC-MS/MS) analysis was performed and analyzed. This analysis revealed that PDCL3 was acetylated on the N-terminal methionine (FIG. 5A). Acetylation of N-terminal methionine is thought to regulate protein stability by serving as a degradation signal designated "N-degron"[42].

To examine the possible role of N-terminal methionine acetylation in expression of PDCL3, an acetylation resistant PDCL3 construct was generated by inserting an HA-tag at the N-terminal of PDCL3 (FIG. 5B). Despite using an equal amount of DNA constructs, expression of HA-tagged PDCL3 was higher compared to expression of wild-type PDCL3 (FIG. 5B). A cycloheximide (CHX)-chase assay was performed in which half-life of PDCL3 after inhibition of its translation by CHX was analyzed. The half-life of wild-type PDCL3 was relatively short (about 30 minutes) whereas acetylation resistant HA-tagged PDCL3 was quite stable up to 60 minutes (FIG. 5C), indicating that N-terminal methionine acetylation promotes degradation of PDCL3 and preventing its acetylation makes it more stable protein.

Figure 6A:
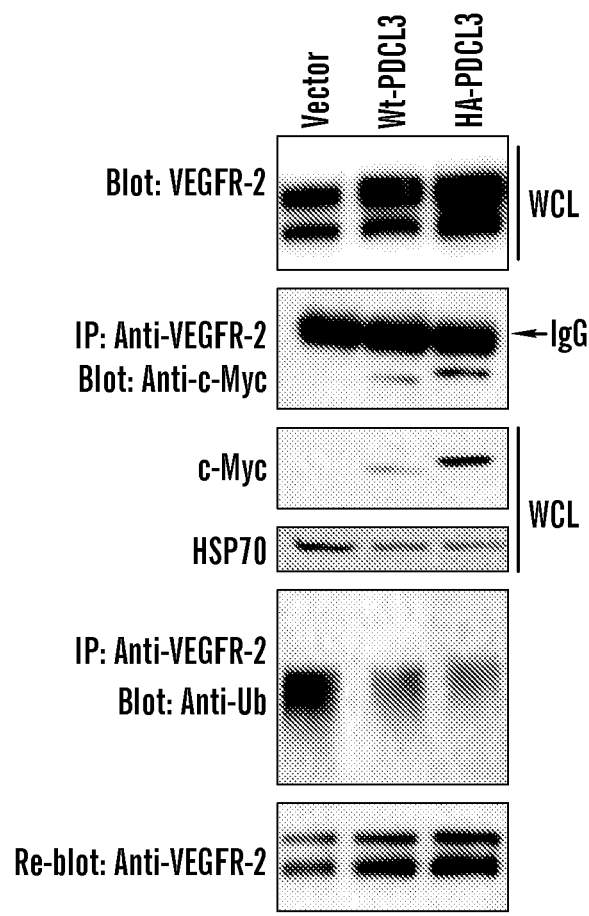
FIGS. 6A-6C demonstrate that HA-tagged N-terminus methionine mutant PDCL3 binds VEGFR-2 and increases VEGFR-2 dependent capillary tube formation.
Figure 6B:
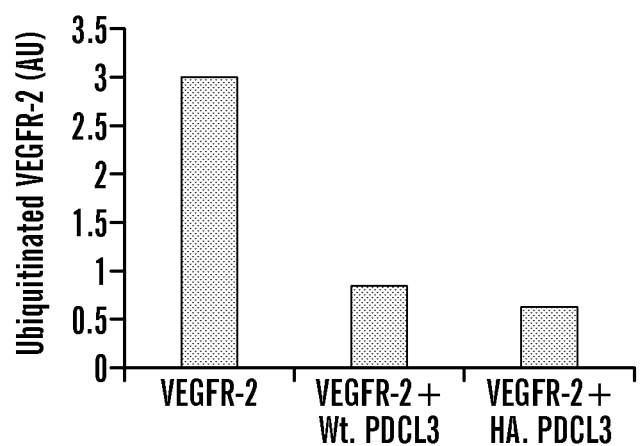
Figure 6C:
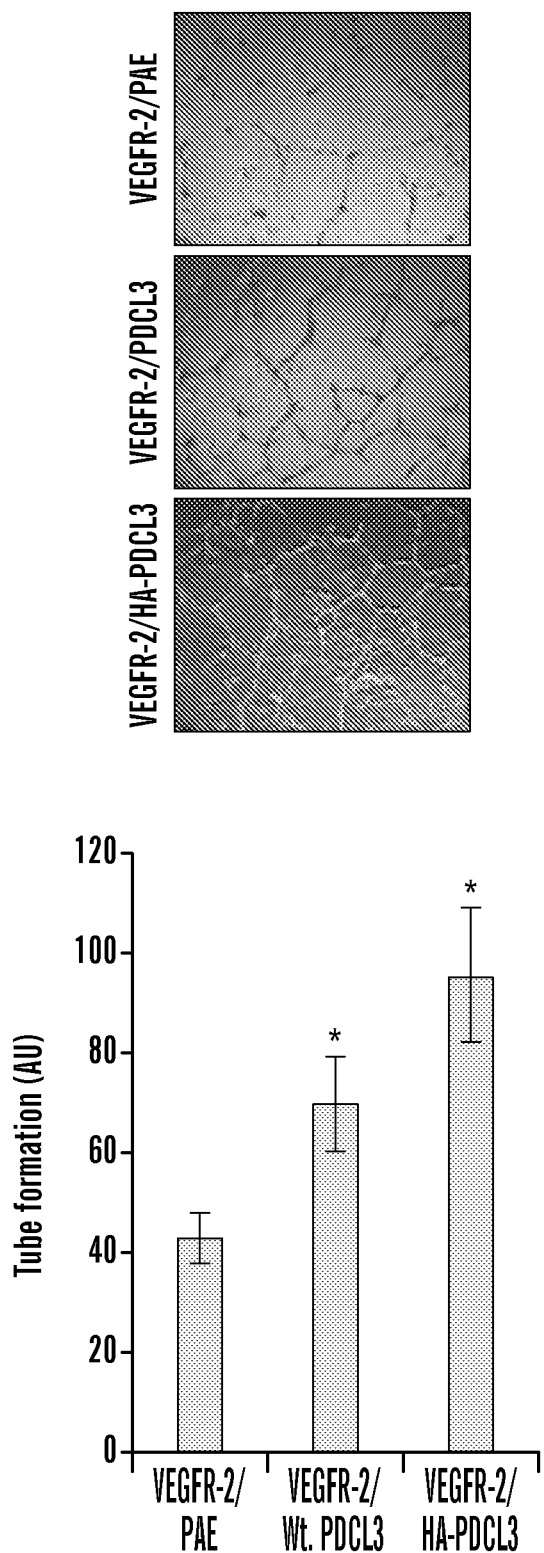

Acetylation resistant HA-tagged PDCL3 also interacted strongly with VEGFR-2 compared to wild-type PDCL3 (FIG. 6A) and prevented VEGFR-2 from ubiquitination (FIGS. 6A, 6B). Over-expression of wild type and acetylation resistant HA-tagged PDCL3 in endothelial cells both increased angiogenesis/capillary tube formation, but acetylation resistant HA-tagged PDCL3 was more robust (FIG. 6C).

To examine the role of N-terminal methionine acetylation in PDCL3 expression in response to hypoxia, cells expressing wild-type PDCL3 or an acetylation resistant HA-tagged PDCL3 were incubated in hypoxic environment and half-life PDCL3 was assessed by CHX-chase assay. The results showed that wild-type PDCL3 expression is upregulated by hypoxia and remains highly stable (FIG. 9A), however, acetylation resistant HA-tagged PDCL3 remained stable and hypoxia did significantly increased its expression (FIG. 9B). Taken together, the data demonstrate that N-terminal methionine acetylation on PDCL3 contributes to its degradation and preventing its acetylation leads to increased stability, which leads to increased angiogenic responses in endothelial cells.

Figure 11A:
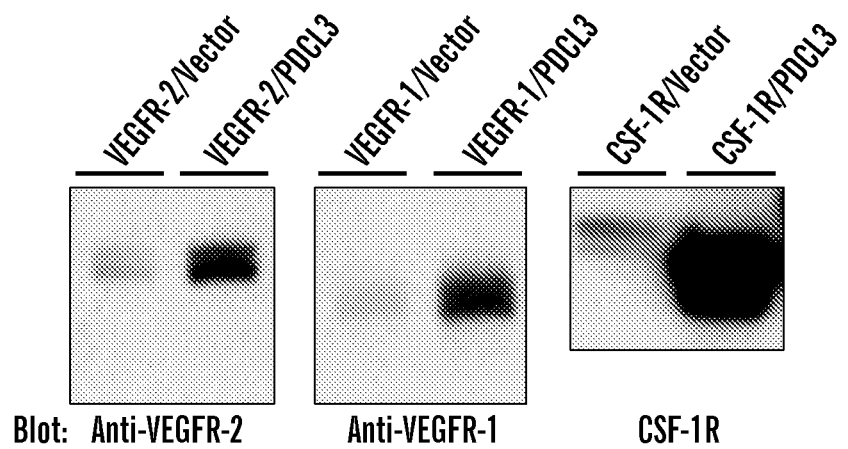
FIGS. 11A-11C demonstrate that PDCL3 increases expression of receptor tyrosine kinases. HEK-293 cells engineered to express various receptors in the background of PDCL3 or control (vector). Cell lysates blotted for receptors using specific anti-receptor antibodies as indicated (FIG. 11A), anti-Myc for PDCL3 (FIG. 11B), and for protein loading control (FIG. 11C).
Figure 11B:
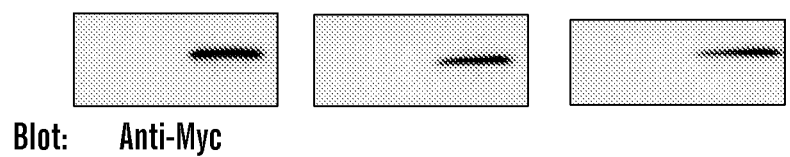
Figure 11C:

Further, expression of three major cell surface receptors including VEGFR-1, VEGFR-2, and CSF-1R was examined. As demonstrated herein, expression of PDCL3 markedly increased expression of VEGFR-1, VEGFR-2 and CSF-1R in HEK-293 cells (FIG. 11A).

Figure 12A:
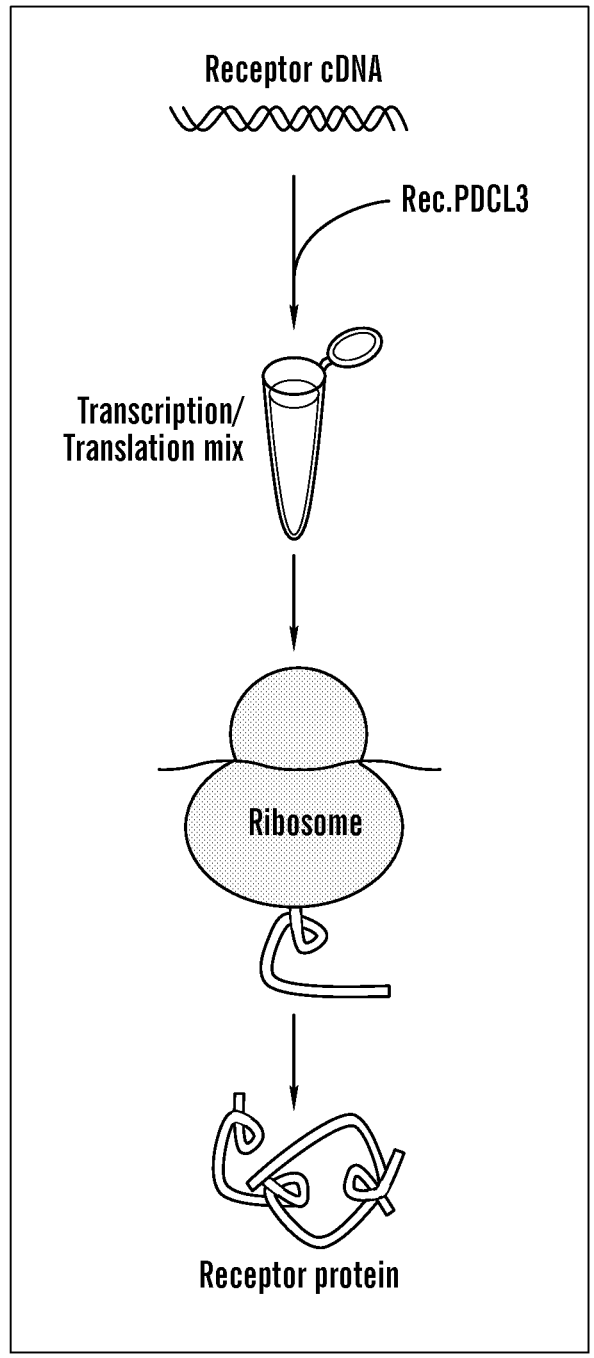
FIGS. 12A-12B demonstrate that PDCL3 increases expression of receptor tyrosine kinases in cell-free protein expression system (rabbit reticulocyte based transcription/translation system).
Figure 12B:
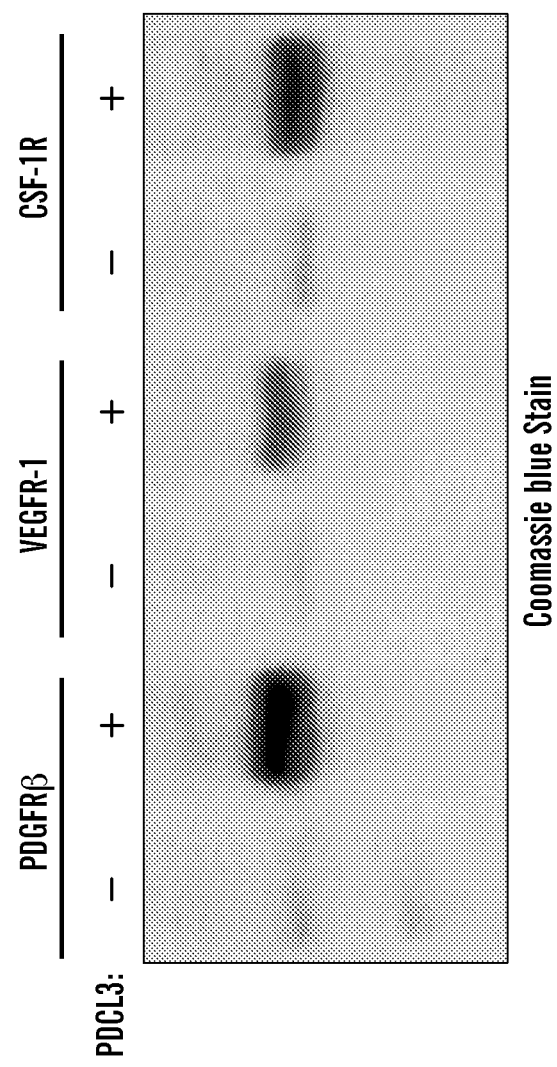

To test whether PDCL3 also could increase expression of cell surface receptors in a cell-free protein synthesis system, the effect of PDCL3 in a rabbit reticulocyte system was tested. Adding recombinant PDCL3 protein to a commercially available in vitro translation system (The TNT® Quick Coupled Transcription/Translation System, Promega, Inc.) also significantly increased expression of VEGFR-1, CSF-1R and PDGFR3 (FIG. 12B). Taken together, these data demonstrate that the use of PDCL3 for protein production for therapeutic and research use significantly increases the yield and hence can reduce the cost of production.

Accordingly, provided herein, in some aspects, are novel compositions comprising engineered PDCL3 polypeptides having enhanced chaperone activity, recombinant cells comprising such engineered PDCL3 polypeptides having enhanced chaperone activity, and methods thereof for therapeutic protein production and in vitro protein synthesis.

In some aspects, provided herein are compositions comprising engineered PDCL3 polypeptides having enhanced chaperone activity, and nucleic acids encoding such engineered PDCL3 polypeptides.

As used herein, an "engineered PDCL3 polypeptide" refers to a polypeptide encoding PDCL3 or a variant thereof that is unable to undergo N-terminal acetylation, thereby stabilizing PDCL3 and enhancing PDCL3 chaperone activity. Assays to measure the chaperone activity of a given engineered PDCL3 polypeptide are known in the art and non-limiting examples are provided herein. As used herein, a "variant" or "derivative" of an engineered PDCL3 polypeptide is a polypeptide in which one or more physical, chemical, or biological properties has been altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which can result in changes in primary, secondary or tertiary structure. In some embodiments, an engineered PDCL3 polypeptide derivative comprises a functionally active fragment of PDCL3. As is understood by one of ordinary skill in the art, any such engineered PDCL3 polypeptide derivative or fragment thereof exhibits one or more chaperone protein activities as described herein, such enhanced stability/decreased degradation and/or ability to stabilize VEGFR2, relative to a non-engineered Modified engineered PDCL3 polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

Naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Preferred conservative substitutions for use in the PDCL3 antagonist polypeptides described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of these aspects and all such aspects described herein, the engineered PDCL3 is acetylation resistant. In some embodiments of these aspects and all such aspects described herein, the engineered PDCL3 comprises a modification at the N-terminal methionine. In some embodiments of these aspects and all such aspects described herein, the modification at the N-terminal methionine is an acetylation-resistant N-terminal methionine. In some embodiments of these aspects and all such aspects described herein, the modification at the N-terminal methionine is insertion of one or more amino acids prior to or at the N-terminal methionine. In some such embodiments, the insertion of one or more amino acids is a tag.

Provided herein, in some aspects, are recombinant cells for enhancing expression of a recombinant protein product comprising a host cell comprising a nucleic acid sequence encoding an engineered PDCL3 polypeptide. In some embodiments of these aspects and all such aspects described herein, the host cell further comprises a nucleic acid sequence encoding a recombinant protein of interest.

In some aspects, provided herein are recombinant cells for enhancing expression of a recombinant protein product comprising a host cell comprising: a nucleic acid sequence encoding an engineered PDCL3 polypeptide and a nucleic acid sequence encoding a recombinant protein of interest.

In some embodiments of these aspects and all such aspects described herein, the host cell is a mammalian host cell. In some embodiments of these aspects and all such aspects described herein, the mammalian host cell is selected from VERO, BHK, HeLa, CV1 (including Cos), MDCK, 293, 3T3, myeloma cell lines (e.g., NSO, NS1), PC12, WI38, and Chinese hamster ovary (CHO) cell and cell lines. In some embodiments of these aspects and all such aspects described herein, the mammalian host cell is a human cell, such as a HeLa cell. In some embodiments of these aspects and all such aspects described herein, the mammalian host cell is a CHO (Chinese Hamster Ovary) cell. In some embodiments of these aspects and all such aspects described herein, the host cell is stably transformed with the nucleic acid sequence encoding the engineered PDCL3 polypeptide. In some embodiments of these aspects and all such aspects described herein, the host cell is stably transformed with the nucleic acid sequence encoding the recombinant protein of interest.

The terms "cell lines," "host cells," and "host cells lines" refer to cells that can be genetically engineered to express a nucleic acid sequence encoding an engineered PDCL3 polypeptide and/or a nucleic acid sequence encoding a recombinant protein of interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express an engineered PDCL3 polypeptide, a desired recombinant polypeptide or protein of interest, or both. Methods and vectors for genetically engineering cells and/or cell lines to express a polypeptide of interest are well known to those of skill in the art; for example, various techniques are illustrated in Current Protocols in Molecular Biology, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69.

Animal cell lines are derived from cells whose progenitors were derived from a multicellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), Blood 88:2004-2012; Kaufman et al. (1988), J. Biol Chem 263: 6352-6362; McKinnon et al. (1991), J Mol Endocrinol 6:231-239; Wood et al. (1990), J. Immunol. 145:3011-3016). The dihydrofolate reductase (DHFR)-deficient mutant cell lines (Urlaub et al. (1980), Proc Natl Acad Sci USA 77: 4216-4220), DXB11 and DG-44, are desirable CHO host cell lines because the efficient DHFR selectable and amplifiable gene expression system allows high level recombinant protein expression in these cells (Kaufman R. J. (1990), Meth Enzymol 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

The term "mammalian host cell" is used to refer to a mammalian cell which is capable of being transfected with a nucleic acid sequence and then of expressing a selected recombinant protein of interest. The term includes the progeny of the parent cell, whether or not the progeny is identical in morphology or in genetic make-up to the original parent, so long as the selected gene is present. Accordingly, suitable mammalian cells for use in embodiments of the various aspects described herein, include, but are not limited to, Chinese hamster ovary (CHO) cells, baby hamster kidney (BHK) cells, human HeLa cells, monkey COS-1 cell, human embryonic kidney 293 cells, mouse myeloma NSO and human HKB cells (U.S. Pat. No. 6,136,599). The other cell lines are readily available from the ATCC.

The term "recombinant" when used with reference to a cell indicates that the cell replicates a heterologous nucleic acid, or expresses a peptide or protein encoded by a heterologous nucleic aci, such as a nucleic acid sequence encoding an engineered PDCL3 polypeptide and/or a nucleic acid sequence encoding a recombinant protein of interest. Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell.

As used herein, the terms "recombinant cell," "recombinant cell line," or "modified cell line" refers to a cell line either transiently or stably transformed with one or more nucleic acid constructs, as described herein. Polynucleotides, genetic material, recombinant DNA molecules, expression vectors, and such, used in the compositions and methods described herein can be isolated using standard cloning methods such as those described by Sambrook et al. (Molecular Cloning: A Laboratory Manual, Second Edition, Cold Spring Harbor, N.Y., 1989; which is incorporated herein by reference). Alternatively, the polynucleotides coding for a recombinant protein product used in the compositions and methods described herein can be synthesized using standard techniques that are well known in the art, such as by synthesis on an automated DNA synthesizer.

Peptides, polypeptides and proteins that are produced by recombinant animal cell lines using the cell culture compositions and methods described herein can be referred to as "recombinant protein of interest," "recombinant peptide," "recombinant polypeptide," and "recombinant protein." The expressed protein(s) can be produced intracellularly or secreted into the culture medium from which it can be recovered and/or collected. Accordingly, the term "recombinant protein of interest" refers to a protein or fragment thereof expressed from an exogenous nucleic acid sequence introduced into a host cell.

Examples of recombinant proteins of interest that can be produced with the compositions and methods described herein include, for example, proteins comprising amino acid sequences identical to or substantially similar to all or part of one of the following proteins: VEGFR2, tumor necrosis factor (TNF), flt3 ligand (WO 94/28391), erythropoeitin, thrombopoeitin, calcitonin, IL-2, angiopoietin-2 (Maisonpierre et al. (1997), Science 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; Ruegg and Pytela (1995), Gene 160:257-62) growth hormone, insulin, insulinotropin, insulin-like growth factors, parathyroid hormone, interferons including a-interferons, γ-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-.beta., leukemia inhibitory factor, and oncostatin-M. Descriptions of proteins that can be produced according to the inventive methods may be found in, for example, Human Cytokines: Handbook for Basic and Clinical Research, all volumes (Aggarwal and Gutterman, eds. Blackwell Sciences, Cambridge, Mass., 1998); Growth Factors: A Practical Approach (McKay and Leigh, eds., Oxford University Press Inc., New York, 1993); and The Cytokine Handbook, Vols. 1 and 2 (Thompson and Lotze eds., Academic Press, San Diego, Calif., 2003).

Additional examples of recombinant proteins of interest that can be produced with the compositions and methods described herein include, for example, proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other recombinant proteins of interest that can be produced using the compositions and methods described herein include proteins comprising all or part of the amino acid sequences of differentiation antigens (referred to as CD proteins) or their ligands or proteins substantially similar to either of these. Such antigens are disclosed in Leukocyte Typing VI (Proceedings of the VIth International Workshop and Conference, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the compositions and methods described herein. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

Examples of antibodies that can be produced using the compositions and methods described herein include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1.alpha., IL-1.beta., IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-.beta. and analogs thereof (see U.S. Pat. Nos. 5,272, 064 and 5,149,792), VEGF, TGF, TGF-.beta.2, TGF-.beta.1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-.alpha., the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-.gamma.-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizumab, zalutumumab, and zanolimumab.

In other aspects, provided herein are methods for increasing protein production or for in vitro protein production comprising introducing into a host cell a nucleic acid sequence encoding an engineered PDCL3 polypeptide and a nucleic acid sequence encoding a recombinant protein of interest, thereby generating a recombinant cell for increasing production of the recombinant protein of interest, wherein the recombinant cell has increased production of the recombinant protein of interest relative to a cell in which the nucleic acid sequence encoding the engineered PDCL3 polypeptide was not introduced.

In some aspects, provided herein are methods for producing a mammalian host cell for enhanced expression of a recombinant protein of interest comprising: providing a mammalian cell having a nucleic acid sequence encoding for expression of a target recombinant protein; and transforming the mammalian cell with at least one expression vector comprising a nucleic acid sequence encoding an engineered PDCL3 polypeptide.

In some aspects, provided herein are methods for increasing production of a recombinant protein of interest comprising culturing a mammalian host cell, wherein the mammalian host cell comprises a nucleic acid sequence encoding a recombinant protein of interest and further introducing into said cell at least one nucleic acid sequence encoding an engineered PDCL3 polypeptide; and recovering the recombinant protein of interest produced by the cell.

In some embodiments of these methods and all such methods described herein, the nucleic acid sequence encoding the recombinant protein of interest and/or the nucleic acid sequence encoding the engineered PDCL3 polypeptide are introduced into the cell in one or more expression vectors.

In some embodiments of these methods and all such methods described herein, the nucleic acid sequence encoding the recombinant protein of interest and/or the nucleic acid sequence encoding the engineered PDCL3 polypeptide are introduced into the cell via transfection.

In some embodiments of these methods and all such methods described herein, the host cell is stably transformed with the nucleic acid sequence encoding the recombinant protein of interest.

In some embodiments of these methods and all such methods described herein, the host cell is stably transformed with the nucleic acid sequence encoding the engineered PDCL3 polypeptide.

The methods described herein can be used to culture cells that express recombinant proteins of interest. The expressed recombinant proteins can be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in Remington's Pharmaceutical Sciences, 18th ed. 1995, Mack Publishing Company, Easton, Pa.

As used herein, the term "transfection" is used to refer to the uptake of an exogenous nucleic acid by a cell, and a cell has been "transfected" when the exogenous nucleic acid has been introduced inside the cell membrane. A number of transfection techniques are well known in the art and are disclosed herein. See, e.g., Graham et al., 1973, Virology 52:456; Sambrook et al., Molecular Cloning, A Laboratory Manual (Cold Spring Harbor Laboratories, 1989); Davis et al., Basic Methods in Molecular Biology (Elsevier, 1986); and Chu et al., 1981, Gene 13:197. Such techniques can be used to introduce one or more exogenous nucleic acids into suitable host cells.

Suitable techniques of transfection for use with the compositions and methods described herein include, but are not limited to calcium phosphate-mediated transfection, DEAE-dextran mediated transfection, and electroporation. Cationic lipid transfection using commercially available reagents including the Boehringer Mannheim Transfection Reagent (N.fwdarw.1-(2,3-Dioleoyloxy)propyl-N,N,N-trimethyl ammoniummethylsulfate, Boehringer Mannheim, Indianapolis, Ind.) or LIPOFECTIN or LIPOFECTAMIN or DMRIE reagent (GIBCO-BRL, Gaithersburg, Md.) can also be used.

The term "transformation" as used herein refers to a change in a cell's genetic characteristics, and a cell has been transformed when it has been modified to contain a new DNA. For example, a cell is transformed where it is genetically modified from its native state. Following transfection, the transforming nucleic acid can recombine with that of the cell by physically integrating into a chromosome of the cell, can be maintained transiently as an episomal element without being replicated, or can replicate independently as a plasmid. A cell is considered to have been stably transformed when the transforming nucleic acid is replicated with the division of the cell.

As used herein an "expression vector" refers to a DNA molecule, or a clone of such a molecule, which has been modified through human intervention to contain segments of DNA combined and juxtaposed in a manner that would not otherwise exist in nature. DNA constructs can be engineered to include a first DNA segment encoding an acetylation-resistant engineered PDCL3 polypeptide described herein operably linked to additional DNA segments encoding a desired recombinant protein of interest. In addition, an expression vector can comprise additional DNA segments, such as promoters, transcription terminators, enhancers, and other elements. One or more selectable markers can also be included. DNA constructs useful for expressing cloned DNA segments in a variety of prokaryotic and eukaryotic host cells can be prepared from readily available components or purchased from commercial suppliers.

Expression vectors can also comprise DNA segments necessary to direct the secretion of a polypeptide or protein of interest. Such DNA segments can include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptide from the mature protein as it passes through the secretory pathway. A recombinant protein of interest can contain a secretory signal sequence in its original amino acid sequence, or can be engineered to become a secreted protein by inserting an engineered secretory signal sequence into its original amino acid sequence. The choice of suitable promoters, terminators and secretory signals is well within the level of ordinary skill in the art. Expression of cloned genes in cultured mammalian cells and in E. coli, for example, is discussed in detail in Sambrook et al. (Molecular Cloning: A Laboratory Manual, Second Edition, Cold Spring Harbor, N.Y., 1989; which is incorporated herein by reference).

After transfection, the host cell can be maintained either transiently transformed or stably transformed with said nucleic acid or expression vector. Introduction of multiple nucleic acids or expression vectors, and selection of cells containing the multiple nucleic acids or expression vectors can be done either simultaneously or, more preferably, sequentially. The technique of establishing a cell line stably transformed with a genetic material or expression vector is well known in the art (Current Protocols in Molecular Biology). In general, after transfection, the growth medium will select for cells containing the nucleic acid construct by, for example, drug selection or deficiency in an essential nutrient, which is complemented by a selectable marker on the nucleic acid construct or co-transfected with the nucleic acid construct. Cultured mammalian cells are generally cultured in commercially available serum-containing or serum-free medium. Selection of a medium appropriate for the particular host cell used is within the level of ordinary skill in the art.

Suitable selectable markers for drug selection used with the compositions and methods described herein include, but are not limited to, neomycin (G418), hygromycin, puromycin, zeocin, colchine, methotrexate, and methionine sulfoximine.

Once a drug resistant cell population is established, individual clones may be selected and screened for high expressing clones. Methods of establishing cloned cell line are well known in the art, including, but not limited to, using a cloning cylinder, or by limiting dilution. Expression of the recombinant protein of interest from each clone can be measured by methods such as, but not limited to, immunoassay, enzymatic assay, or chromogenic assay. A cell line stably transformed with a first nucleic acid construct may be then used as host cell for transfection with a second or more nucleic acid constructs, and subjected to different drug selections.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells can be cultured in suspension or while attached to a solid substrate. Fluidized bed bioreactors, hollow fiber bioreactors, roller bottles, shake flasks, or stirred tank bioreactors, with or without microcarriers, can be used.

As used herein, "cell culture medium" is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media can be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

In other aspects, provided herein are methods for promoting or stimulating angiogenesis in a subject in need thereof comprising administering to a subject an engineered PDCL3 polypeptide that enhances VEGFR2 stability.

In some embodiments of these aspects and all such aspects described herein, the engineered PDCL3 is acetylation resistant. In some embodiments of these aspects and all such aspects described herein, the engineered PDCL3 comprises a modification at the N-terminal methionine. In some embodiments of these aspects and all such aspects described herein, the modification at the N-terminal methionine is an acetylation-resistant N-terminal methionine. In some embodiments of these aspects and all such aspects described herein, the modification at the N-terminal methionine is insertion of one or more amino acids prior to or at the N-terminal methionine. In some such embodiments, the insertion of one or more amino acids is a tag.

As used herein, the terms "stimulating angiogenesis," "enhancing angiogenesis," "increasing angiogenesis," or "promoting angiogenesis" refer to an increase in at least one measurable marker of angiogenesis by at least 10%, at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more, in the presence of a engineered PDCL3 polypeptide described herein relative to that marker in the absence of such a polypeptide. The term "angiogenesis" is broadly defined as the creation or spouting of new blood vessels from pre-existing blood vessels and is characterized by endothelial cell proliferation and migration triggered by pro-angiogenic factors. Angiogenesis can be a good and necessary process, for example, in wound healing, or it can be an aberrant and undesired process with detrimental consequences, such as the growth of solid tumors and metastasis, and hemangiomas. Aberrant angiogenesis can lead to certain pathological conditions such as death, blindness, and disfigurement.

Accordingly, subjects in need of promoting or stimulating angiogenesis or promotion of neovascularization include, for example, subjects in need thereof tissue engineering constructs, tissue repair, regenerative medicine, and wound healing.

As used herein, "tissue engineering" refers to the use of a combination of cells, engineering and material methods, and suitable biochemical and physiochemical factors to improve or replace biological functions. Tissue engineering aims at developing functional cell, tissue, and organ substitutes to repair, replace or enhance biological function that has been lost due to congenital abnormalities, injury, disease, or aging, or repair fascia in hernias. The tissue that is engineered is used to repair or replace portions of or whole tissues (i.e., bone, cartilage, blood vessels, heart valves, bladder, diaphragm, etc.). Often, the tissues involved require certain mechanical and structural properties for proper function. Tissue engineering also encompass the efforts to perform specific biochemical functions using cells within an artificially-created support system (e.g. an artificial pancreas, or a bioartificial liver). The term regenerative medicine is often used synonymously with tissue engineering, although those involved in regenerative medicine place more emphasis on the use of stem cells to produce tissues and on promoting repair in situ. Tissue regeneration aims to restore and repair tissue function via the interplay of living cells, an extracellular matrix and cell communicators.

In some embodiments, the engineered PDCL3 polypeptides as described herein are useful in methods and compostions to promote in vivo therapeutic neovascularization, for example for tissue repair and healing of chronic wound in humans. The human body has a great capacity to heal itself when damaged. However, sometimes, the body's innate healing function becomes impaired or reduced due to metabolic diseases such as diabetes, poor blood circulation, blocked or damaged blood vessels. Accordingly, in some embodiments, the engineered PDCL3 polypeptides as described herein can be used to artificially increase blood vessels and blood vessel growth in the damaged area, by de novo formation of blood vessels and also stimulates new blood vessels formation from existing ones, via stabilization of VEGFR2. The new blood vessels bring oxygen, nutrients and growth factors to stimulate the body's own natural healing process by activating the body's inherent ability to repair and regenerate. In vivo therapeutic neovascularization helps speed up healing and helps injuries that will not heal or repair on their own. In vivo therapeutic neovascularization can be used to heal broken bones, severe burns, chronic wounds, heart damage, nerve damage, damaged tissue of the heart, muscles, skin, adipose tissue, brain, liver, lungs, intestines, limbs, and kidneys to name a few.

In some embodiments, the engineered PDCL3 polypeptides as described herein can be administered to a subject concurrent with, or prior to, or post-transplantation of an organ, such as a lung transplant, cardiac transplant, heart-lung transplant and other organ transplantations.

In some embodiments, the methods comprising the engineered PDCL3 polypeptides as described herein can optionally include growth, differentiation, and/or other pro-angiogenesis factors that are known in the art to stimulated cell proliferation, differentiation, and angiogenesis the cells at the site where the composition is delivered. Examples of such pro-angiogenic factors which can be used in combination with a pro-angiogenic agent as described herein include, but are not limited to Angiopoietin-1 (Ang-1), bFGF, EGF, Fibrinogen, Fibronectin, Heparanase, HGF, IGF-1, IGF BP-3, PDGF, VEGF-A, VEGF-C and vitronection. Other pro-angiogenic factors are disclosed herein, and include, but are not limited to E-cadherin, angiogenin, fibroblast growth factors: acidic (aFGF) and basic (bFGF), heparanase, hepatocyte growth factor (HGF), insulin-like growth factor-1 (IGF-1), IGF BP-3, PDGF, VEGF-A VEGF-C, pigment epithelium-derived factor (PEDF), vitronection, leptin, trefoil peptides (TFFs), CYR61 (CCN1) and NOV (CCN3), leptin, midkine, placental growth factor platelet-derived endothelial cell growth factor (PD-ECGF), platelet-derived growth factor-BB (PDGF-BB), pleiotrophin (PTN), progranulin, proliferin, transforming growth factor-alpha (TGF-alpha), transforming growth factor-beta (TGF-beta), tumor necrosis factor-alpha (TNF-alpha), c-Myc, granulocyte colony-stimulating factor (G-CSF), stromal derived factor 1 (SDF-1), scatter factor (SF), osteopontin, stem cell factor (SCF), matrix metalloproteinases (MMPs), thrombospondin-1 (TSP-1), and inflammatory cytokines and chemokines that are inducers of angiogenesis and increased vascularity, eg. CCL2 (MCP-1), interleukin-8 (IL-8) and CCL5 (RANTES). The pro-angiogenic factors can be used in conjunction with any and all combinations of an engineered PDCL3 polypeptide as described herein, for example, pro-angiogenic factors can be administered within the same composition as, or administered to a subject substantially at the same time (i.e. shortly before or shortly after) the administration of, a composition comprising at least one pro-angiogenic agent.

In some embodiments, a composition comprising the engineered PDCL3 polypeptides as described herein can be implanted in a tissue in need of vascularization or angiogeneis by direct injection of the composition. Direct injection is useful for the repair of ischemic tissue, for example, cardiac muscles, blood vessels, kidney, liver, bones, ischemic limb disease, brain (in the case of stroke), the pancreas and connective and support tissues such as ligaments, muscles, tendons and those tissues, such as the collagen-containing tissues which encapsulate organs, to name a few. Ischemia in a tissue can be determined by methods known to one skilled in the art, such as SPECT and diffusion/perfusion MRI, ankle-brachial index (ABI), Doppler ultrasound, segmental pressures and waveforms, duplex ultrasound, and transcutaneous oxygen pressure. Methods of direct implantation of stem cells for tissue repair are described in Shake J G et, al. 2002 (Ann Thorac Surg. 73:1919-25), Yoshinori Miyaharal, et. al., 2006 (Nature Medicine 12, 459-465), Atta Behfar, et. al., 2005 (Ann. N.Y. Acad. Sci. 1049: 189-198), Luciano C. Amado, et. al., 2005, (PNAS, 102: 11474-9), Khalil P N, et. al., 2007, (Gastroenterology. 132:944-54), Lee R H, et. al., 2006 (Proc Natl Acad Sci USA.; 103:17438-43), and Chamberlain J., et. al., 2007, (Hepatology. 2007 Aug. 17, in press), S. P. Bruder, et. al., 1998, (J. Bone and Joint Surgery 80:985-96), Pignataro G., et. al., J. Cereb Blood Flow Metab. 2007 May; 27(5): 919-27 and are hereby incorporated by reference.

The engineered PDCL3 polypeptides described herein can be administered to a subject in need thereof by any appropriate route which results in an effective treatment in the subject. As used herein, the terms "administering," and "introducing" are used interchangeably and refer to the placement of an engineered PDCL3 polypeptides into a subject by a method or route which results in at least partial localization of such agents at a desired site, such as a site where angiogenesis is desired, such that a desired effect(s) is produced.

In some embodiments, the engineered PDCL3 polypeptide is administered to a subject by any mode of administration that delivers the agent systemically or to a desired surface or target, and can include, but is not limited to, injection, infusion, instillation, and inhalation administration. To the extent that engineered PDCL3 polypeptides can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

For the clinical use of the methods described herein, administration of the engineered PDCL3 polypeptides can include formulation into pharmaceutical compositions or pharmaceutical formulations for parenteral administration, e.g., intravenous; mucosal, e.g., intranasal; ocular, or other mode of administration. In some embodiments, the engineered PDCL3 polypeptides described herein can be administered along with any pharmaceutically acceptable carrier compound, material, or composition which results in an effective treatment in the subject. Thus, a pharmaceutical formulation for use in the methods described herein can contain an engineered PDCL3 polypeptide as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of engineered PDCL3 polypeptides. Each carrier must be "acceptable" in the sense of being compatible with the other ingredients of the formulation and not injurious to the patient. The terms "excipient", "carrier", "pharmaceutically acceptable carrier" or the like are used interchangeably herein.

The engineered PDCL3 polypeptides described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally engineered PDCL3 polypeptides can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Therapeutic formulations of the engineered PDCL3 polypeptides described herein can be prepared for storage by mixing an engineered PDCL3 polypeptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary lyophilized anti-VEGF antibody formulations are described in WO 97/04801, expressly incorporated herein be reference.

Optionally, but preferably, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The therapeutic formulations of the compositions comprising engineered PDCL3 polypeptides described herein can also contain more than one active compound as necessary for the particular indication being treated, preferably those with complementary activities that do not adversely affect each other.

The active ingredients of the therapeutic formulations of the compositions comprising engineered PDCL3 polypeptides described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release preparations can be used. Suitable examples of sustained-release preparations include semipermeable matrices of solid hydrophobic polymers containing the engineered PDCL3 polypeptide in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The therapeutic formulations to be used for in vivo administration, such as parenteral administration, in the methods described herein can be sterile, which is readily accomplished by filtration through sterile filtration membranes, or other methods known to those of skill in the art.

The engineered PDCL3 polypeptides are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" of the engineered PDCL3 polypeptide to be administered will be governed by such considerations, and refers to the minimum amount necessary to ameliorate, treat, or stabilize, the disorder.

Depending on the type and severity of the disease, about 1 g/kg to 100 mg/kg (e.g., 0.1-20 mg/kg) of an engineered PDCL3 polypeptides is an initial candidate dosage for administration to a subject, whether, for example, by one or more separate administrations, or by continuous infusion. A typical daily dosage might range from about 1 µg/kg to about 100 mg/kg or more, depending on the factors mentioned above. Particularly desirable dosages include, for example, 5 mg/kg, 7.5 mg/kg, 10 mg/kg, and 15 mg/kg. The progress of using the methods described herein can be easily monitored by conventional techniques and assays.

The duration of a therapy using the methods described herein will continue for as long as medically indicated or until a desired therapeutic effect (e.g., those described herein) is achieved. In certain embodiments, the engineered PDCL3 polypeptides described herein is continued for 1 month, 2 months, 4 months, 6 months, 8 months, 10 months, 1 year, 2 years, 3 years, 4 years, 5 years, 10 years, 20 years, or for a period of years up to the lifetime of the subject.

The engineered PDCL3 polypeptides described herein are administered to a subject, e.g., a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration is particularly desired if extensive side effects or toxicity is associated with the use of the engineered PDCL3 polypeptide. An ex vivo strategy can also be used for therapeutic applications in some embodiments. Ex vivo strategies involve transfecting or transducing cells obtained from a subject with a polynucleotide encoding an engineered PDCL3 polypeptide. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

In some embodiments, the engineered PDCL3 polypeptide is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In some embodiments, the antibody or antibody fragment thereof is suitably administered by pulse infusion, particularly with declining doses of the antibody. Preferably the dosing is given by injections, most preferably intravenous or subcutaneous injections, depending in part on whether the administration is brief or chronic.

In some embodiments, the engineered PDCL3 polypeptide is administered locally, e.g., by direct injection and the injections can be repeated periodically.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a need for increased angiogenesis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "effective amount" as used herein refers to the amount of am engineered PDCL3 polypeptides, needed to alleviate at least one or more symptom of the disease or disorder, and relates to a sufficient amount of pharmacological composition to provide the desired effect, i.e., enhance or stimulate the formation of new blood vessels. The term "therapeutically effective amount" therefore refers to an amount of an engineered PDCL3 polypeptide, using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular. As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the invention described herein are further illustrated by the following examples which should not be construed as limiting.

EXAMPLES

Example 1

The formation of new blood vessels is initiated by activation of vascular endothelial growth factor receptor-2 (VEGFR-2). Expression of VEGFR-2 is generally low in healthy adult blood vessels, but markedly increased in pathological circumstances. To date, little is known about the posttranslational regulation of expression of VEGFR-2. The studies described herein were designed to determine role of phosducin like 3 (PDCL3) in VEGFR-2 expression and mechanisms involved.

As described herein, we have identified PDCL3 as a key chaperone protein present at the endoplasmic reticulum, where it interacts with the newly synthesized VEGFR-2 and increases its expression by assisting its maturation. PDCL3 expression is up-regulated by hypoxia, a principle inducer of angiogenesis and its upregulation promotes expression of functional VEGFR-2. PDCL3 undergoes N-terminal methionine acetylation, a modification that is important for its abundance. A mutant form of PDCL3 that could not be acetylated, strongly interacted with VEGFR-2, was resistant to hypoxia-dependent upregulation and strongly increased VEGF-dependent endothelial cell tube formation. Moreover, provided herein is evidence that PDCL3 plays important role in angiogenesis in vivo.

As demonstrated herein, PDCL3 activity regulates expression of VEGFR-2. Hypoxia regulates expression of PDCL3 in endothelial cells and its expression is required for angiogenesis. N-terminal acetylation regulates hemostasis of PDCL3. The data described herein provide new insights for previously unrecognized function of PDCL3 in angiogenesis.

Angiogenesis, the formation of new blood vessels, plays a central role in embryonic development, wound healing, tumor growth, and neovascular ocular diseases. Proteins that promote angiogenesis play central roles in the onset and progression of tumor progression and ocular neovascularization and retinopathies. The expression of unique blends of proteins in endothelial cells with pro- and anti-angiogenesis functions regulates angiogenesis and disruption in the activity or expression of these proteins so called "angiogenic switch" is responsible for pathological angiogenesis[1-3]. To maintain normal angiogenesis endothelial cells must possess mechanisms to control homeostasis or proteostasis of pro- and anti-angiogenesis proteins.

The research directed toward understanding the molecular mechanisms of angiogenesis and systematically characterizing vascular endothelial growth factor (VEGF) and signaling of its key receptor tyrosine kinase, VEGFR-2, also called kinase insert domain receptor (KDR) or fetal liver kinase 1 (FLK-1), in pre-clinical and clinical settings has provided substantial mechanistic insight into pathological angiogenesis[4,5]. Consequently, inhibition of the VEGFR-2 signaling is being intensely explored as a therapeutic target[1,6-8]. In general, the balance between endogenous pro-angiogenic and anti-angiogenic factors controls angiogenesis, such that endothelial cell growth is normally restrained. However, in pathologic angiogenesis, a shift occurs in the balance of regulators where expression and or activation of pro-angiogenic factors such as VEGF and its canonical receptors are significantly upregulated, which subsequently results in exorbitant angiogenesis[9-11].

VEGFR-2 is an essential mediator of VEGF-initiated angiogenesis and plays a pivotal role in regulating multiple signaling pathways in endothelial cells that modulates the core angiogenic responses such as proliferation, migration and capillary tube formation[6,12]. VEGF-induced posttranslational modifications (PTMs) on VEGFR-2 such as tyrosine and serine/threonine phosphorylation, ubiquitination, and methylation confer VEGFR-2 as a multi-potent regulator of angiogenesis. These PTMs subsequently arbitrate the outcome of angiogenic signaling and homoeostasis of mature VEGFR-2 protein in endothelial cells[1,13]. The abundance of mature cell surface VEGFR-2 protein is primarily regulated by mechanism that involves both increase in stabilization and destabilization of VEGFR-2. For example, VEGF-induced association of VEGFR-2 with protein βTrcp ubiquitin E3 ligase destabilizes VEGFR-2[14] whereas its association with Ephrin-B2 and vascular endothelial cadherin inhibits its internalization[15,16]. In some circumstances its interaction with cerebral cavernous malformation 3 (CCM3) and Hsp90 stabilizes the membrane bound cell surface VEGFR-2[17-18].

VEGFR-2 is only detectable at low levels in adult blood vessels[19]; however, its expression is markedly up-regulated in blood vessels in pathological conditions such as tumor growth, chronic inflammation, and wound repair[9,10,20]. Despite significant biological and clinical interest in VEGFR-2 signaling, the molecular mechanism governing its upregulation in pathological situations is not fully understood.

In general, newly synthesized cell surface receptors are transported through the endoplasmic reticulum (ER) membrane in an unfolded form where molecular chaperones and other enzymes facilitate their folding and assembly into their native conformation[21,22]. Proteins that cannot acquire proper native folding are often kept in the ER and rapidly degraded[23,24]. A recent study suggests that VEGFR-2 by interacting with the newly identified chaperone protein, PDCL3 avoids proteasomal degradation[25]. Association of PDCL3 with VEGFR-2 increases VEGFR-2 expression and its tyrosine phosphorylation in response to VEGF stimulation[25]. PDCL3 belongs to the phosducin family of proteins and members of the phosducin-like family proteins were initially identified as heterotrimeric G proteins binding partners[26-28]. In this study, we provide evidence that hypoxia regulates expression of PDCL3 in endothelial cells and its expression is required for angiogenesis.

PDCL3 Binds to Intracellular VEGFR-2 and Contributes to its Maturation

Figure 7A:
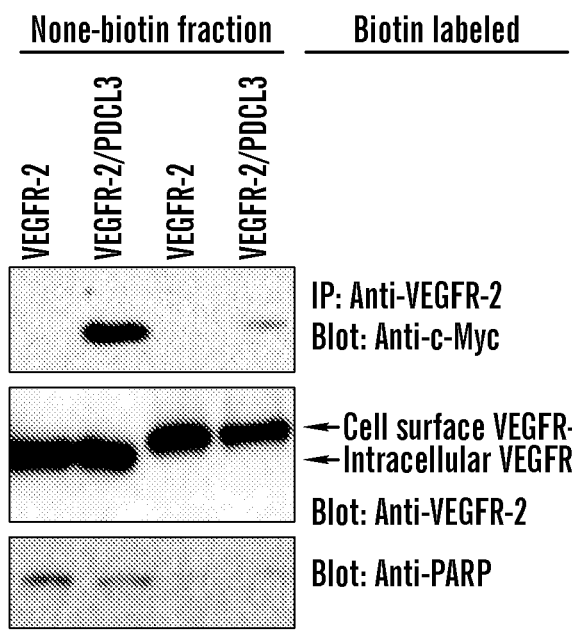
Figure 7B:
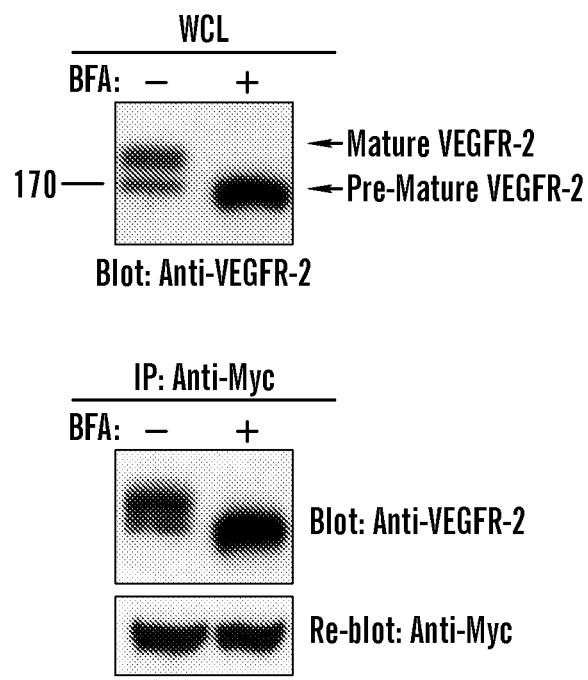
Figure 8B:
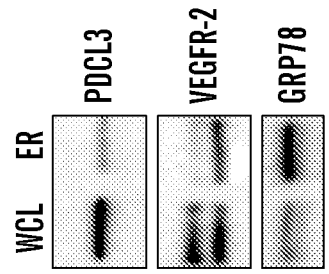
FIGS. 8A-8B demonstrate that PDCL3 co-localizes with KDEL (SEQ ID NO: 12).
Figure 8A:
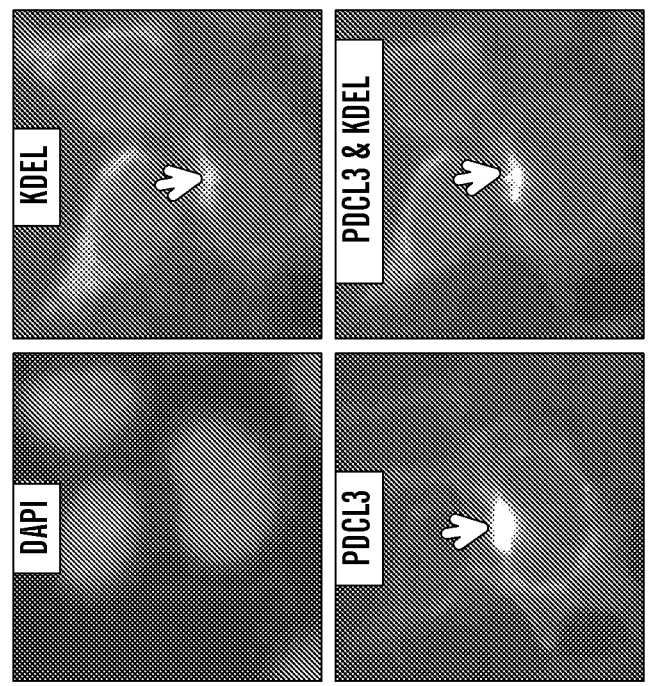

PDCL3 was identified as a chaperone protein that associates with VEGFR-2 and increases expression of VEGFR-2 by inhibiting its ubiquitination[25]. PDCL3 binds to premature/newly synthesized (partially glycosylated) and mature forms of VEGFR-2 (fully glycosylated)[25], indicating that PDCL3 interacts with the intracellular pool of VEGFR-2 rather than membrane bound VEGFR-2. Consistent with this, cell surface biotinylation assay showed that PDCL3 primarily associates with the intracellular pool of VEGFR-2 (FIG. 7A). Interestingly, treatment of cells with Brefeldin A (BFA), which inhibits anterograde transport of proteins from the ER to the Golgi apparatus[29,30] did not inhibit the binding of PDCL3 with VEGFR-2 (FIG. 7B), indicating that PDCL3 is localized in the ER compartments where it recognizes VEGFR-2. Moreover, immunofluorescence microscopy analysis showed that PDCL3 is present in perinuclear/cytoplasmic areas of cells (FIGS. 7C, 7D). Staining of cells with an ER-specific tracking dye showed that PDCL3 is localized in ER and cytoplasmic compartments (FIG. 7E) and was co-localized with KDEL (SEQ ID NO: 12), an ER/Golgi marker (FIG. 8A). Consistent with the immunofluorescence microscopy analysis, cellular fractionation also showed the presence of PDCL3 in the ER compartments (FIG. 8B).

Chaperone proteins interact with the newly synthesized nascent proteins and assist the folding/maturation[31]. We show herein that increasing expression of PDCL3 increases the abundance of premature and mature forms of VEGFR-2 in a dose-dependent manner (FIG. 1A) and silencing expression of PDCL3 significantly reduces expression of VEGFR-2 and its activation/tyrosine phosphorylation in response to VEGF stimulation (FIG. 1B). Molecular chaperones are thought to regulate protein stability by preventing aggregation of partially unfolded proteins and maintaining partially unfolded proteins in a state competent for refolding[32]. PDCL3 interacts strongly with heat-denatured VEGFR-2 and protects VEGFR-2 from trypsin digestion[25].

To examine the chaperone function of PDCL3, we measured thermo-induced aggregation of VEGFR-2. Incubation of immunoprecipitated VEGFR-2 in the presence of PDCL3 at 45° C. significantly reduced aggregation of VEGFR-2 in a time-dependent manner (FIG. 1C). To further demonstrate the chaperone effect of PDCL3 on VEGFR-2, we demonstrate that the recombinant PDCL3 protein significantly increases the yield of in vitro translated VEGFR-2 (FIG. 1E) and this effect of PDCL3 was further augmented by proteasome inhibitor, MG132 (FIG. 1F).

Figure 2C:
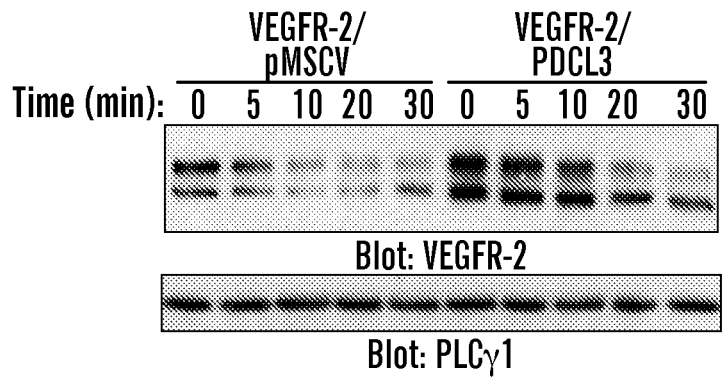
Figure 2D:
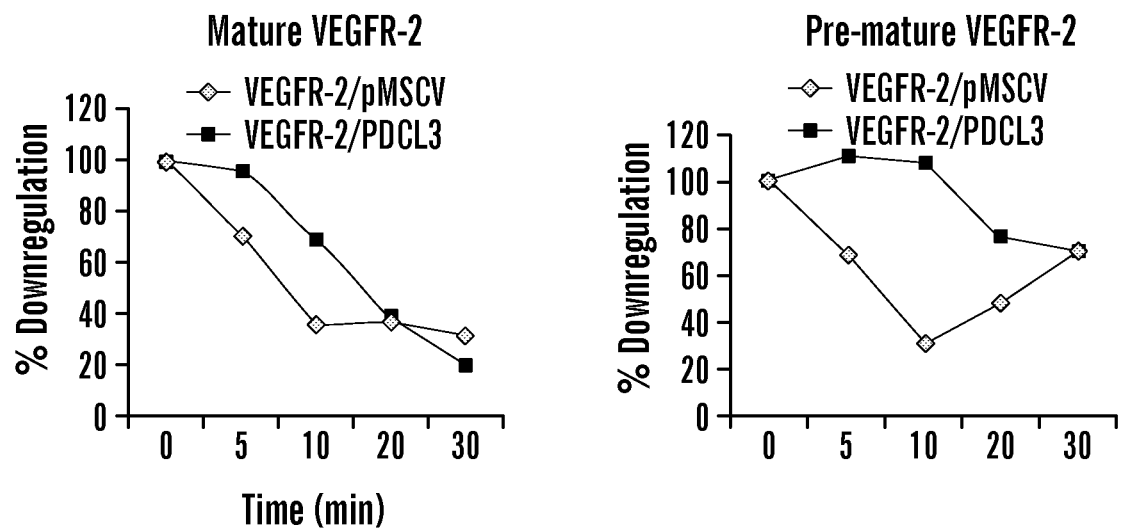

Given that PDCL3 interacts with the premature VEGFR-2, we tested the effect of PDCL3 on the stability of premature VEGFR-2, we treated cells expressing VEGFR-2 alone or co-expressing with PDCL3 with protein synthesis inhibitor, cycloheximide followed by stimulation of cells with VEGF for various time points. Cells were also stimulated with VEGF to downregulate the mature cell surface VEGFR-2 protein. VEGFR-2 is rapidly downregulated in response to ligand stimulation 14, 33. Cycloheximide treatment inhibited VEGFR-2 protein synthesis (as the presence of premature VEGFR-2 (low molecular weight) was diminished as function of time) (FIGS. 2A, 2C). However, the same treatment did not significantly inhibit the appearance of premature VEGFR-2 in cells co-expressing VEGFR-2 with PDCL3 (FIGS. 2A, 2B). The presence of premature VEGFR-2 persisted even when cells were treated with VEGF (FIGS. 2A, 2B). The presence of mature VEGFR-2 and the rate of VEGF-induced downregulation remained the same in the presence of CHX in cells expressing VEGF-2 alone or co-expressing VEGFR-2 with PDCL3 (FIGS. 2A, 2B). Unlike the observed effect of PDCL3 in cells treated with cycloheximide, in the absence of cycloheximide, cell surface exposed mature VEGFR-2 was downregulated in response to VEGF stimulation. However, the downregulation of VEGFR-2 in cells over-expressing PDCL3 was markedly slower (FIGS. 2C, 2D). Interestingly, the premature VEGFR-2 in cells over-expressing PDCL3 was mostly remained stable (FIGS. 2C, 2D). However, cells expressing VEGFR-2 alone, the levels of newly synthesized premature VEGFR-2 was initially reduced in response to VEGF treatment (up to 20 minutes stimulation) and then started to increase after 30 minutes of stimulation (FIGS. 2C, 2D), suggesting induction of new protein synthesis in response to downregulation of VEGFR-2. The data indicates that PDCL3 by interacting with VEGFR-2 extends the half-life of newly made VEGFR-2. Taken together, the data demonstrate that PDCL3 associates with premature/newly synthesized VEGFR-2 and contributes to its maturation.

PDCL3 Promotes Angiogenesis in Zebrafish

Figure 3D:
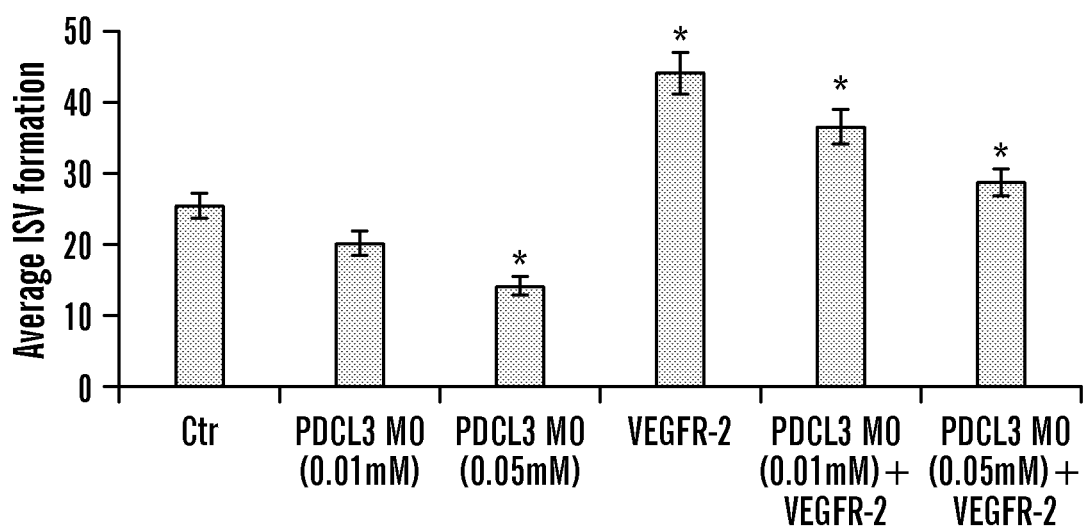

Given that PDCL3 increases expression of VEGFR-2, we hypothesized that over-expression of PDCL3 could promote angiogenesis in vivo. To this end, we decided to examine the functional importance of PDCL3 to angiogenesis in zebrafish. We used zebrafish to study angiogenesis due to its high conservation to humans and genetic and imaging capabilities 34, 35. Microinjection of in vitro translated human PDCL3 mRNA into one-stage zebrafish embryos significantly increased angiogenesis in a dose-dependent manner (FIG. 3A). Illustrated is the quantification of blood vessel formation in response to Microinjection of human pdcl3 mRNA (FIG. 3B). In contrast, silencing the expression of PDCL3 in zebrafish by morpholino significantly inhibited angiogenesis (FIG. 3C) and co-injection of pdcl3 morpholino with VEGFR-2 mRNA markedly reversed the effect of pdcl3 knockdown (FIG. 3C) indicating that VEGFR-2 is the primary downstream target of PDCL3. Shown is the quantification of vessel formation (FIG. 3D). Collectively, the data demonstrate that PDCL3 activity is required for angiogenesis in zebrafish.

Hypoxia Increases Expression of PDCL3

Because PDCL3 regulates abundance of VEGFR-2 and its over-expression in zebrafish promoted angiogenesis, we decided to examine whether expression of PDCL3 is upregulated in conditions such as hypoxia that triggers angiogenesis[36,37]. VEGFR-2 is generally expressed at low levels in most adult vessels but its expression is strongly upregulated in pathological circumstances such as hypoxia and ischemic conditions[38,39]. Exposure of endothelial cells to hypoxic environment (1% oxygen, 24 hours) significantly increased expression of PDCL3 (FIG. 4A). Similarly, expression of VEGFR-2 was also markedly increased in response to hypoxia (FIG. 4A). Likewise, treatment of cells with chemical hypoxia, cobalt chloride, similarly increased expression of PDCL3 and VEGFR-2 (FIGS. 9A-9B). To test whether, increased expression of VEGFR-2 in response to hypoxia is linked to induction of PDCL3 expression, we silenced expression of PDCL3 by siRNA and analyzed measured VEGFR-2 levels. The knockdown of PDCL3 reduced the hypoxia-mediated upregulation of VEGFR-2 (FIG. 4B).

To examine the effect of hypoxia on the expression of PDCL3 in vivo, we examined expression of PDCL3 in a well-characterized mouse model of hypoxia-induced angiogenesis[40]. In this model, the maximum neovascularization is observed at postnatal day 17, P17[41]. Immunohistochemistry analysis of ocular tissues showed that the expression of PDCL3 is highly upregulated in response to hypoxia particularly in the blood vessels of the retina (FIG. 4C), whereas its expression was relatively undetectable in normal mouse retinal tissue (FIG. 4C). Expression of VEGFR-2 also was significantly higher in the mouse ocular tissue exposed to hypoxia (FIG. 4C). The data demonstrate that hypoxia affects expression of PDCL3 and that up-regulation of PDCL3, in part, contributes to increased expression of VEGFR-2.

N-Terminal Methionine Acetylation Regulates PDCL3 Degradation

To examine further hypoxia-mediated expression of PDCL3, we analyzed possible posttranslational modification on PDCL3 by liquid chromatography-tandem mass spectrometry (LC-MS/MS) analysis. Our analysis revealed that PDCL3 was acetylated on the N-terminal methionine (FIG. 5A). Acetylation of N-terminal methionine is thought to regulate protein stability by serving as a degradation signal designated "N-degron"[42].

To examine the possible role of N-terminal methionine acetylation in expression of PDCL3, we generated an acetylation resistant PDCL3 construct by inserting an HA-tag at the N-terminal of PDCL3 (FIG. 5B). Despite using an equal amount of DNA constructs, expression of HA-tagged PDCL3 was higher compared to expression of wild-type PDCL3 (FIG. 5B). Given that N-terminal acetylation is linked to protein stability[43], we carried out a cycloheximide (CHX)-chase assay in which we analyzed half-life of PDCL3 after inhibition of its translation by CHX. The half-life of wild-type PDCL3 was relatively short (about 30 minutes) whereas acetylation resistant HA-tagged PDCL3 was quite stable up to 60 minutes (FIG. 5C), indicating that N-terminal methionine acetylation promotes degradation of PDCL3 and preventing its acetylation makes it more stable protein.

Acetylation resistant HA-tagged PDCL3 also interacted strongly with VEGFR-2 compared to wild-type PDCL3

(FIG. 6A) and prevented VEGFR-2 from ubiquitination (FIGS. 6A, 6B). Capillary tube formation is a hallmark of VEGFR-2 induced cellular responses in endothelial cells[44], hence we decided to examine whether over-expression of acetylation resistant HA-tagged PDCL3 in endothelial cells could increase VEGFR-2 dependent tube formation. Overexpression of wild type and acetylation resistant HA-tagged PDCL3 in endothelial cells both increased angiogenesis/capillary tube formation, but acetylation resistant HA-tagged PDCL3 was more robust (FIG. 6C).

To examine the role of N-terminal methionine acetylation in PDCL3 expression in response to hypoxia, cells expressing wild-type PDCL3 or acetylation resistant HA-tagged PDCL3 were incubated in hypoxic environment and half-life PDCL3 was assessed by CHX-chase assay. The results showed that wild-type PDCL3 expression is upregulated by hypoxia and remains highly stable (FIG. 9A), however, acetylation resistant HA-tagged PDCL3 was remained stable and hypoxia did significantly increased its expression (FIG. 9B). Taken together, the data demonstrate that N-terminal methionine acetylation on PDCL3 contributes to its degradation and preventing its acetylation leads to increased stability, which leads to increased angiogenic responses in endothelial cells.

Angiogenesis, the development of new blood vessels from pre-existing vasculature, contributes to the onset and development of various human diseases ranging from cancer to neovascular eye disorders[2]. A remarkable feature of angiogenesis is the ability of endothelial cells to proliferate rapidly in pathological circumstances, such as tumourigenesis, in response to intratumoral hypoxia by increasing expression of various angiogenic factors and others[38]. Intratumoral hypoxia promotes over-expression of VEGF ligands in tumor cells, and its tyrosine kinase receptors, particularly, VEGFR-2 in tumors and tumor-associated endothelium[45-47]. Upregulation of VEGFR-2 expression in various preclinical and clinical studies has been documented[47-50], however, the mechanisms by which VEGFR-2 expression is regulated at the posttranslational level remains poorly understood.

Figure 10:
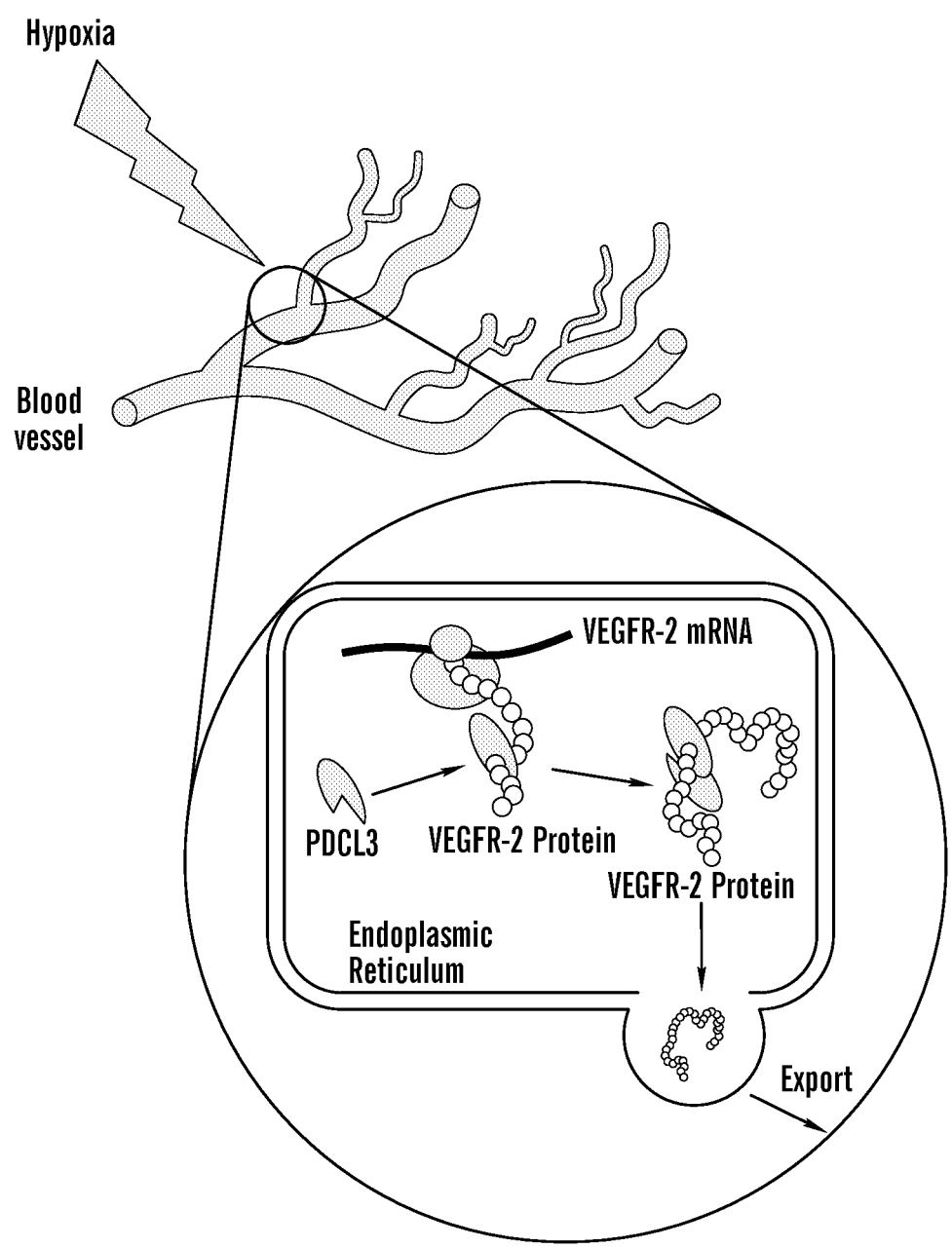
FIG. 10 is a schematic for a role for hypoxia in expression of VEGFR-2. PDCL3 expression is upregulated in response to hypoxia. Increased expression of PDCL3 contributes to elevated expression of VEGFR-2 by interacting with newly synthesized VEGFR-2. Association of PDCL3 with VEGFR-2 protects newly synthesized VEGFR-2 from degradation leading to an increase in the number of functional VEGFR-2 at the surface of endothelial cells. Elevated VEGFR-2 expression results in elevated angiogenic responses.

Our research described herein has uncovered PDCL3, a protein with chaperone activity, as a modulator of VEGFR-2 protein stability. These findings constitute a significant advance in our understanding of how hypoxia stimulates expression of VEGFR-2 by posttranslational mechanism ushering in a new paradigm in VEGFR-2 expression and angiogenesis. FIG. 10 is a schematic depicting our model of hypoxia-induced expression of VEGFR-2 through chaperone function of PDCL3.

Previously, PDCL3 was described as a cytoplasmic protein[25], we demonstrate that PDCL3 is present at both the endoplasmic reticulum (ER) and cytoplasmic compartments. Various probes including, ER-tracking dye and ER-specific marker, KDEL (SEQ ID NO: 12) and Brefeldin A, a chemical that inhibits anterograde transport of proteins from the ER to the Golgi apparatus, all demonstrate that in addition to cytoplasmic compartments, PDCL3 also is present at the ER. Chaperone proteins such as Hsp90s are present in various cellular compartments including, ER, mitochondria and cytoplasm[51]. The ER localized Hsp90 chaperone proteins associate with and assist the appropriate folding of nascent proteins[52]. Consistent with the chaperone function of PDCL3, the ER localized PDCL3 associates with newly synthesized VEGFR-2 where it protects VEGFR-2 from degradation. Consistent with this observation, our previous study has shown that over-expression of PDCL3 in endothelial cells increases, whereas, silencing its expression by siRNA significantly decreases expression of VEGFR-2. Similarly, depletion of PDCL3 increased ubiquitination of VEGFR-2, and its overexpression reduced ubiquitylation of VEGFR-2[25].

Although N-terminal acetylation has been linked to protein stability through the N-end-rule pathway[42], to date the role of N-terminal acetylation in mammalian cells remains poorly understood. Our data demonstrate that N-terminal methionine acetylation regulates stability of PDCL3 and as a result VEGFR-2 expression, a key receptor tyrosine kinase whose activity is associated with pathological angiogenesis such as cancer and various other diseases. PDCL3 stability appears to play an important role in angiogenesis, as its expression was upregulated by hypoxia, a master regulator of angiogenesis[25]. Furthermore, zebrafish experiments confirmed its biological importance to angiogenesis. Overexpression of PDCL3 in zebrafish increased and depleting its expression by morpholino inhibited angiogenesis. Similarly, over-expression of mutant PDCL3 unable to undergo N-terminal acetylation was significantly more potent than the wild type PDCL3 in its ability to stimulate angiogenesis in endothelial cells, further underscoring the biological significance of N-terminal acetylation in its function.

The N-terminal acetylation is considered a co-translational event, and is likely irreversible[43]. Mutant PDCL3 unable to undergo N-terminal acetylation is refractory to the effect of hypoxia, indicating that hypoxia, in part, might promote stability of PDCL3 by inhibiting acetylation of PDCL3.

N-terminal acetylation is considered a non-reversible posttranslational modification[42], and consistent with this notion, our quantitative MS analysis also showed that acetylation of PDCL3 is not inhibited by hypoxia, Hypoxia likely modulates stability of PDCL3 through inhibition of expression or activity of ubiquitin E3 ligase enzymes involved in the recognition of N-degron motif of PDCL3 that might target PDCL3 to ubiquitination-dependent proteasomal degradation In summary, the work presented herein indicates that perturbation in the proteostasis of VEGFR-2 could lead to unwanted angiogenesis. The discovery that PDCL3 expression is regulated by hypoxia and plays an important role in stability of VEGFR-2 and angiogenesis, appears to be part of hypoxia-sensing mechanism evolved to maintain physiological angiogenesis.

Materials and Methods

Reagents and Antibodies:

Rabbit Polyclonal anti-VEGFR-2 antibody was raised against amino acids corresponding to the kinase insert of VEGFR-2 (1). The following antibodies were purchased from SANTA CRUZ BIOTECHNOLOGY INC.; pre-adsorbed goat rabbit IgG(sc-2054), goat anti-mouse IgG(sc-2055) and goat anti-rat IgG(sc-2006) secondary antibodies conjugated to horseradish peroxidase (HRP), anti-c-myc (9E10)(sc-40), anti-HSP 70(W27)(sc-24), anti-PLC1(sc-81). Anti-PDCL3 antibody was purchased from NOVUS BIOLOGICAL or ABCAM. ER-specific dye was purchased from MILLIPORE. Brefeldin A (BFA) (87022601) and Cobalt chloride (60818) were purchased from SIGMA.

Cell Lines:

HEK-293 (human embryonic kidney epithelial cells) and PAE (porcine aortic endothelial) cells were grown in DMEM medium supplemented with 10% FBS plus antibiotics. HUVEC (Human umbilical vascular endothelial cells) were grown in the endothelial cell medium. Retroviruses were produced in 293-GPG packaging cells as described (1). For hypoxic experiments, cells were incubated at 1% oxygen, 95% nitrogen and 5% carbon dioxide for 24 hours at 37° C.

Plasmids and siRNA: Human Phosducin like protein 3 cDNA (PDCL3 also called PHLP2A) (Clone #3344703, accession #BC001021) was purchased from OPEN BIO-SYSTEMS and was cloned into expression vectors, pcDNA3.1/Myc-His(-) or retroviral pMSCV. Mutant PDCL3 was generated by removing the first methionine and adding HA tag and similarly was cloned into pcDNA3.1 and pMSCV vectors. PDCL3 siRNA (sc-94814) was purchased from Santa Cruz, Inc. The PDCL3 morpholino for zebrafish was 5'CGGTGTCTGCGTTTGGGTCCTGCAT3' (SEQ ID NO: 10) and synthesized by GENE TOOLS, LLC. Immunoprecipitation and Western blotting: Cells were prepared and lysed as described (1). Briefly, cells were washed twice with H/S buffer (25 mM HEPES, pH 7.4, 150 mM NaCl, and 2 mM Na3VO4) and lysed in lysis buffer (10 mM Tris-HCl, 10% glycerol, pH 7.4, 5 mM EDTA, 50 mM NaCl, 50 mM NaF, 1% Triton X-100, 1 mM phenylmethylsulfonyl fluoride [PMSF], 2 mM Na3VO4, and 20 µg/ml aprotinin). Whole cell lysates were subjected to immunoprecipitation or were directly subjected to western blotting analysis as indicated in the figure legends.

Cycloheximide-Chase Assay:

PAE cells expressing VEGFR-2 alone or together with PDCL3 were serum-starved for overnight followed by incubation of cells with serum-free DMEM medium containing cycloheximide (20 µg/ml, 90 min). Cells then were stimulated with VEGF for various times to downregulate cell surface VEGFR-2. Cells were lysed and whole cell lysates was blotted for VEGFR-2 using anti-VEGFR-2 antibody. For measuring half-life of PDCL3 and HA-tagged mutant PDCL3, cells were incubated with serum-free DMEM medium containing cycloheximide (20 µg/ml) for indicated times and cells were lysed and whole cell lysates was blotted for PDCL3.

Protein Aggregation Assay:

Aggregation of VEGFR-2 determined using PSA kit purchased from PROFOLDIN, Inc (Hudson, Mass.) and assay was performed according to manufacturer's guideline. PSA acts as a molecular rotor dye that rotates like a propeller without presence of protein aggregates and does not fluoresce. When the PSA dye binds to the aggregate, it is immobilized and slows down the rotational movement and inducing the dye to fluoresce. In brief, VEGFR-2 immunoprecipitated from HEK-293 cells and eluded from the protein-sepharose beads. The eluded VEGFR-2 protein was incubated in the 45° C. in the presence or absence of purified GST-PDCL3 for various time points. The Fluorescence intensity was measured at 610 nM.

Immunofluorescence Microcopy: HEK-293 cells expressing Myc-tagged PDCL3 or co-expressed with GFP-KDEL ("KDEL" disclosed as SEQ ID NO: 12) were grown in chamber slides. The slides were fixed in ice-cold methanol for 10 minutes at room temperature after washing once with 1×TBS buffer. The slides were blocked with 1% BSA in TBS buffer for 30 min the slides then were incubated in the primary antibody against human PDCL3 and ER-specific dye in 1% BSA in 1×TBS for 2 hours at room temperature with a gentle shaking. The mixture solution was decanted and the slides were washed with 1×TBS. After the wash, the slides were incubated with the secondary antibody FITC-conjugated against mouse in 1% BSA with 1×TBS for 1 hr at room temperature in dark with shaking. The secondary antibody solution was then decanted and washed three times with 1×TBS for 5 min each in dark. After rinsing in 1×TBS, the slides were mounted with VECTASHIELD Mounting Media with DAPI. The pictures were taken using NIKON DECONVOLUTION WIDE-FIELD EPIFLUORESCENCE SYSTEM.

Hypoxia-Induced Mouse Angiogenesis:

All experiments were performed in accordance with the NIH Guide for the Care and Use of Laboratory Animals, and all experimental procedures were approved by the Children Hospital Animal Care and Use Committee. Oxygen induced retinopathy of prematurity (OIR) was induced in C57BL/6J mice according to the protocol described (2). Briefly, postnatal day 7 (P7) pups and their mothers were transferred from room air to an environment of 75% oxygen for 5 days and afterward returned to room air. Abnormal pre-retinal neovascularization occurs after return to normoxia starting at around P17. The eye tissue used in this study was p17.

Synthesis of Capped mRNA:

The vectors were linearized with Not I restriction enzyme, treated with Proteinase K (SIGMA) and extracted with phenol. Linearized plasmid DNA (1 µg/µl) in RNAse-free water was used for in vitro capped mRNA synthesis using the MMESSAGE MMACHINE® SP6 kit (AMBION) according to manufacturer instructions and RNA subsequently was used to inject into zebrafish embryos.

Zebrafish Angiogenesis Assay:

Fli-eGFP-transgenic adult male and female zebrafish (*Danio rerio*) were housed in 14:19-h light-dark cycle at a temperature of (26.5° C.) and a pH of (7.0-7.4) in a controlled multi-tank recirculating water system (Aquatic Habitats, Apopka, Fla.). Fish were fed twice daily with live brine shrimp (Brine Shrimp Direct, Ogden, Utah) and flake food (TetraMin; Tetra, Blacksburg, Va.). A glass capillary needle attached to a Femtojet injector (EPPENDORF) was used for injecting RNA (10 or 5 ng/µl in approximately 10 pl) into 1- or 2-cell-stage embryos. The embryos were grown at 28° C. for 3 days. The embryos were examined after 28 or 50 hpf using Zeiss immunofluorescence microscope. The images of fish under same setting were obtained for 10 fish per group at every experiment and analyzed for the length of the tail vessels using IMAGE-PRO® software and for the tail vessel plexus fluorescent intensity using Image J software.

Mass Spectrometry Analysis:

PDCL3 was immunoprecipitated with anti-Myc antibody from HEK-293 cells ectopically expressing PDCL3. The immunoprecipitated proteins were subjected to proteolytic digestion (incubated at 37° C. for 4 h in the presence of trypsin) on a ProGest (Genomic Solutions). Samples were analyzed by nano LC/MS/MS on a Thermo Fisher LTQ Orbitrap XL. 30 µl of hydrolysate was loaded onto a 5 mm 75 µm ID C12 (Jupiter Proteo, Phenomenex) vented column at a flow-rate of 10 µL/min. Gradient elution was over a 15 cm 75 µm ID C12 column at 300 nL/min. The mass spectrometer was operated in data-dependent mode; the six most abundant ions were selected for MS/MS. The Orbitrap MS scan was performed at 60,000 FWHM resolution. MS/MS data were searched using a local copy of Mascot available on the worldwide web at matrixscience.com. Samples were processed in the Scaffold algorithm, available on the worldwide web at proteomesoftware.com, using DAT files generated by Mascot. Parameters for LTQ Orbitrap XL data require a minimum of 2 peptides matching per protein with minimum probabilities of 90% at the protein level and 50% at the corresponding peptide level.

Example 2

PDCL3 Regulates Expression of Cell Surface Proteins

The current methods of production of highly functional proteins in a large scale for pre-clinical and therapeutics applications are limited due to low yield and high cost. Based on our recent studies[25,55], we hypothesized, without wishing to be bound or limited by theory, that over-expression of PDCL3 in HEK-293 cells could be explored to increase expression of cell surface receptors. As a proof-of-concept, we examined expression of three major cell surface receptors including VEGFR-1, VEGFR-2, and CSF-1R. Our data demonstrated that expression of PDCL3 markedly increased expression of VEGFR-1, VEGFR-2 and CSF-1R in HEK-293 cells (FIG. 11A).

To test whether PDCL3 also could increase expression of cell surface receptors in a cell-free protein synthesis system, we tested the effect of PDCL3 in rabbit reticulocyte system. Adding recombinant PDCL3 protein to a commercially available in vitro translation system (The TNT® Quick Coupled Transcription/Translation System, Promega, Inc.) also significantly increased expression of VEGFR-1, CSF-1R and PDGFRβ (FIG. 12B). Taken together, our data demonstrate that the use of PDCL3 for protein production for therapeutic and research use significantly increases the yield and hence can reduce the cost of production.

Figure 13A:
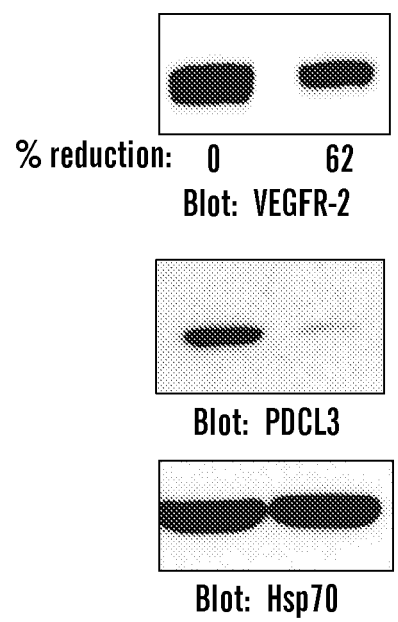
FIGS. 13A-13D demonstrate that reducing expression of PDCL3 in kidney tumor cells decreases tumor growth in vitro and that PDCL3 activity controls expression of VEGFR-2 and growth of kidney tumor 786-O cells.
Figure 13B:
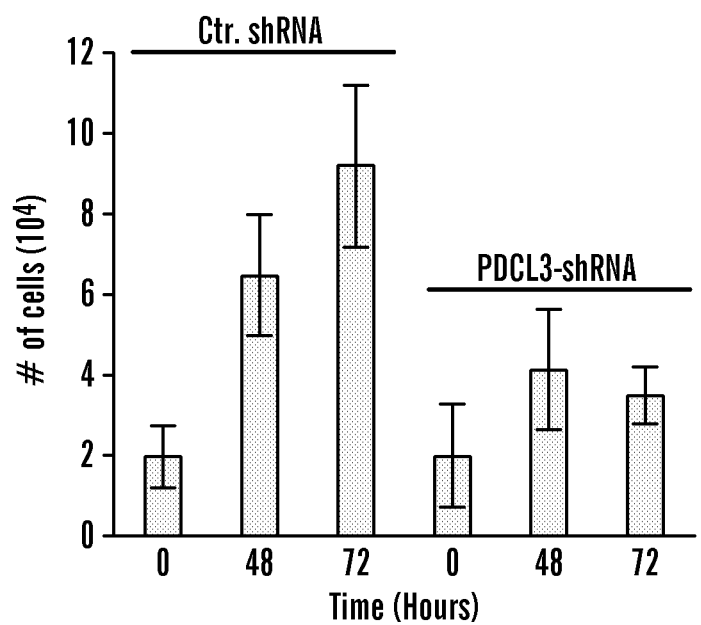
Figure 13C:
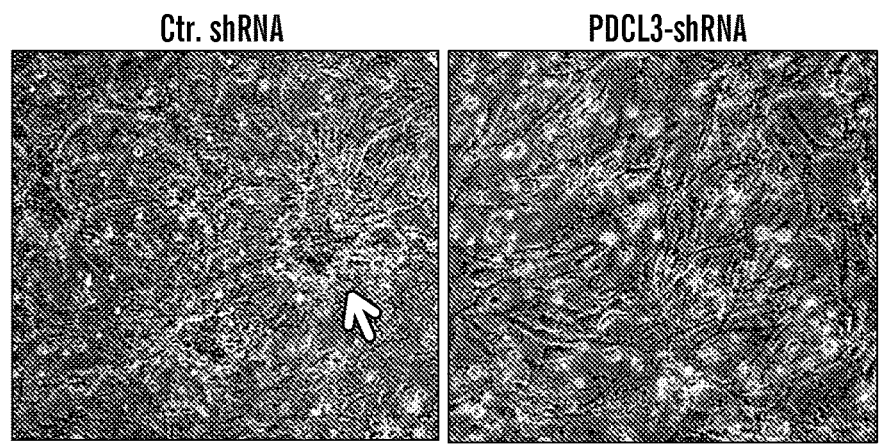
Figure 13D:
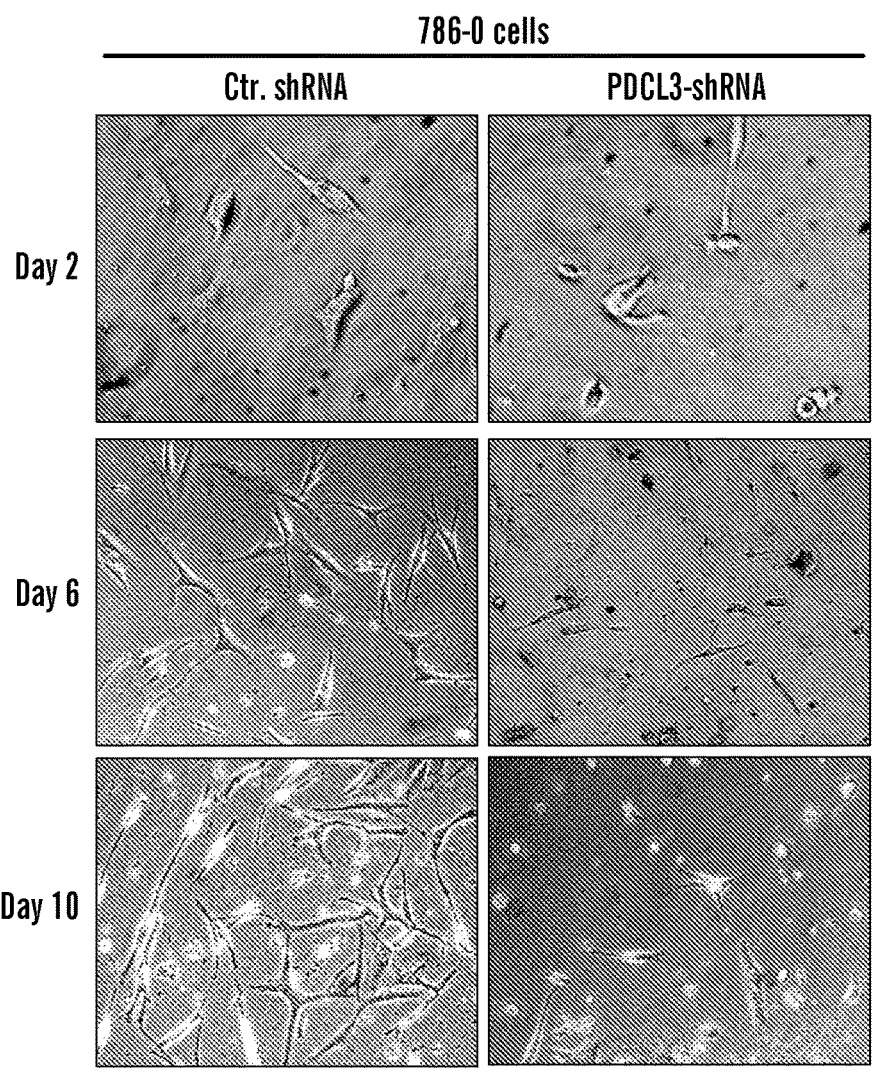

Given the important role of PDCL3 in the regulation of expression of various cell surface proteins including the important receptor tyrosine kinases such as VEGFR-1, VEGFR-2, and CSF-1R which are known to play critical role in tumor growth, we hypothesized, without wishing to be bound or limited by theory, that reducing expression of PDCL3 in tumor cells, in principle, could reduce their growth by decreasing expression of growth factor receptors. To test this, we silenced expression of PDCL3 by shRNA in kidney tumor cells, 786-O. Our data demonstrated that reducing expression of PDCL3 reduced expression of VEGFR-2 and decreased proliferation of tumor cells (FIG. 13B). Moreover, reducing expression of PDCL3 also reduced their foci formation, the hallmark of cell transformation (FIG. 13D). The data indicate therapeutic applications of PDCL3 in cancer therapeutics. In this regard, targeting of PDCL3 by small molecule inhibitors offers novel anti-cancer therapies.

Figure 14B:
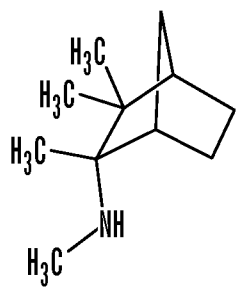
Figure 14B:
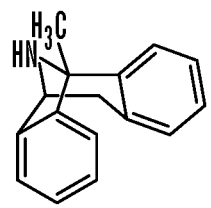
Figure 14B:
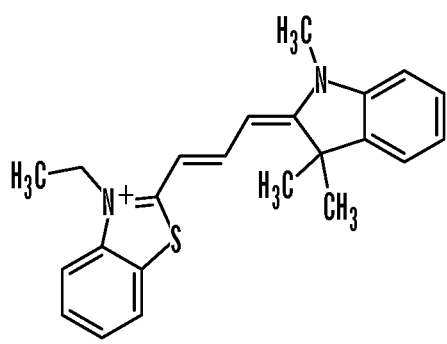
Figure 14B:
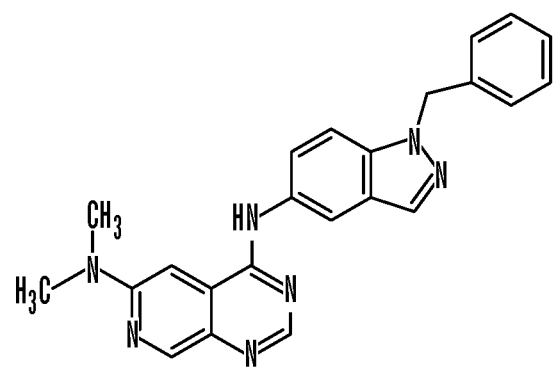
Figure 14B:
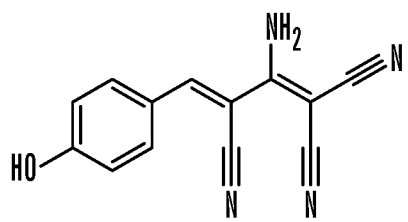
Figure 14B:
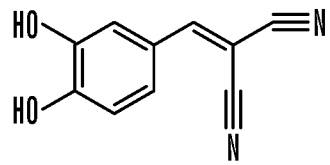
Figure 14B:
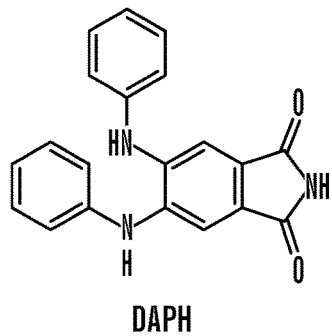
Figure 14B:
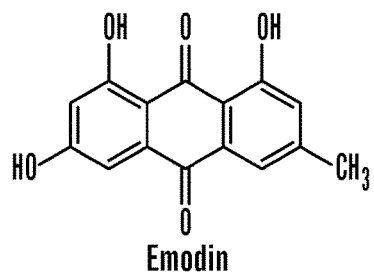
Figure 14B:
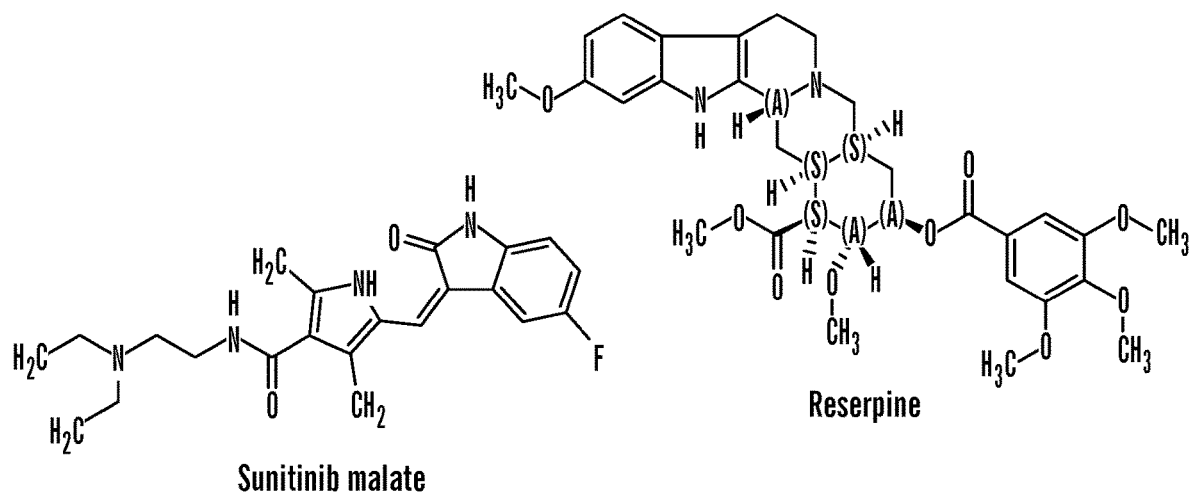
Figure 14B:
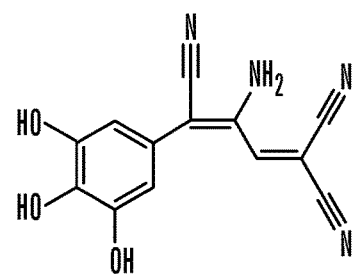
Figure 14B:
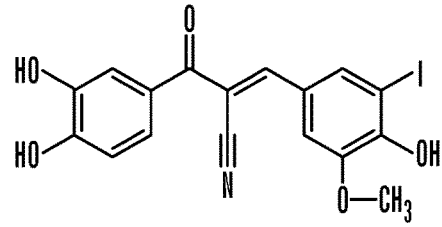
Figure 14B:
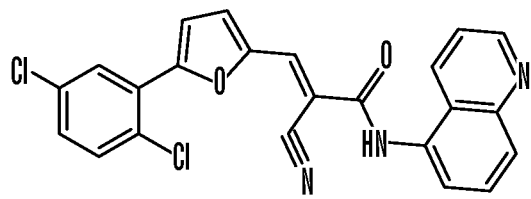
Figure 14B:
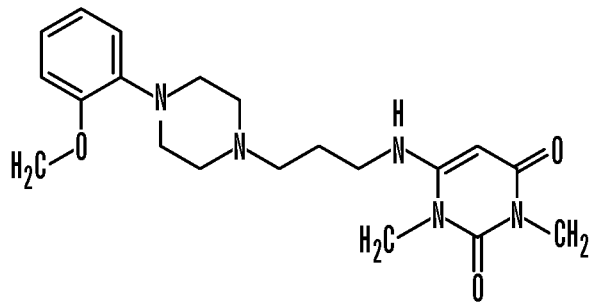
Figure 14B:
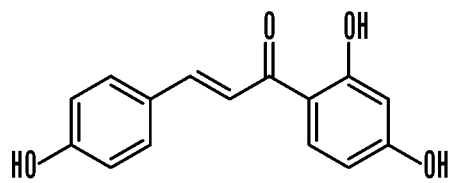

As demonstrated herein, novel small molecule inhibitors for PDCL3 were identified using high throughput screening. Given that PDCL3 plays a fundamental role in maturation and folding of receptor tyrosine kinases (RTKs), such as VEGFR-2, and considering that activity of these RTKs are cornerstone of tumor growth and metastasis, it was decided to screen for small molecule inhibitors that could antagonize PDCL3 function in tumor cells. LOPAC1280 (a library of Pharmacologically Active Compounds), which is a collection of 1,280 pharmacologically active compounds, was used. The library is most commonly used to validate new drug discovery assays and characterize orphan targets. 16 lead compounds were identified as PDCL3 inhibitors and their potency and efficacy in inhibition of PDCL3 was validated. As shown at FIGS. 14A-14B, the small molecule agents that were identified as specifically targeting PDCL3 include Reserpine, DAPH, AC-93253 iodide, Emodin, Sunitinib malate, GW2974, Urapidil Hydrochloride, Mecamylamine hydrochloride, (−)-MK-801 hydrogen maleate, AGK2, Tyrphostin AG 112, Tyrphostin 23, Tyrphostin 51, I-Ome-Tyrophostin AG 538, and Isoliquiritgenin. Chemical formulas for these compounds are provided herein in FIG. 14B.

REFERENCES

1. Rahimi N. The ubiquitin-proteasome system meets angiogenesis. *Molecular cancer therapeutics.* 2012; 11:538-548
2. Carmeliet P, Jain R K. Molecular mechanisms and clinical applications of angiogenesis. *Nature.* 2011; 473:298-307
3. Folkman J. Role of angiogenesis in tumor growth and metastasis. *Seminars in oncology.* 2002; 29:15-18
4. Carmeliet P, Tessier-Lavigne M. Common mechanisms of nerve and blood vessel wiring. *Nature.* 2005; 436:193-200
5. Rahimi N. Vascular endothelial growth factor receptors: Molecular mechanisms of activation and therapeutic potentials. *Experimental eye research.* 2006; 83:1005-1016
6. Matsumoto T, Claesson-Welsh L. Vegf receptor signal transduction. *Sci STKE.* 2001; 2001:re21
7. Rahimi N, Dayanir V, Lashkari K. Receptor chimeras indicate that the vascular endothelial growth factor receptor-1 (vegfr-1) modulates mitogenic activity of vegfr-2 in endothelial cells. *The Journal of biological chemistry.* 2000; 275:16986-16992
8. Buysschaert I, Carmeliet P, Dewerchin M. Clinical and fundamental aspects of angiogenesis and anti-angiogenesis. *Acta Clin Belg.* 2007; 62:162-169
9. Ferrara N. Vascular endothelial growth factor: Molecular and biological aspects. *Current topics in microbiology and immunology.* 1999; 237:1-30
10. Shibuya M, Luo J C, Toyoda M, Yamaguchi S. Involvement of vegf and its receptors in ascites tumor formation. *Cancer chemotherapy and pharmacology.* 1999; 43 Suppl:S72-77
11. Carmeliet P. Angiogenesis in health and disease. *Nature medicine.* 2003; 9:653-660
12. Rahimi N. Vegfr-1 and vegfr-2: Two non-identical twins with a unique physiognomy. *Frontiers in bioscience: a journal and virtual library.* 2006; 11:818-829
13. Hartsough E J, Meyer R D, Chitalia V, Jiang Y, Marquez V E, Zhdanova I V, Weinberg J, Costello C E, Rahimi N. Lysine methylation promotes vegfr-2 activation and angiogenesis. *Science signaling.* 2013; 6:ra104
14. Meyer R D, Srinivasan S, Singh A J, Mahoney J E, Gharahassanlou K R, Rahimi N. Pest motif serine and tyrosine phosphorylation controls vascular endothelial growth factor receptor 2 stability and downregulation. *Molecular and cellular biology.* 2011; 31:2010-2025
15. Sawamiphak S, Seidel S, Essmann C L, Wilkinson G A, Pitulescu M E, Acker T, Acker-Palmer A. Ephrin-b2 regulates vegfr2 function in developmental and tumour angiogenesis. *Nature.* 2010; 465:487-491
16. Lampugnani M G, Orsenigo F, Gagliani M C, Tacchetti C, Dejana E. Vascular endothelial cadherin controls vegfr-2 internalization and signaling from intracellular compartments. *The Journal of cell biology.* 2006; 174:593-604
17. He Y, Zhang H, Yu L, Gunel M, Boggon T J, Chen H, Min W. Stabilization of vegfr2 signaling by cerebral cavernous malformation 3 is critical for vascular development. *Science signaling.* 2010; 3:ra26
18. Bruns A F, Yuldasheva N, Latham A M, Bao L, Pellet-Many C, Frankel P, Stephen S L, Howell G J, Wheatcroft S B, Kearney M T, Zachary I C, Ponnambalam S. A heat-shock protein axis regulates vegfr2 proteolysis, blood vessel development and repair. *PloS one.* 2012; 7:e48539

19. Detmar M. Molecular regulation of angiogenesis in the skin. *The Journal of investigative dermatology.* 1996; 106:207-208
20. Schmidt T, Carmeliet P. Angiogenesis: A target in solid tumors, also in leukemia?*Hematology Am Soc Hematol Educ Program.* 2011; 2011:1-8
21. Bass J, Chiu G, Argon Y, Steiner D F. Folding of insulin receptor monomers is facilitated by the molecular chaperones calnexin and calreticulin and impaired by rapid dimerization. *The Journal of cell biology.* 1998; 141:637-646
22. Young J C, Agashe V R, Siegers K, Hartl F U. Pathways of chaperone-mediated protein folding in the cytosol. *Nature reviews. Molecular cell biology.* 2004; 5:781-791
23. Hampton R Y. Er-associated degradation in protein quality control and cellular regulation. *Current opinion in cell biology.* 2002; 14:476-482
24. Kostova Z, Wolf D H. For whom the bell tolls: Protein quality control of the endoplasmic reticulum and the ubiquitin-proteasome connection. *The EMBO journal.* 2003; 22:23092317
25. Srinivasan S, Meyer R D, Lugo R, Rahimi N. Identification of pdcl3 as a novel chaperone protein involved in the generation of functional vegf receptor 2. *The Journal of biological chemistry.* 2013; 288:23171-23181
26. Flanary P L, DiBello P R, Estrada P, Dohlman H G. Functional analysis of plp1 and plp2, two homologues of phosducin in yeast. *The Journal of biological chemistry.* 2000; 275:18462-18469
27. Blaauw M, Knol J C, Kortholt A, Roelofs J, Ruchira, Postma M, Visser A J, van Haastert P J. Phosducin-like proteins in dictyostelium discoideum: Implications for the phosducin family of proteins. *The EMBO journal.* 2003; 22:5047-5057
28. Humrich J, Bermel C, Bunemann M, Harmark L, Frost R, Quitterer U, Lohse M J. Phosducin-like protein regulates g-protein betagamma folding by interaction with tailless complex polypeptide-1alpha: Dephosphorylation or splicing of ph1p turns the switch toward regulation of gbetagamma folding. *The Journal of biological chemistry.* 2005; 280:20042-20050
29. Klausner R D, Donaldson J G, Lippincott-Schwartz J. Brefeldin a: Insights into the control of membrane traffic and organelle structure. *The Journal of cell biology.* 1992; 116:1071-1080
30. Helms J B, Rothman J E. Inhibition by brefeldin a of a golgi membrane enzyme that catalyses exchange of guanine nucleotide bound to arf. *Nature.* 1992; 360:352-354
31. Frydman J. Folding of newly translated proteins in vivo: The role of molecular chaperones. *Annual review of biochemistry.* 2001; 70:603-647
32. Hendrick J P, Langer T, Davis T A, Hartl F U, Wiedmann M. Control of folding and membrane translocation by binding of the chaperone dnaj to nascent polypeptides. *Proceedings of the National Academy of Sciences of the United States of America.* 1993; 90:10216-10220
33. Singh A J, Meyer R D, Band H, Rahimi N. The carboxyl terminus of vegfr-2 is required for pkc-mediated down-regulation. *Molecular biology of the cell.* 2005; 16:2106-2118
34. Serbedzija G N, Flynn E, Willett C E. Zebrafish angiogenesis: A new model for drug screening. *Angiogenesis.* 1999; 3:353-359
35. Nicoli S, Ribatti D, Cotelli F, Presta M. Mammalian tumor xenografts induce neovascularization in zebrafish embryos. *Cancer research.* 2007; 67:2927-2931
36. Millauer B, Wizigmann-Voos S, Schnurch H, Martinez R, Moller N P, Risau W, Ullrich A. High affinity vegf binding and developmental expression suggest flk-1 as a major regulator of vasculogenesis and angiogenesis. *Cell.* 1993; 72:835-846
37. Heidenreich R, Rocken M, Ghoreschi K. Angiogenesis: The new potential target for the therapy of psoriasis? *Drug news & perspectives.* 2008; 21:97-105
38. Pugh C W, Ratcliffe P J. Regulation of angiogenesis by hypoxia: Role of the hif system. *Nature medicine.* 2003; 9:677-684
39. Rahimi N. A role for protein ubiquitination in vegfr-2 signalling and angiogenesis. *Biochemical Society transactions.* 2009; 37:1189-1192
40. Smith L E. Pathogenesis of retinopathy of prematurity. *Growth hormone & IGF research: official journal of the Growth Hormone Research Society and the International IGF Research Society.* 2004; 14 Suppl A:S140-144
41. Stahl A, Connor K M, Sapieha P, Chen J, Dennison R J, Krah N M, Seaward M R, Willett K L, Aderman C M, Guerin K I, Hua J, Lofqvist C, Hellstrom A, Smith L E. The mouse retina as an angiogenesis model. *Investigative ophthalmology & visual science.* 2010; 51:2813-2826
42. Hwang C S, Shemorry A, Varshavsky A. N-terminal acetylation of cellular proteins creates specific degradation signals. *Science.* 2010; 327:973-977
43. Hwang C S, Shemorry A, Auerbach D, Varshavsky A. The n-end rule pathway is mediated by a complex of the ring-type ubr1 and hect-type ufd4 ubiquitin ligases. *Nature cell biology.* 2010; 12:1177-1185
44. Carmeliet P. Angiogenesis in life, disease and medicine. *Nature.* 2005; 438:932-936
45. Tang N, Wang L, Esko J, Giordano F J, Huang Y, Gerber H P, Ferrara N, Johnson R S. Loss of hif-1alpha in endothelial cells disrupts a hypoxia-driven vegf autocrine loop necessary for tumorigenesis. *Cancer cell.* 2004; 6:485-495
46. Ferrara N. Vascular endothelial growth factor: Basic science and clinical progress. *Endocrine reviews.* 2004; 25:581-611
47. Heidenreich R, Murayama T, Silver M, Essl C, Asahara T, Rocken M, Breier G. Tracking adult neovascularization during ischemia and inflammation using vegfr2-lacz reporter mice. *Journal of vascular research.* 2008; 45:437-444
48. Kremer C, Breier G, Risau W, Plate K H. Up-regulation of flk-1/vascular endothelial growth factor receptor 2 by its ligand in a cerebral slice culture system. *Cancer research.* 1997; 57:3852-3859
49. dela Paz N G, Walshe T E, Leach L L, Saint-Geniez M, D'Amore P A. Role of shear-stress-induced vegf expression in endothelial cell survival. *Journal of cell science.* 2012; 125:831-843
50. Schmidt T, Carmeliet P. Blood-vessel formation: Bridges that guide and unite. *Nature.* 2010; 465:697-699
51. Kim Y E, Hipp M S, Bracher A, Hayer-Hartl M, Hartl F U. Molecular chaperone functions in protein folding and proteostasis. *Annual review of biochemistry.* 2013; 82:323-355
52. Hendrick J P, Hartl F U. Molecular chaperone functions of heat-shock proteins. *Annual review of biochemistry.* 1993; 62:349-384
53. Rahimi N, Dayanir V, Lashkari K. Receptor chimeras indicate that the vascular endothelial growth factor receptor-1 (vegfr-1) modulates mitogenic activity of vegfr-2 in endothelial cells. *The Journal of biological chemistry.* 2000; 275:16986-16992

54. Stahl A, Connor K M, Sapieha P, Chen J, Dennison R J, Krah N M, Seaward M R, Willett K L, Aderman C M, Guerin K I, Hua J, Lofqvist C, Hellstrom A, Smith L E. The mouse retina as an angiogenesis model. Investigative ophthalmology & visual science. 2010; 51:2813-2826

55. Srinivasan S, Chitalia V, Meyer R D, Hartsough E, Mehta M, Harrold I, Anderson N, Feng H, Smith L E, Jiang Y, Costello C E, Rahimi N: Hypoxia-induced expression of phosducin-like 3 regulates expression of VEGFR-2 and promotes angiogenesis, Angiogenesis 2015,

I claim:

1. An engineered phosducin-like 3 (PDCL3) polypeptide antagonist consisting of SEQ ID NO: 9 and an N-terminal modification
an N-terminal modification.

2. The engineered PDCL3 polypeptide antagonist of claim 1, wherein the N-terminal modification is an acetylation-resistant N-terminal methionine.

3. The engineered PDCL3 polypeptide antagonist of claim 1, wherein the N-terminal modification is a fusion domain.

4. The engineered PDCL3 polypeptide antagonist of claim 1, wherein the engineered PDCL3 polypeptide antagonist inhibits VEGFR-2 mediated angiogenesis as determined using an angiogenesis assay wherein the inhibition is not 100% inhibition.

5. The engineered PDCL3 polypeptide antagonist of claim 4, wherein the angiogenesis assay is a zebrafish angiogenesis assay.

6. The engineered PDCL3 polypeptide antagonist of claim 1, wherein the N-terminal modification is selected from the group consisting of polyhistidine, Glu-Glu, thioredoxin, protein A, protein G, an immunoglobulin heavy chain constant region (Fc), maltose binding protein (MBP), a human serum albumin protein, and a fluorescent protein.

7. A pharmaceutical composition comprising the engineered PDCL3 antagonist of claim 1, and a pharmaceutically acceptable carrier.

8. The composition of claim 7, wherein the engineered PDCL3 antagonist comprises an N-terminal modification that is an acetylation-resistant N-terminal methionine.

9. An engineered phosducin-like 3 (PDCL3) polypeptide antagonist consisting of SEQ ID NO: 9 and a thioredoxin domain.

10. The engineered PDCL3 polypeptide antagonist of claim 9, wherein the engineered PDCL3 polypeptide antagonist reduces the association between a juxtamembrane domain of a VEGFR-2 protein and endogenous PDCL3 wherein the reduction is not 100% reduction, and wherein the VEGFR-2 mediated activity is reduced compared to VEGFR-2-mediated activity in the absence of the PDCL3 polypeptide antagonist wherein the reduction is not 100% reduction.

11. A pharmaceutical composition comprising the engineered PDCL3 antagonist of claim 9, and a pharmaceutically acceptable carrier.

* * * * *